US009669113B1

(12) United States Patent
Sirimanne et al.

(10) Patent No.: US 9,669,113 B1
(45) Date of Patent: Jun. 6, 2017

(54) DEVICE AND METHOD FOR SAFE LOCATION AND MARKING OF A BIOPSY CAVITY

(75) Inventors: D. Laksen Sirimanne, Palo Alto, CA (US); Natalie V. Fawzi, Belmont, CA (US); Douglas S. Sutton, Pacifica, CA (US); Gail S. Lebovic, Palo Alto, CA (US); Stanley R. Conston, San Carlos, CA (US); Peter M. Wilson, Foster City, CA (US); Anne B. Morrissey, Menlo Park, CA (US); Mary Elizabeth Bush, San Pedro, CA (US)

(73) Assignee: DEVICOR MEDICAL PRODUCTS, INC., Sharonville, OH (US)

( * ) Notice: Subject to any disclaimer, the term of this patent is extended or adjusted under 35 U.S.C. 154(b) by 434 days.

(21) Appl. No.: 09/869,282

(22) PCT Filed: Dec. 23, 1999

(86) PCT No.: PCT/US99/30619
§ 371 (c)(1),
(2), (4) Date: Jun. 18, 2002

(87) PCT Pub. No.: WO00/38579
PCT Pub. Date: Jul. 6, 2000

Related U.S. Application Data

(63) Continuation-in-part of application No. 09/347,185, filed on Jul. 2, 1999, now Pat. No. 6,371,904, which
(Continued)

(51) Int. Cl.
*A61B 6/00* (2006.01)
*A61K 49/00* (2006.01)
(Continued)

(52) U.S. Cl.
CPC ............ *A61K 49/006* (2013.01); *A61B 90/39* (2016.02); *A61B 2017/00539* (2013.01);
(Continued)

(58) Field of Classification Search
USPC ................................. 600/436, 564, 567, 585
See application file for complete search history.

(56) References Cited

U.S. PATENT DOCUMENTS

| 2,609,347 A | 9/1952 | Wilson |
| 2,653,917 A | 9/1953 | Hammon |

(Continued)

FOREIGN PATENT DOCUMENTS

| CA | 2071840 | 2/1997 |
| DE | 935625 | 5/1955 |

(Continued)

OTHER PUBLICATIONS

Robinson et al. (Biocompatibility of Compressed Collagen Foam Plugs), Cardiovascular and Interventional Radiology, vol. 13, 1990, 36-39.*

(Continued)

*Primary Examiner* — Long V Le
*Assistant Examiner* — Ellsworth Weatherby
(74) *Attorney, Agent, or Firm* — Arent Fox LLP

(57) ABSTRACT

Cavity and sentinel lymph node marking devices, marker delivery devices, and methods are disclosed. More particularly, upon insertion into a body, the cavity marking device and method enable one to determine the center, orientation, and periphery of the cavity by radiographic, mammography, echogenic, or other noninvasive imaging techniques. A composition and method are disclosed for locating the sentinel lymph node in a mammalian body to determine if cancerous cells have spread thereto. The composition is preferably a fluid composition consisting of a carrier fluid (Continued)

and some type of contrast agent; alternatively, the contrast agent may itself be a fluid and therefore not need a separate carrier fluid. This composition is capable of (1) deposition in or around a lesion and migration to and accumulation in the associated sentinel node, and (2) remote detection via any number of noninvasive techniques. Also disclosed is a method for remotely detecting the location of a sentinel node by (1) depositing a remotely detectable fluid in or around a lesion for migration to and accumulation in the associated sentinel node and (2) remotely detecting the location of that node with a minimum of trauma and toxicity to the patient. The composition and method may serve to mark a biopsy cavity, as well as mark the sentinel lymph node. The marking methods also may combine any of the features as described with the marking device and delivery device.

4 Claims, 35 Drawing Sheets

Related U.S. Application Data is a continuation-in-part of application No. 09/285,329, filed on Apr. 2, 1999, now Pat. No. 6,356,782, which is a continuation-in-part of application No. 09/220,618, filed on Dec. 24, 1998, now abandoned.

(51) Int. Cl.
 A61B 90/00 (2016.01)
 A61B 17/00 (2006.01)
(52) U.S. Cl.
 CPC .......... A61B 2090/3925 (2016.02); A61B 2090/3966 (2016.02); A61B 2090/3987 (2016.02); A61B 2090/3995 (2016.02)

(56) References Cited

U.S. PATENT DOCUMENTS

| | | | |
|---|---|---|---|
| 2,659,935 | A | 11/1953 | Hammon |
| 2,664,366 | A | 12/1953 | Wilson |
| 2,664,367 | A | 12/1953 | Wilson |
| 2,740,405 | A | 4/1956 | Riordan |
| 2,846,407 | A | 8/1958 | Wilson |
| 2,972,350 | A | 2/1961 | Deker |
| 3,001,522 | A | 9/1961 | Silverman |
| 3,194,239 | A | 7/1965 | Sullivan |
| 3,314,420 | A | 4/1967 | Smith et al. |
| 3,592,185 | A | 7/1971 | Frei et al. |
| 3,736,935 | A | 6/1973 | Reimels |
| 3,823,212 | A | 7/1974 | Chvapil |
| 3,844,272 | A | 10/1974 | Banko |
| 4,087,791 | A | 5/1978 | Lemberger |
| 4,114,601 | A | 9/1978 | Abels |
| 4,127,110 | A | 11/1978 | Bullara |
| 4,197,846 | A | 4/1980 | Bucalo |
| 4,202,349 | A | 5/1980 | Jones |
| 4,230,123 | A | 10/1980 | Hawkins, Jr. |
| 4,291,013 | A | 9/1981 | Wahlig et al. |
| 4,298,998 | A | 11/1981 | Naficy |
| 4,320,321 | A | 3/1982 | Alexandrov et al. |
| 4,347,234 | A | 8/1982 | Wahlig et al. |
| 4,356,572 | A | 11/1982 | Guellemin |
| 4,541,438 | A | 9/1985 | Parker et al. |
| 4,626,251 | A | 12/1986 | Shen |
| 4,628,944 | A | 12/1986 | MacGregor et al. |
| 4,636,208 | A | 1/1987 | Rath |
| 4,639,253 | A | 1/1987 | Dyer et al. |
| 4,645,499 | A | 2/1987 | Rupinskas |
| 4,682,606 | A | 7/1987 | DeCaprio |
| 4,693,237 | A | 9/1987 | Hoffman |
| 4,704,109 | A | 11/1987 | Rupinskas |
| 4,718,897 | A | 1/1988 | Elves |
| 4,735,210 | A | 4/1988 | Goldenberg |
| 4,735,796 | A | 4/1988 | Gordon |
| 4,744,364 | A | 5/1988 | Kensey |
| 4,787,391 | A | 11/1988 | Elefteriades |
| 4,789,401 | A | 12/1988 | Ebinger |
| 4,795,463 | A | 1/1989 | Gerow |
| 4,803,075 | A | 2/1989 | Wallace et al. |
| 4,812,120 | A | 3/1989 | Flanagan et al. |
| 4,832,686 | A | 5/1989 | Anderson |
| 4,852,568 | A | 8/1989 | Kensey et al. |
| 4,863,470 | A | 9/1989 | Carter |
| 4,909,250 | A | 3/1990 | Smith |
| 4,917,694 | A | 4/1990 | Jessup |
| 4,944,308 | A | 7/1990 | Akerfeldt |
| 4,966,583 | A | 10/1990 | Debbas |
| 4,970,298 | A | 11/1990 | Silver |
| 4,985,019 | A | 1/1991 | Michelson |
| 4,986,682 | A | 1/1991 | Lu |
| 5,002,548 | A | 3/1991 | Campbell |
| 5,018,530 | A | 5/1991 | Rank |
| 5,041,103 | A | 8/1991 | Rupinskas |
| 5,041,826 | A | 8/1991 | Milheiser |
| 5,045,080 | A | 9/1991 | Dyer et al. |
| 5,057,095 | A | 10/1991 | Fabian |
| 5,059,197 | A | 10/1991 | Urie et al. |
| 5,085,629 | A | 2/1992 | Goldberg et al. |
| 5,100,429 | A | 3/1992 | Sinofsky et al. |
| 5,101,827 | A | 4/1992 | Goldenberg |
| 5,108,421 | A | 4/1992 | Fowler |
| 5,111,828 | A | 5/1992 | Kornberg et al. |
| 5,112,325 | A | 5/1992 | Zachry |
| 5,114,703 | A | 5/1992 | Wolf et al. |
| 5,120,802 | A | 6/1992 | Mares |
| 5,127,916 | A | 7/1992 | Spencer |
| 5,148,813 | A | 9/1992 | Bucalo |
| 5,183,463 | A | 2/1993 | Debbas |
| 5,192,300 | A | 3/1993 | Fowler |
| 5,195,540 | A | 3/1993 | Shiber |
| 5,195,988 | A | 3/1993 | Haaga |
| 5,197,482 | A | 3/1993 | Rank et al. |
| 5,197,484 | A | 3/1993 | Kornberg et al. |
| 5,201,314 | A | 4/1993 | Bosley et al. |
| 5,204,382 | A | 4/1993 | Wallace |
| 5,207,705 | A | 5/1993 | Trudell et al. |
| 5,221,269 | A | 6/1993 | Miller |
| 5,235,326 | A | 8/1993 | Biegel et al. |
| 5,252,962 | A | 10/1993 | Urbas et al. |
| 5,275,616 | A | 1/1994 | Fowler |
| 5,281,197 | A | 1/1994 | Arias et al. |
| 5,300,120 | A | 4/1994 | Knapp et al. |
| 5,301,682 | A | 4/1994 | Debbas |
| 5,320,100 | A * | 6/1994 | Herweck et al. ............ 600/431 |
| 5,324,775 | A | 6/1994 | Rhee et al. |
| 5,326,350 | A | 7/1994 | Li |
| 5,329,944 | A | 7/1994 | Fabian et al. |
| 5,334,216 | A | 8/1994 | Vidal et al. |
| 5,353,804 | A | 10/1994 | Kornberg et al. |
| 5,374,246 | A | 12/1994 | Ray |
| 5,376,376 | A | 12/1994 | Li |
| 5,380,646 | A | 1/1995 | Knight et al. |
| 5,382,251 | A | 1/1995 | Hood et al. |
| 5,388,588 | A | 2/1995 | Nabai et al. |
| 5,394,875 | A | 3/1995 | Lewis et al. |
| 5,394,886 | A | 3/1995 | Nabai et al. |
| 5,403,306 | A | 4/1995 | Edwards et al. |
| 5,405,402 | A | 4/1995 | Dye et al. |
| 5,409,004 | A | 4/1995 | Sloan |
| 5,422,636 | A | 6/1995 | Urbas et al. |
| 5,433,751 | A | 7/1995 | Christel |
| 5,437,279 | A | 8/1995 | Gray |
| 5,444,113 | A | 8/1995 | Sinclair et al. |
| 5,451,406 | A | 9/1995 | Lawin et al. |
| 5,456,693 | A | 10/1995 | Conston et al. |
| 5,456,718 | A | 10/1995 | Szymaitis |
| 5,460,182 | A | 10/1995 | Goodman et al. |
| 5,467,780 | A | 11/1995 | Nabai et al. |
| 5,478,352 | A | 12/1995 | Fowler |
| 5,482,040 | A | 1/1996 | Martin, Jr. |

(56) References Cited

U.S. PATENT DOCUMENTS

| | | | |
|---|---|---|---|
| 5,487,392 A | 1/1996 | Haaga | |
| 5,496,536 A | 3/1996 | Wolf | |
| 5,507,813 A | 4/1996 | Dowd | |
| 5,511,566 A | 4/1996 | Brand | |
| 5,514,379 A | 5/1996 | Weissleder et al. | |
| 5,518,730 A | 5/1996 | Fuisz | |
| 5,531,716 A | 7/1996 | Luzio et al. | |
| 5,546,957 A | 8/1996 | Heske | |
| 5,555,885 A | 9/1996 | Chance | |
| 5,560,373 A | 10/1996 | De Santis | |
| 5,571,181 A | 11/1996 | Li | |
| 5,571,182 A | 11/1996 | Ersek et al. | |
| 5,575,781 A | 11/1996 | DeBusk | |
| 5,579,766 A | 12/1996 | Gray | |
| 5,582,172 A | 12/1996 | Papisov et al. | |
| 5,595,177 A | 1/1997 | Mena et al. | |
| 5,626,603 A | 5/1997 | Venturelli et al. | |
| 5,626,611 A | 5/1997 | Liu | |
| 5,628,744 A | 5/1997 | Coleman et al. | |
| 5,632,775 A | 5/1997 | Suding et al. | |
| 5,633,286 A | 5/1997 | Chen | |
| 5,645,566 A | 7/1997 | Brenneman et al. | |
| 5,662,712 A | 9/1997 | Pathak et al. | |
| 5,664,582 A | 9/1997 | Szymaitis | |
| 5,665,063 A | 9/1997 | Roth | |
| 5,670,161 A | 9/1997 | Healy et al. | |
| 5,674,288 A | 10/1997 | Knapp et al. | |
| 5,676,146 A | 10/1997 | Scarborough | |
| 5,693,085 A | 12/1997 | Buirge et al. | |
| 5,697,384 A | 12/1997 | Miyawaki et al. | |
| 5,697,902 A | 12/1997 | Goldenberg | |
| 5,702,449 A * | 12/1997 | McKay | 623/17.16 |
| 5,707,393 A | 1/1998 | Kensey et al. | |
| 5,709,676 A | 1/1998 | Alt | |
| 5,714,551 A | 2/1998 | Bezwada et al. | |
| 5,716,404 A | 2/1998 | Vicante | |
| 5,716,407 A | 2/1998 | Knapp et al. | |
| 5,718,237 A | 2/1998 | Haaga | |
| 5,720,772 A | 2/1998 | Eckhouse | |
| 5,723,004 A | 3/1998 | Dereume et al. | |
| 5,725,517 A | 3/1998 | DeBusk | |
| 5,725,578 A | 3/1998 | Knapp et al. | |
| 5,732,704 A | 3/1998 | Thurston et al. | |
| 5,752,974 A | 5/1998 | Rhee et al. | |
| 5,776,093 A | 7/1998 | Goldenberg | |
| 5,776,094 A | 7/1998 | Goldenberg | |
| 5,776,095 A | 7/1998 | Goldenberg | |
| 5,795,308 A | 8/1998 | Russin | |
| 5,803,913 A | 9/1998 | Khalkhali et al. | |
| 5,807,276 A | 9/1998 | Russin | |
| 5,807,581 A | 9/1998 | Rosenblatt et al. | |
| 5,810,806 A | 9/1998 | Ritchart et al. | |
| 5,817,017 A | 10/1998 | Young et al. | |
| 5,817,033 A | 10/1998 | DeSantis et al. | |
| 5,823,198 A | 10/1998 | Jones et al. | |
| 5,827,531 A | 10/1998 | Morrison et al. | |
| 5,833,603 A | 11/1998 | Kovacs et al. | |
| 5,853,366 A | 12/1998 | Dowlatshahi | |
| 5,855,609 A | 1/1999 | Knapp | |
| 5,856,367 A | 1/1999 | Barrows et al. | |
| 5,857,463 A | 1/1999 | Thurston et al. | |
| 5,857,998 A | 1/1999 | Barry | |
| 5,868,778 A | 2/1999 | Gershony et al. | |
| 5,869,080 A | 2/1999 | McGregor | |
| 5,871,501 A | 2/1999 | Leschinsky et al. | |
| 5,871,535 A | 2/1999 | Wolf et al. | |
| 5,873,904 A | 2/1999 | Ragheb et al. | |
| 5,879,357 A * | 3/1999 | Heaton et al. | 606/116 |
| 5,895,395 A | 4/1999 | Yeung | |
| 5,895,640 A | 4/1999 | Khalkhali | |
| 5,899,865 A | 5/1999 | Chance | |
| 5,913,857 A | 6/1999 | Ritchart et al. | |
| 5,922,024 A | 7/1999 | Janzen | |
| 5,923,001 A | 7/1999 | Morris et al. | |
| 5,935,147 A | 8/1999 | Kensey et al. | |
| 5,941,890 A | 8/1999 | Voegele | |
| 5,941,910 A | 8/1999 | Schindler | |
| 5,962,572 A | 10/1999 | Chen | |
| 5,970,986 A | 10/1999 | Bolz et al. | |
| 5,977,431 A | 11/1999 | Knapp et al. | |
| 5,980,564 A | 11/1999 | Stinson | |
| 5,989,265 A | 11/1999 | Bouquet De La Joliniere et al. | |
| 5,997,468 A | 12/1999 | Wolff | |
| 6,006,750 A | 12/1999 | Field | |
| 6,007,495 A | 12/1999 | Matula | |
| 6,013,031 A | 1/2000 | Mendlein et al. | |
| 6,026,818 A | 2/2000 | Blair et al. | |
| 6,030,333 A | 2/2000 | Siohansi et al. | |
| 6,056,700 A * | 5/2000 | Burney et al. | 600/564 |
| 6,057,122 A | 5/2000 | Davidson | |
| 6,066,325 A | 5/2000 | Wallace | |
| 6,068,857 A | 5/2000 | Weitschies et al. | |
| 6,071,301 A | 6/2000 | Cragg et al. | |
| 6,080,099 A | 6/2000 | Slater et al. | |
| 6,083,167 A | 7/2000 | Fox et al. | |
| 6,083,522 A | 7/2000 | Chu | |
| 6,092,009 A | 7/2000 | Glover | |
| 6,106,473 A | 8/2000 | Violante et al. | |
| 6,117,176 A | 9/2000 | Chen | |
| 6,120,533 A | 9/2000 | Fischell | |
| 6,123,714 A | 9/2000 | Gia et al. | |
| 6,126,675 A | 10/2000 | Shchervinsky et al. | |
| 6,148,830 A | 11/2000 | Chen | |
| 6,159,165 A | 12/2000 | Ferrera et al. | |
| 6,161,034 A | 12/2000 | Burbank et al. | |
| 6,162,192 A * | 12/2000 | Cragg et al. | 604/15 |
| 6,168,570 B1 | 1/2001 | Ferrera | |
| 6,174,330 B1* | 1/2001 | Stinson | 623/1.34 |
| 6,179,860 B1 | 1/2001 | Fulton et al. | |
| 6,181,960 B1 | 1/2001 | Jensen et al. | |
| 6,183,497 B1 | 2/2001 | Sing et al. | |
| 6,197,324 B1 | 3/2001 | Crittenden | |
| 6,200,328 B1 | 3/2001 | Cragg et al. | |
| 6,206,914 B1 | 3/2001 | Soykan et al. | |
| 6,214,045 B1 | 4/2001 | Corbitt, Jr. et al. | |
| 6,220,248 B1* | 4/2001 | Voegele et al. | 128/898 |
| 6,228,055 B1* | 5/2001 | Foerster | A61B 19/54 604/116 |
| 6,231,598 B1 | 5/2001 | Berry et al. | |
| 6,231,834 B1 | 5/2001 | Unger et al. | |
| 6,234,177 B1 | 5/2001 | Barsch | |
| 6,241,691 B1 | 6/2001 | Ferrera et al. | |
| 6,251,135 B1 | 6/2001 | Stinson et al. | |
| 6,254,548 B1 | 7/2001 | Ishikawa et al. | |
| 6,254,633 B1* | 7/2001 | Pinchuk et al. | 623/1.3 |
| 6,261,243 B1 | 7/2001 | Burney et al. | |
| 6,264,686 B1 | 7/2001 | Rieu et al. | |
| 6,270,464 B1 | 8/2001 | Fulton, III et al. | |
| 6,304,766 B1 | 10/2001 | Colvin, Jr. | |
| 6,309,420 B1* | 10/2001 | Preissman | 623/16.11 |
| 6,340,367 B1 | 1/2002 | Stinson | |
| 6,347,241 B2 | 2/2002 | Burbank | |
| 6,356,782 B1 | 3/2002 | Sirimanne | |
| 6,363,940 B1 | 4/2002 | Krag | |
| 6,371,904 B1 | 4/2002 | Sirimanne | |
| 6,379,379 B1 | 4/2002 | Wang | |
| 6,409,674 B1 | 6/2002 | Brockway et al. | |
| 6,475,169 B2 | 11/2002 | Ferrera | |
| 6,484,050 B1* | 11/2002 | Carroll et al. | 600/436 |
| 6,497,671 B2 | 12/2002 | Ferrera et al. | |
| 6,616,617 B1 | 9/2003 | Ferrera et al. | |
| 6,659,996 B1* | 12/2003 | Kaldany | 604/508 |
| 6,666,811 B1 | 12/2003 | Good | |
| 6,716,179 B2* | 4/2004 | Burbank et al. | 600/564 |
| 6,749,554 B1 | 6/2004 | Snow et al. | |
| 6,766,186 B1 | 7/2004 | Hoyns et al. | |
| 6,811,776 B2 | 11/2004 | Kale et al. | |
| 6,813,520 B2* | 11/2004 | Truckai et al. | 607/101 |
| 7,044,957 B2 | 5/2006 | Foerster et al. | |
| 7,093,599 B2 | 8/2006 | Chen | |
| 7,229,417 B2 | 6/2007 | Foerster et al. | |
| 7,625,397 B2 | 12/2009 | Foerster et al. | |
| 7,668,582 B2 | 2/2010 | Sirimanne et al. | |
| 8,320,993 B2 | 11/2012 | Sirimanne et al. | |

(56) References Cited

U.S. PATENT DOCUMENTS

| | | | |
|---|---|---|---|
| 2001/0021873 A1 | 9/2001 | Stinson | |
| 2001/0034528 A1* | 10/2001 | Foerster et al. | 606/116 |
| 2001/0038823 A1 | 11/2001 | Rossling et al. | |
| 2001/0041936 A1 | 11/2001 | Corbitt, Jr. et al. | |
| 2001/0049481 A1* | 12/2001 | Fulton et al. | 600/573 |
| 2002/0012652 A1 | 1/2002 | Levy et al. | |
| 2002/0058883 A1* | 5/2002 | Fulton et al. | 600/562 |
| 2002/0107437 A1 | 8/2002 | Sirimanne | |
| 2002/0193815 A1 | 12/2002 | Foerster et al. | |
| 2004/0024304 A1 | 2/2004 | Foerster et al. | |
| 2004/0138555 A1 | 7/2004 | Krag et al. | |
| 2004/0193044 A1 | 9/2004 | Burbank | |
| 2005/0049489 A1 | 3/2005 | Foerster et al. | |
| 2005/0165305 A1 | 7/2005 | Foerster et al. | |
| 2006/0074443 A1 | 4/2006 | Foerster et al. | |
| 2010/0113920 A1 | 5/2010 | Foerster et al. | |

FOREIGN PATENT DOCUMENTS

| | | |
|---|---|---|
| DE | 0935625 | 11/1955 |
| DE | 43 30 958 A1 | 3/1995 |
| DE | 4330958 | 3/1995 |
| DE | 44 03 789 A1 | 8/1995 |
| DE | 4403789 | 8/1995 |
| EP | 0146699 | 7/1985 |
| EP | 0255123 | 2/1988 |
| EP | 0293605 | 12/1988 |
| EP | 0350043 | 1/1990 |
| EP | 0481685 | 4/1992 |
| EP | 0 534 696 A1 | 3/1993 |
| EP | 0534696 | 3/1993 |
| EP | 0 769 281 A2 | 4/1997 |
| EP | 0 769 281 A3 | 4/1997 |
| EP | 0769281 | 4/1997 |
| FR | 2 714 284 A1 | 6/1995 |
| FR | 2714284 | 6/1995 |
| GB | 2132091 | 7/1984 |
| WO | WO 9015576 | 12/1990 |
| WO | WO-9015576 | 12/1990 |
| WO | WO 9319803 | 10/1993 |
| WO | WO-9319803 | 10/1993 |
| WO | WO 96/08208 A1 | 3/1996 |
| WO | WO 9608208 | 3/1996 |
| WO | WO 96/27328 | 9/1996 |
| WO | WO 98/09247 | 3/1998 |
| WO | WO 9809247 | 3/1998 |
| WO | WO 98/43090 | 10/1998 |
| WO | WO 98/47430 | 10/1998 |
| WO | WO 9843090 | 10/1998 |
| WO | WO 9843900 A1 | 10/1998 |
| WO | WO 9847430 | 10/1998 |
| WO | WO 98/52616 | 11/1998 |
| WO | WO 98/52617 | 11/1998 |
| WO | WO 9852616 | 11/1998 |
| WO | WO 9852616 A2 | 11/1998 |
| WO | WO 9852617 | 11/1998 |
| WO | WO 9852617 A2 | 11/1998 |
| WO | WO 99/11196 | 3/1999 |
| WO | WO 9911196 | 3/1999 |
| WO | WO 9911196 A1 | 3/1999 |
| WO | WO 99/25248 | 5/1999 |
| WO | WO 9925248 | 5/1999 |
| WO | WO 9925248 A1 | 5/1999 |
| WO | WO 99/46284 | 9/1999 |
| WO | WO 9946284 | 9/1999 |
| WO | WO 9946284 A2 | 9/1999 |
| WO | WO 99/25248 | 11/1999 |
| WO | WO 99/46284 | 11/1999 |
| WO | WO 99/66834 | 12/1999 |
| WO | WO 9966834 | 12/1999 |
| WO | WO 9966834 A1 | 12/1999 |
| WO | WO 00/24320 A1 | 5/2000 |
| WO | WO 0024320 | 5/2000 |
| WO | WO-0024320 | 5/2000 |
| WO | WO 00/32253 A1 | 6/2000 |
| WO | WO 0030534 A1 | 6/2000 |
| WO | WO-0032253 | 6/2000 |
| WO | WO 0032253 | 6/2000 |
| WO | WO-0038579 | 7/2000 |
| WO | WO 0038579 | 7/2000 |
| WO | WO 00/45854 A2 | 8/2000 |
| WO | WO 00/45858 A1 | 8/2000 |
| WO | WO 0045854 | 8/2000 |
| WO | WO 0045858 | 8/2000 |
| WO | WO 01/00101 A1 | 1/2001 |
| WO | WO 0100101 | 1/2001 |

OTHER PUBLICATIONS

Fournier, C. et al., "Experimental Studies and Preliminary Clinical Trial of Vinorelbine-loaded Polymeric Bioresorable Implants for the Local treatment of Solid Tumors," *Cancer Research*, (1991) 51:5384-5391.

Hofman, "Biodegradable Implants in Orthopaedic Surgery—A Review on the State-of-the-Art," *Clinical Materials* (1992) 10:75-80.

Pangman, "The Use of Plastic Prosthesis in Breast Plastic and Other Soft Tissue Surgery." *The Western Journal of Surgery, Obstetrics and Gynecology*, (Aug. 1995) 508.

Clarkson, "Sponge Implants for Flat Breasts," *Proceedings of the Royal Society of Medicine*, (1960) vol. 53: 880-881.

PCT Search Report for PCT/US99/30619, dated Aug. 30, 2000.

Alesch, et al., "Marking of the Stereotactic Target Point by a Radiopaque Silicone Sphere," *Acta Neurochirurgica* (1992) vol. 115, 149-151.

Brannon-Peppas, Lisa, "Polymers in Controlled Drug Delivery," *Medical Plastics and Biomaterials* (1997) pp. 34-44.

Braverman, M.H. and Tawes, R.L. Eds., "Upjohn Gelfoam[R] Sterile Sponge and Sterile Powder advertisement," Surgical Technology: International Developments in Surgery and Surgical Research (1992) 3 pages.

Burbank, Fred and Forcier, Nancy, "Tissue Marking Clip for Stereotactic Breast Biopsy: Initial Placement Accuracy, Long-term Stability, and Usefulness as a Guide for Wire Localization," *Radiology* (1997) vol. 205, No. 2, pp. 407-415.

Clarkson, P.: "Sponge Implants for Flat Breasts," Proceedings of the Royal Society of Medicine, vol. 53 at 880-881 (1960).

Cohesion Technologies, Inc., "Business Summary," (Nov. 19, 1999) 3 pages, http://www.cohesiontech.com.

Dufrane, P. et al: "Prebiopsy Localization of Non-Palpable Breast Cancer," Journal Belgede Radiologie (Oct. 1, 1990) vol. 73, No. 5.

Ethicon Home Page, "Ethicon: Wound Closure," (1998) 1 page, http://www.eosinc.com.

Fournier et al: "Experimental Studies and Preliminary Clinical Trial of Vinorelbine-loaded Polymeric Bioresorbable Implants for the Local Treatment of Solid Tumors", Cancer Research 51, pp. 5384-5391, Oct. 1, 1991.

Freiherr, Greg, "Biotech Devices Promise Benefits in Wound Repair and Surgery," Medical Device & Diagnostic Industry Medicine (1997) 6 pages, www.devicelink.com.

Hachisu, et al., "Endoscopic Clip-Marking of Lesions Using the Newly Developed HX-3L Clip," Surgical Endoscopy (1989) vol. 3, pp. 142-147.

Hofmann et al: "Biodegradable Implants in Orthopaedic Surgery—A Review on the State-of-the-Art,"; Clinical Materials; vol. 10, 1992; pp. 75-80.

Hofmann, G.O.: "Biodegradable Implants in Traumatology A Review on the State-of-the-Art", Arch. Cathop Trauma Surgery, 1995, pp. 114: 123-132.

Katz, Jon and Spera, Gabriel, "Biomaterials Research Focuses on Developing New Applications," Medical Device & Diagnostic Industry Magazine (1998) 8 pages, www.devicelink.com.

Lebovic, G.S., "Utility of a Radiolucent, Bioabsorbable Marker Following Percutaneous Excision of Breast Lesions," University of Florida 5th Annual Multidisciplinary Breast Conference (Feb. 14-17, 2000) Poster, 2 pages.

(56) References Cited

OTHER PUBLICATIONS

Middleton, John and Tipton, Arthur, "Synthetic Biodegradable Polymers as Medical Devices," Medical Plastics and Biomaterials Magazine (1998) 17 pages, www.devicelink.com.
Pangman, W.J. and Wallace, R.M.: "The Use of Plastic Prosthesis in Breast Plastic and Other Soft Tissue Surgery," The Western Journal of Surgery, Obstetrics and Gynecology at 508 (Aug. 1955).
Parker, Steve, "Steps in a Steroetactic Mammotome Biopsy," Publication by Sally Jobe Breast Centre, (date unknown) pp. 1-5.
Publication by Medical Plastics and Biomaterials (1997) p. 61.
Storey, Robson and Wiggins, Jeffrey, "Design and Fabrication of Polyester-Fiber and Matrix Composites for Totally Absorbable Biomaterials," Medical Plastics and Biomaterials Magazine (1996) 6 pages, www.devicelink.com.
Trovan®: Electronic Identification Systems, "Trovan Transponders," (Dec. 13, 1999) 7 pages, http://www.trovan.com/transponders.htm.
Hahn, et al., "Vacuum-Assisted Breast Biopsy with Mammotone," Devicor Medical Germany GmbH, Springer Medizin Verlag, 2013.
International Search Report of related International Patent Application No. PCT/US99/30619 dated Aug. 30, 2000.
Robinson, et al., "The Biocompatability of Compressed Collagen Foam Plugs," Cardiovascular and Interventional Radiology, 13, pp. 36-39, 1990.
"The First FDA-approved Surgical Fibrin Sealant," *Tisseel VH Kit Firbirn Sealant*, Publication by Tisseel, 5 pages, date unknown.
Ethicon Home Page (1998) "Ethicon: Wound Closure," 1 page, (http://www.eosinc.com).
Freiherr, Greg. (1997). "Biotech Devices Promise Benefits in Wound Repair and Surgery," *Medical Device & Diagnostic Industry* Magazine, 6 pages (www.devicelink.com).
"The First FDA-approved Surgical Fibrin Sealant," *Tisseel VH Kit Firbirn Sealant*, Publication by Tisseel, 5 pages, date unknown.
Alesch et al., (1992) "Marking of the Stereotactic Target Point by a Radiopaque Silicone Sphere" *Acta Neurochirurgica* vol. 115, 149-151.
Braverman, M.H. and Tawes, R.L. eds., (Dec. 1992). "Upjohn Gelfoam® Sterile Sponge and Sterile Powder advertisement," *Surgical Technology: International Developments in Surgery and Surgical Research* (3 pages).
Brannon-Peppas, Lisa. (1997). "Polymers in Controlled Drug Delivery" *Medical Plastics and Biomaterials*, pp. 34-44.
Burbank, Fred and Forcier, Nancy. (1997). "Tissue Marking Clip for Stereotactic Breast Biopsy: Initial Placement Accuracy, Long-term Stability, and Usefulness as a Guide for Wire Localization," *Radiology* vol. 205 No. 2, 407-415.

Cohesion Technologies, Inc., "Business Summary," at <http://www.cohesiontech.com> (visited on Nov. 19, 1999) (3 pages).
Collagen Facts provided by Ajay Kumar and Biocore, Inc., 2 pages, date unknown.
Davol, Inc., *Clotting Power*: Hemostasis Products Catalog, 2 pages, website and date unknown.
Dufrane, P.et al. (1990). "Prebiopsy Localization of Non-Palpable Breast Cancer," *J. Beige De Radiologie* 73(5):401-404.
Ethicon Home Page, (1998) "Ethicon: Wound Closure," 1 page, (http://www.eosinc.com).
Freiherr, Greg. (1997). "Biotech Devices Promise Benefits in Wound Repair and Surgery," *Medical Device & Diagnostic Industry* Magazine, 6 pages. (www.devicelink.com).
Hachisu et al. (1989). "Endoscopic Clip-Marking of Lesions Using the Newly Developed HX-3L Clip," *Surgical Endoscopy* vol. 3, 142-147.
Katz, Jon and Spera, Gabriel. (1998). "Biomaterials Research Focuses on Developing New Applications," *Medical Device & Diagnostic Industry* Magazine, 8 pages (www.devicelink.com).
Lebovic, G.S. (Feb. 14-17, 2000). "Utility of a Radiolucent, Bioabsorbable Marker Following Percutaneous Excision of Breast Lesions," *University of Florida 5th Annual Multidisciplinary Breast Conference* (Poster—2 pages total).
Middleton, John and Tipton, Arthur. (1998). "Synthetic Biodegradable Polymers as Medical Devices," *Medical Plastics and Biomaterials* Magazine, 17 pages (www.devicelink.com).
Parker, Steve. "Steps in a Stereoetactic Mammotome Biopsy," Publication by *Sally Jobe* Breast Centre, pp. 1-5, date unknown.
Publication by Medical Plastics and Biomaterials, (1997), p. 61.
Publication by Surmodics, Inc., 1 page, (http://www.surmodics.com), date unknown.
RaB Biochemicals, "Structure and properties of collagen," *High Quality Biochemicals from Scientist to Scientist*, 1 page, date unknown.
Storey, Robson and Wiggins, Jeffrey. (1996). "Design and Fabrication of Polyester-Fiber and Matrix Composites for Totally Absorbable Biomaterials," *Medical Plastics and Biomaterials* Magazine, 6 pages (www.devicelink.com).
Surgicel Fibrillar: Absorbable Hemostat (Oxidized Regenerated Cellulose), "Advances Hemostasis . . . Layer by Layer," Publication by Ethicon, a Johnson & Johnson company, 6 pages, date unknown.
Trovan®: Electronic Identification Systems., "Trovan Transponders," at http://www.trovan.com/transponders.htm> (visited on Dec. 13, 1999) (7 pages).

* cited by examiner

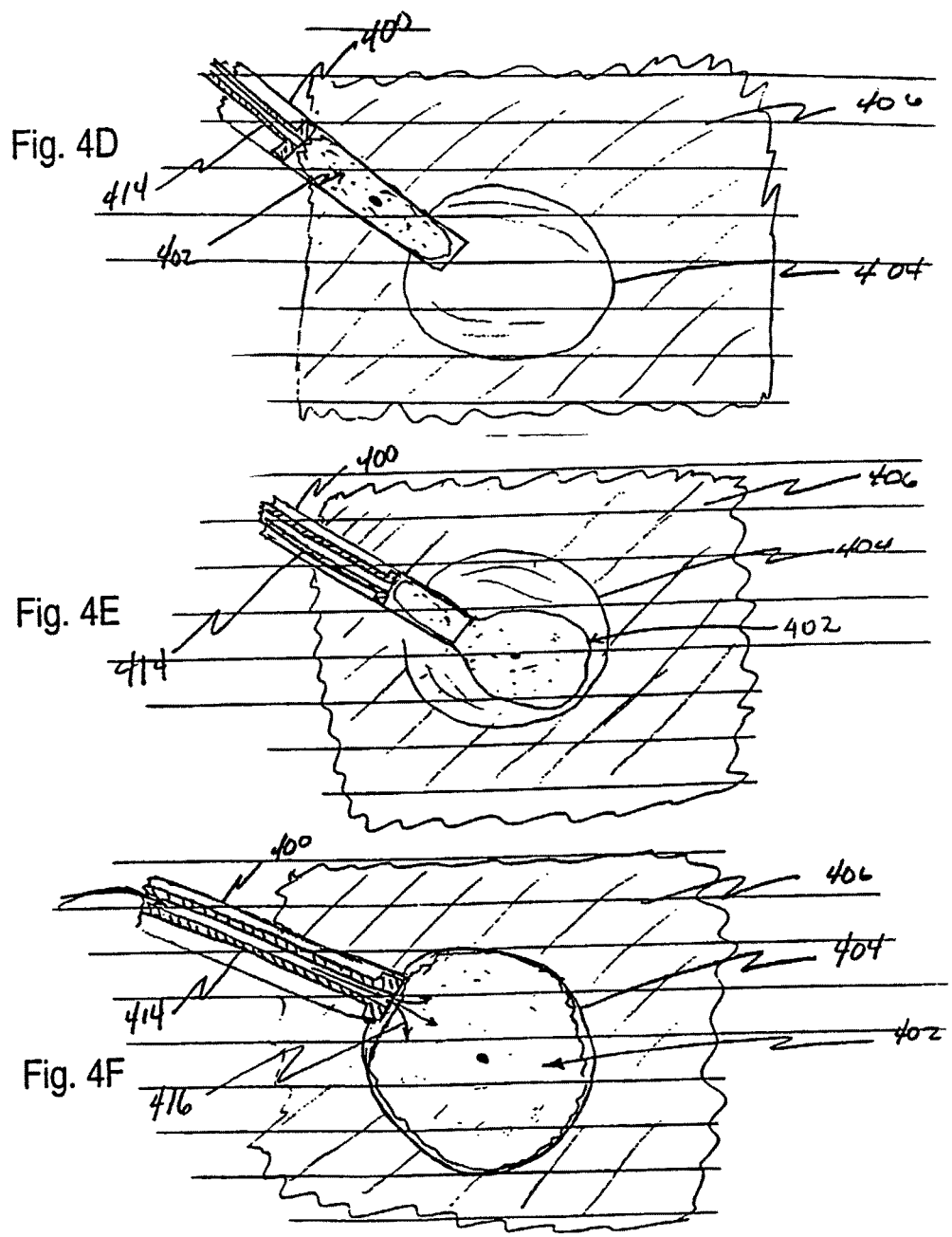

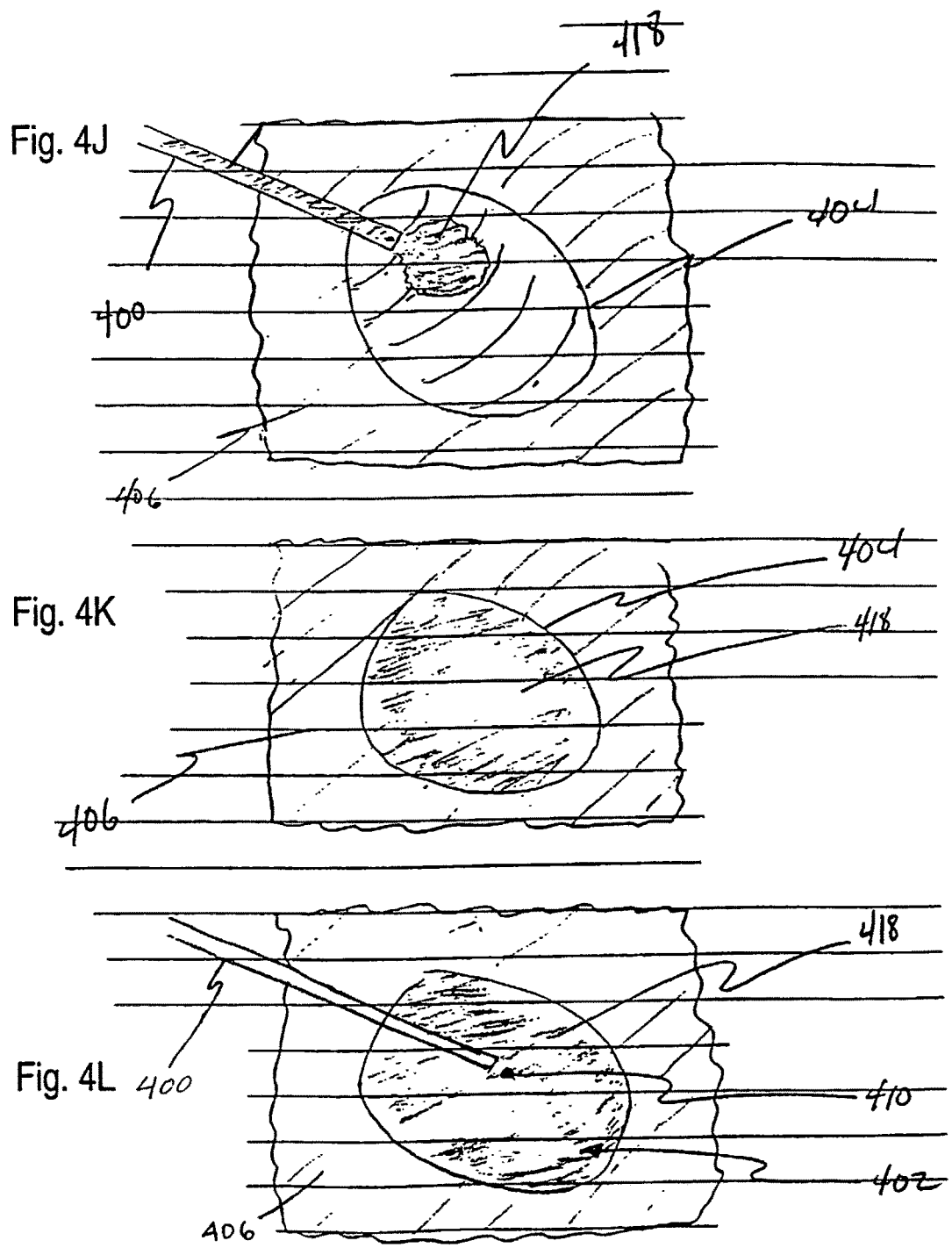

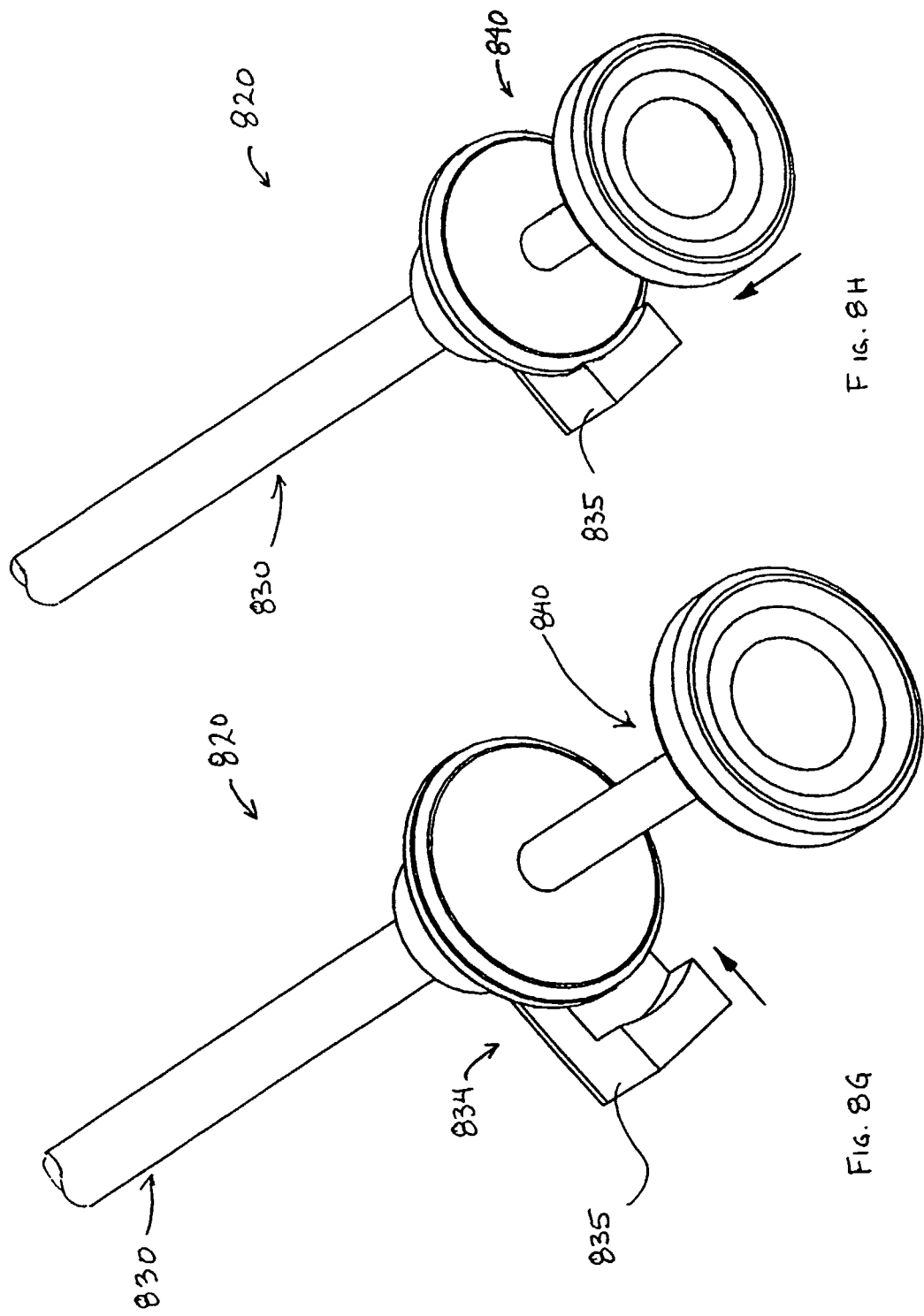

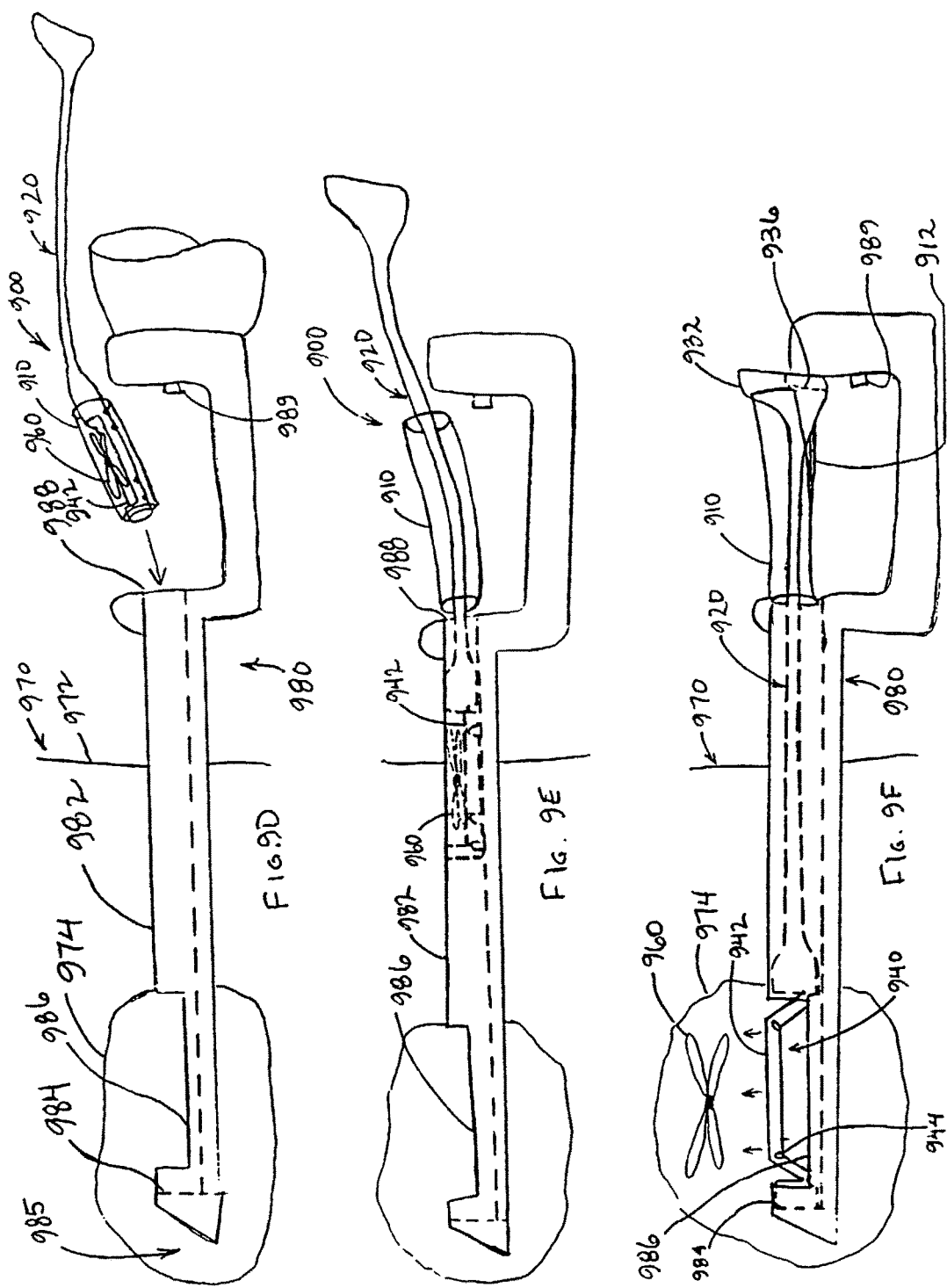

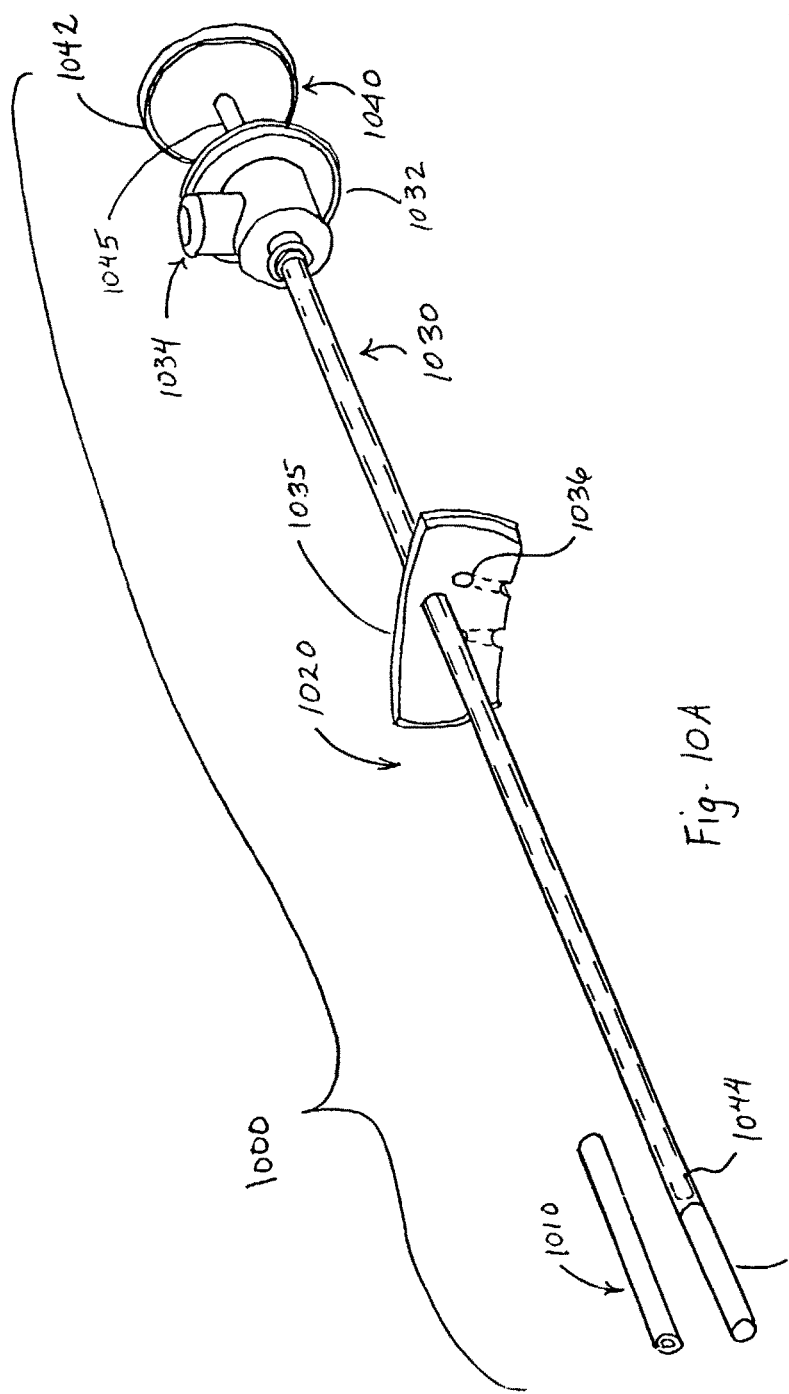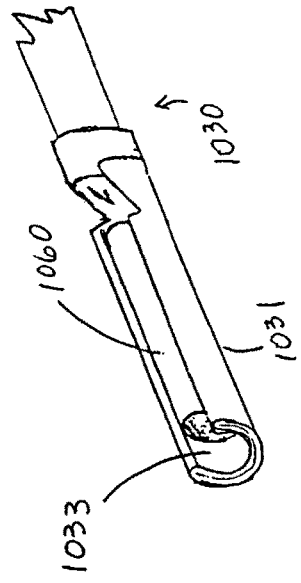
Fig. 10A
Fig. 10B

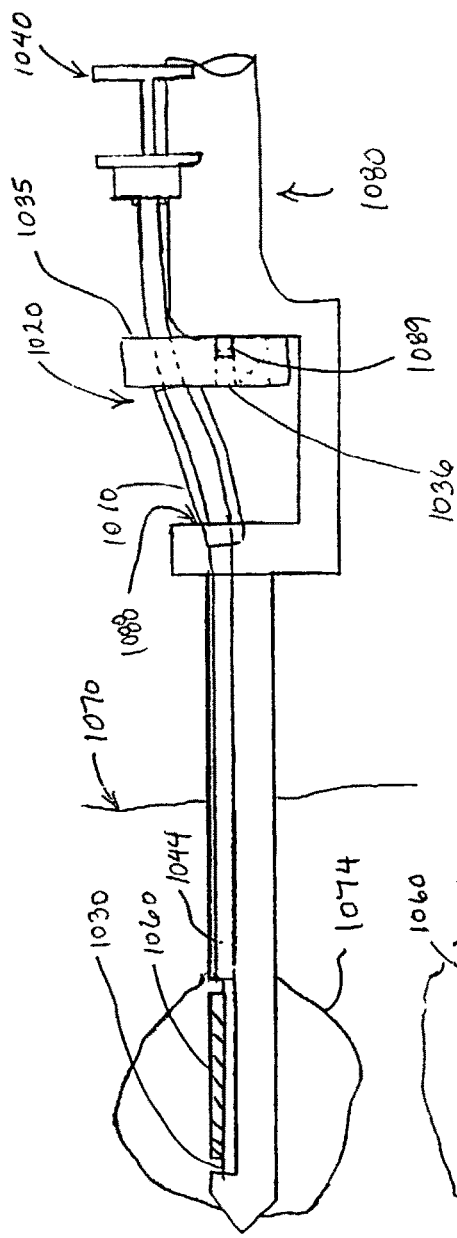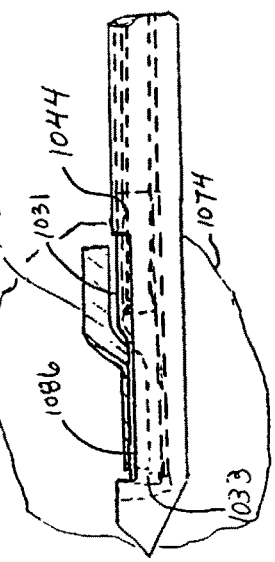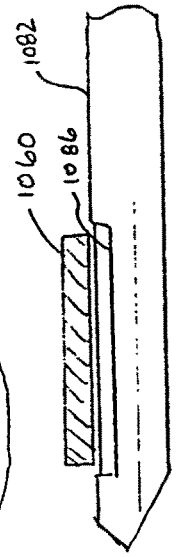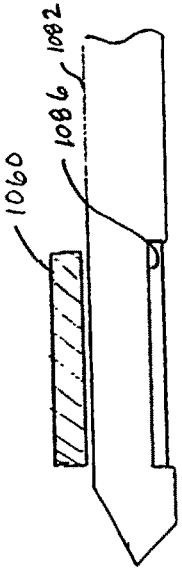

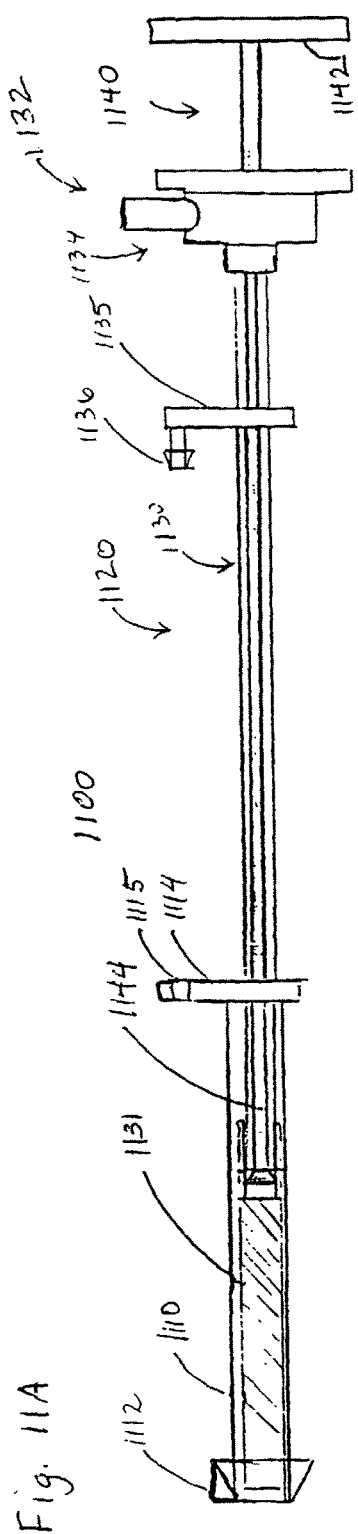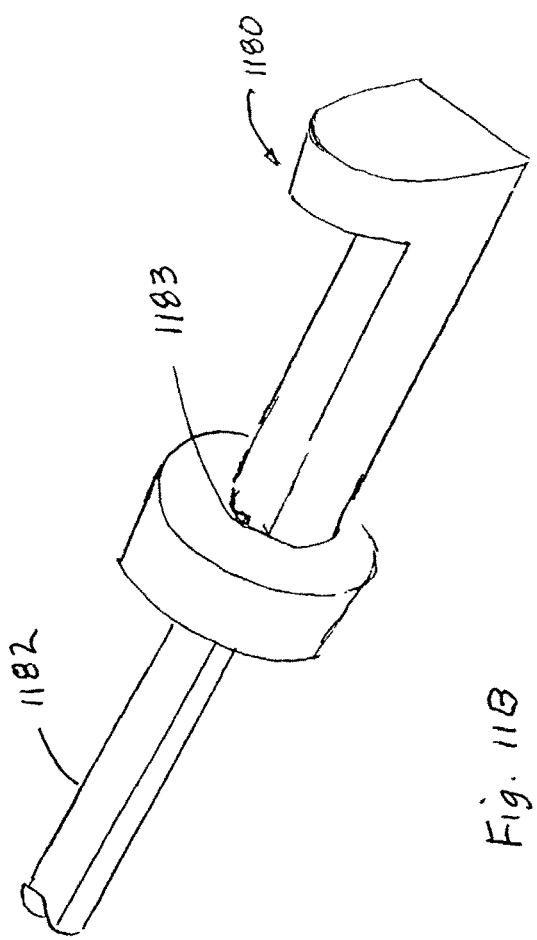
Fig. 11A
Fig. 11B

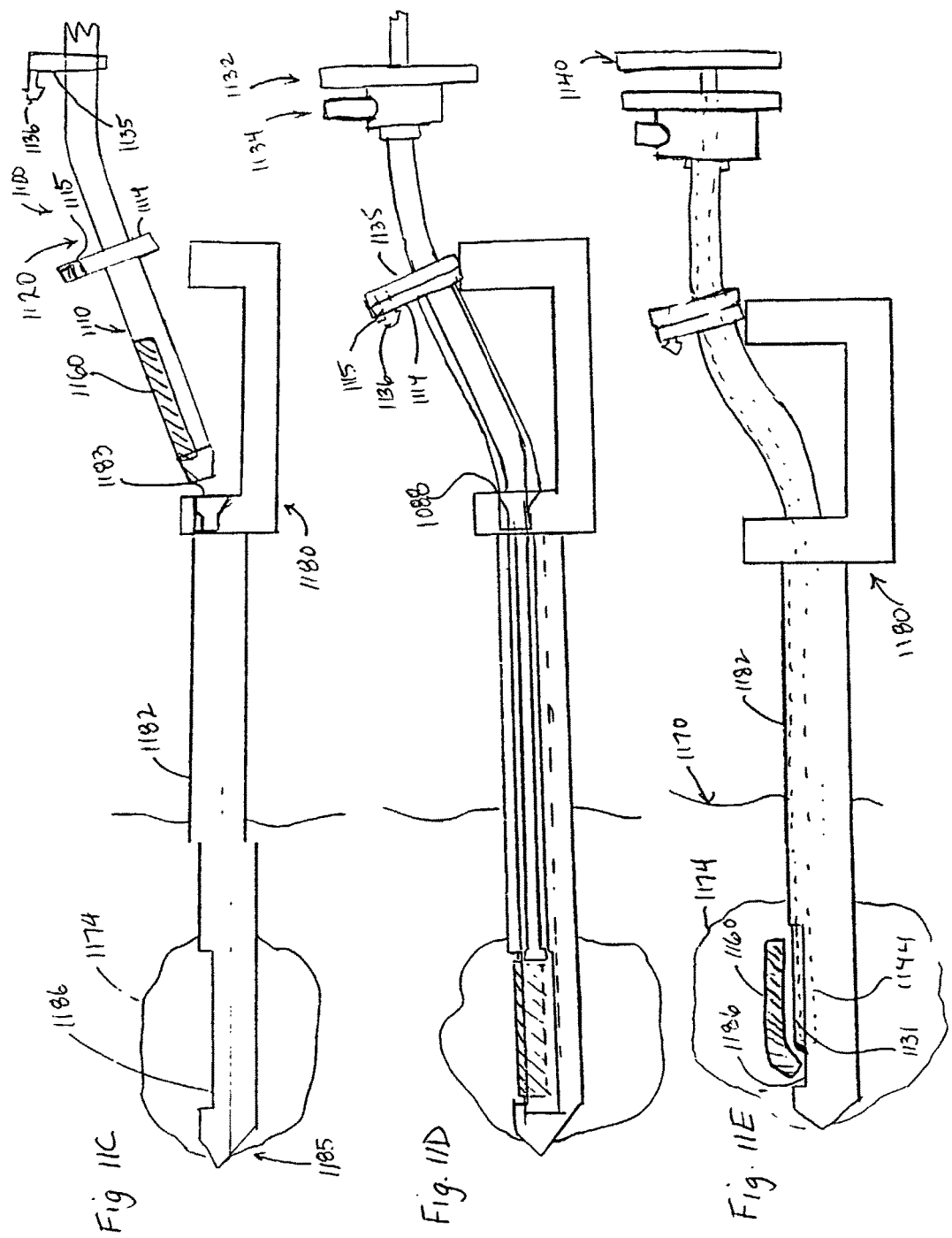

DEVICE AND METHOD FOR SAFE LOCATION AND MARKING OF A BIOPSY CAVITY

OTHER PUBLICATIONS

Alliance Pharmaceutical Corp., "Imagent® Product Summary," 5 pages, (no date) http://www.allp.com/Imagent/IM_SUM.HTM

CROSS-REFERENCE TO RELATED APPLICATION

This application is a National Stage Entry of International Patent Application No. PCT/US99/30619, filed Dec. 23, 1999, which is a continuation-in-part of U.S. Ser. No. 09/347,185, filed Jul. 2, 1999, which is a continuation-in-part of U.S. Ser. No. 09/285,329, filed Apr. 2, 1999, which is a continuation-in-part of U.S. Ser. No. 09/220,618, filed Dec. 24, 1998.

FIELD OF THE INVENTION

This invention is directed to subcutaneous cavity and sentinel node marking devices, delivery devices, and methods. More particularly, a cavity marking device, delivery device, and method are disclosed that enable one to determine the location, orientation, and periphery of the cavity by radiographic, mammographic, echographic, or other noninvasive techniques. The cavity marking device typically is made up of one or more resilient bodies and a radiopaque or echogenic marker. Also disclosed are a composition and method for noninvasively locating the sentinel lymph node in a mammalian body to determine if cancerous cells have spread thereto.

BACKGROUND OF THE INVENTION

Over 1.1 million breast biopsies are performed each year in the United States alone. Of these, about 80% of the lesions excised during biopsy are found to be benign while about 20% of these lesions are malignant.

In the field of breast cancer, stereotactically guided and percutaneous biopsy procedures have increased in frequency as well as in accuracy as modern imaging techniques allow the physician to locate lesions with ever-increasing precision. However, for any given biopsy procedure, a subsequent examination of the biopsy site is very often desirable. There is an important need to determine the location, most notably the center, as well as the orientation and periphery (margins) of the subcutaneous cavity from which the lesion is removed.

For example, in cases where the lesion is found to be benign, a visual, noninvasive follow-up examination of the biopsy site is often performed to ensure the absence of any suspect tissue and the proper healing of the cavity from which the tissue was removed. Such follow-up examination is also performed where the lesion is found to be malignant and the physician is confident that all suspect tissue was removed and the tissue in the region of the perimeter or margins of the cavity is "clean".

In some cases, however, the physician may be concerned that the initial biopsy failed to remove a sufficient amount of the lesion. Furthermore, in some percutaneous biopsy procedures, such as those using the Mammotome biopsy probe, it is very difficult to guarantee clean margins. Such a biopsied lesion is colloquially referred to as a "dirty lesion" or "having a dirty margin" and requires follow-up observation of any suspect tissue growth in the surrounding marginal area of the initial biopsy site. Thus, an excision around the original biopsy site must often be performed. In such a case, the perimeter of the cavity should preferably be identified, as the cavity may contain cancerous cells. Identification of the cavity perimeter is desirable to avoid the risk of opening the cavity, which could release and spread the cancerous cells. Moreover, the site of the re-excised procedure itself requires follow-up examination, providing further impetus for accurate identification of the location of the re-excised site. Therefore, a new marker may be placed after re-excision.

Prior methods of marking biopsy cavities utilize one or more tissue marking clips as the biopsy site-marking device. Most commonly, these marker clips have a "horseshoe" configuration. The marker clips attach to the walls of the cavity when the free ends or limbs of the "horseshoe" are pinched together, trapping the tissue. This device has significant drawbacks.

For instance, prior to placing the marker clip at the cavity site, care must be taken to remove residual tissue debris, typically by vacuum, to minimize the possibility that the marker clip attaches to any loose tissue as opposed to the cavity wall. Once the cavity is prepared, the clip must be examined to ensure that the limbs of the clip are substantially straight. If the limbs have been prematurely bent together, the clip will be discarded, as it will most likely not attach properly to the cavity wall. Actual placement of the clip often requires additional vacuum of the cavity wall to draw the wall into the aperture between the limbs of the marking clip so that a better grip is obtained between the limbs of the clip. Additionally, there is always the possibility that the clip may detach from the cavity wall during or after withdrawal of the tools used to place the clip into the cavity.

Aside from the problems inherent in the placement of the marking clip, there are also limitations associated with how well the marking clip can identify a biopsy cavity. As the marking clip must trap tissue for proper attachment, in cases of endoscopic, fluoroscopic, or blind placement, the clip can only be placed on a wall of the cavity substantially opposite to the opening of the cavity.

Moreover, patient concern limits the number of clips that may be placed in a cavity. As a result, the medical practitioner is forced to identify the outline of a three dimensional cavity by a single point as defined by the marking clip. Obviously, determination of the periphery of a biopsy cavity from one point on the periphery is not possible.

These limitations are compounded as the biopsy cavity fills within a few hours with bodily fluids, which eventually renders the cavity invisible to noninvasive techniques. Another difficulty in viewing the clip stems from the fact that the clip is attached to the side, not the center, of the cavity. This makes determining the spatial orientation and position of the cavity difficult if not impossible during follow-up examination. Additionally, during a stereotactic breast biopsy procedure, the breast is under compression when the marking clip is placed. Upon release of the compressive force, determining the location of the clip can be unpredictable, and any information once known about the orientation and location of the periphery of the cavity is lost.

The marker clip does not aid in the healing process of the biopsy wound. Complications and false information may arise if the marker strays from its original placement site. As described above, if a re-excision of the site is required, the marker clip may also interfere when excision of a target lesion is sought.

Other devices pertaining to biopsy aids are directed to assisting in the healing and closure of the biopsy wound, but they do not address the clinical need or desire of accurately preserving the location and orientation of the biopsy cavity. See, e.g., U.S. Pat. Nos. 4,347,234; 5,388,588; 5,326,350; 5,394,886; 5,467,780; 5,571,181; and 5,676,146.

In cases where a biopsy excises lesion or tumor is suspected to be cancerous, it is desirable to determine whether any cancerous cells have spread from the site of the original lesion or tumor. A sentinel node (SN) is the first lymph node to receive drainage of lymphatic fluid and cells from a tumor or malignant growth. For various cancers such as malignant melanoma and breast cancer, identification of the SN is now a standard technique for determining whether cancerous cells have migrated to a lymph gland from the site of the original lesion or tumor. Increasing data suggests that the status of the SN may predict whether other nodes in the axilla (i.e. the armpit) harbor cancerous cells. Although identification of the SN may be desirable after some biopsy procedures, there are occasions where identification of the SN is desirable even though no biopsy procedure is performed. In fact, a thorough analysis of multiple sections (0.5-mm intervals) of a sentinel node or nodes is more likely to detect hidden micrometastases than a routine single-section examination of many regional nodes, including the sentinel node, according to Jannink et al. in "Serial Sectioning of Sentinel Nodes in Patients with Breast Cancer: A Pilot Study," Annals of Surgical Oncology, 5(4):310-314.

Thus, accurately determining the location of a SN, permits removal of the SN to determine its pathology. If the SN does not contain cancerous cells, the cancer has not spread and the stage of the cancer can be determined. The ability to make this determination from an examination of the SN minimizes the number of lymph nodes removed and eliminates the need to remove additional lymph nodes. In a review in Breast Diseases: A Year Book® Quarterly Vol. 10 No. 3, of a paper by Hack et al., "Physical and Psychological Morbidity After Axillary Lymph Node Dissection for Breast Cancer," J Clin Oncol 17:143-149, 1999, Vetto states that approximately 27% of patients undergoing sentinel lymph node biopsy for early-stage breast cancer still require axillary lymph node dissection (ALND) due to the existence of a positive node. Accordingly, the remaining 63% of the patients could benefit by an SN biopsy and avoid having radical dissection.

Previously, it was impossible to locate the sentinel node without performing ALND. In the case of breast cancer, determining whether the cancerous cells migrated involved removal of all axillary lymph nodes. This required radical surgery. This painful option often lead to complications that resulted in significant morbidity and even mortality. As discussed by Hack et al., pain and discomfort after ALND significantly corresponded to quality of life after the procedure. According to Hack et al., patients with more than 13 lymph nodes dissected reported more pain than women with fewer lymph nodes dissected.

More recently, a technique known as "sentinel node biopsy" allowed for accurate mapping of a SN's location by the use of blue dye and a radioactive tracer, separately or in combination. Typically, a dye and/or a radioactive tracer are injected around the location of a tumor, into the biopsy cavity or tumor cavity (if the tumor was partially or completely removed), or "subdermally" into the parenchymal tissue anterior to the tumor. This latter technique is described by De Cicco et al. (1999) in "Lymphoscintigraphy and Radioguided Biopsy of the Sentinel Axillary Node in Breast Cancer," J Nucl Med 39:2080-2084, 1998, and in a review of that article by Haigh et al. (1999) in Breast Diseases: A Year Book® Quarterly, Vol. 10 No 3. The dye migrates from the tumor site through the lymphatic channels to the regional lymph nodes that serve the cancerous tissue. The SN, which is the node most likely to be involved with cancer, is identified through surgery and removed for pathologic analysis. When a radioactive tracer is used, a gamma probe or like-device is used to further assist a physician in identifying the site of the SN.

Unfortunately, visualization of the blue dye depends upon the surgeon localizing it, and no preoperative assessment of mapping is possible. Therefore, the surgeon must first make an incision in the general vicinity of the lymph nodes, then dissect around the area to locate the blue dye. Another complication arises as the dye may cause an allergic reaction in some individuals. This reaction may leave a mark on the skin similar to a 'tattoo.'

Using a radioactive tracer, alone or in combination with blue dye, to locate the SN also has some disadvantages. It is an interdisciplinary process, requiring nuclear medicine personnel, adherence to radiation safety regulations, preparation of the radiocolloid, and gamma detection instrumentation. Furthermore, the safety of this procedure is questionable. See e.g., Miner et al. (1999). "Guidelines for the Safe Use of Radioactive Materials During Localization and Resection of the Sentinel Lymph Node," Ann Surg Oncol 6:75-82.

In the case of a lumpectomy, when the lesion is known to be cancerous, locating the SN is desirable so that the SN is removed in the same procedure as the lumpectomy. In fact, even if the pathology of the lesion is not yet known, there are reasons for initiating the SN localization during a breast biopsy procedure, as discussed below.

Previously, imaging techniques, such as ultrasound, MRI, and CT, attempted to non-invasively find and diagnose cancerous lymph nodes prior to removing them. However, according to Schlag. (1998). "The 'Sentinel Node' Concept: More Questions Raised than Answers Provided?" Oncologist 1998; 3(5):VI-VII, general criteria such as size, shape, structure, or texture in the various imaging modalities are unreliable, and these techniques result in low sensitivity and/or low specificity. As described by Veronesi et al. (1997). "Sentinel-node biopsy to avoid axillary dissection in breast cancer with clinically negative lymph-nodes," Lancet June 28; 349(9069):1864-7, in 32 (38%) of 85 patients with metastatic axillary nodes, the only positive node was the sentinel node. Accordingly, if all of the nodes were checked by imaging instead of locating and biopsying the SN, the chances of missing the cancer would likely have been much higher. Furthermore, because of usually low specificity, these techniques require surgical excision and examination of multiple lymph nodes, many of which may contain no cancer. In contrast, by identifying only one or a few SN's, without trying to make any diagnosis of cancer prior to tissue removal, the excision is much less extensive, yielding a smaller tissue sample. Also, the histological examination of one or a few SN's can be more thorough than the case where many lymph nodes require examination.

Therefore, one objective of the invention described herein is to provide a marking device, delivery device, and method that enable noninvasive determination of cavity location, orientation, and periphery.

Another objective of is to provide an atraumatic marking device that does not rely on pinching or piercing tissue.

Another objective is to provide a method of delivering through a small opening a marking device for marking the borders of a cavity.

Another objective is to provide a composition and method for localizing and marking a sentinel node.

Another objective is to provide a composition capable of (1) deposition in or around a lesion and migration to and accumulation in the associated sentinel node, and (2) non-invasive detection.

Another objective is to provide a method for remotely detecting the location of a sentinel node with a minimum of trauma and toxicity to the patient.

Yet another objective is to provide a composition and method for both marking a lesion cavity and locating the sentinel node in the same procedure.

SUMMARY OF THE INVENTION

This invention relates to devices and procedures for percutaneously marking a biopsy or lumpectomy cavity. In particular, the inventive device is a biopsy cavity marking body made of a resilient, preferably bioabsorbable material having at least one preferably radiopaque or echogenic marker. The device may take on a variety of shapes and sizes tailored for the specific biopsy cavity to be filled. For example, the device in its simplest form is a spherical or cylindrical collagen sponge having a single radiopaque or echogenic marker located in its geometric center. Alternatively, the body may have multiple components linked together with multiple radiopaque or echogenic markers.

A further aspect of the invention allows the marker or the body, singly or in combination, to be constructed to have a varying rate of degradation or bioabsorption. For instance, the body may be constructed to have a layer of bioabsorbable material as an outer "shell." Accordingly, prior to degradation of the shell, the body is palpable. Upon degradation of the shell, the remainder of the body would degrade at an accelerated rate in comparison to the outer shell.

The marking device may additionally contain a variety of drugs, such as hemostatic agents, pain-killing substances, or even healing or therapeutic agents that may be delivered directly to the biopsy cavity. Furthermore, the material and configuration of the sponge itself may be hemostatic. Importantly, the device is capable of accurately marking a specific location, such as the center, of the biopsy cavity, and providing other information about the patient or the particular biopsy or device deployed.

The marking device is preferably, although not necessarily, delivered immediately after removal of the tissue specimen using the same medical instrument used to remove the tissue specimen itself. Such medical instruments are described in U.S. Pat. Nos. 5,111,828; 5,197,484; 5,353,804; 5,511,566; 5,546,957; 5,560,373; 5,817,033; pending U.S. patent application Ser. No. 09/145,487, filed Sep. 1, 1998 and entitled "PERCUTANEOUS TISSUE REMOVAL DEVICE"; and pending U.S. patent application Ser. No. 09/184,766, filed Nov. 2, 1998 and entitled "EXPANDABLE RING PERCUTANEOUS TISSUE REMOVAL DEVICE". The marking device is compressed and loaded into the delivery device and percutaneously advanced to the biopsy site where, upon exiting from the delivery device, it expands to substantially fill the cavity from the biopsy. The physician may then use follow-up noninvasive detection techniques, such as x-ray mammography or ultrasound, to identify, locate, and monitor the biopsy cavity site over a period of time.

The marking device is usually inserted into the patient's body either surgically via an opening into the body cavity, or using a minimally invasive procedure employing such medical instruments as a catheter, introducer, biopsy probe, or similar device, or a specially-designed delivery device used alone or in conjunction with a catheter, introducer, biopsy probe, or similar device. When inserted via the minimally invasive procedure, the resiliency of the body allows the marking device to be compressed upon placement in a delivery device. Upon insertion of the cavity marking device into the cavity, the resiliency of the body causes the cavity marking device to self-expand, substantially filling the cavity. Following expansion, the marking device volume following expansion preferably is 3 to 30 times its compressed volume, and more preferably 5 to 22 times, and most preferably about 10 times. The resiliency of the body can be further predetermined so that the body is palpable, thus allowing tactile location by a surgeon in subsequent follow-up examinations. Typically, the filler body is required to be palpable for approximately 3 months. However, this period may be increased or decreased as needed.

The expansion of the resilient body can be aided by the addition of a biocompatible fluid, which is absorbed into the body. For instance, the fluid can be a saline solution, a painkilling substance, a healing agent, a therapeutic fluid, or any combination of such fluids. The fluid or combination of fluids may be added to and absorbed by the body of the device before or after deployment of the device into a cavity. For example, the body of the marking device may be presoaked with the fluid and then delivered into the cavity. In this instance, the fluid aids the expansion of the body of the device upon deployment. Another example is provided as the device is delivered into the cavity without being presoaked. In such a case, fluid is delivered into the cavity after the body of the device is deployed into the cavity. Upon delivery of the fluid, the body of the device soaks up the fluid, thereby aiding the expansion of the cavity marking device as it expands to fit the cavity. The fluid may be, but is not limited to being, delivered by the access device. Furthermore, expansion of the body of the marking device may be aided by body fluids, such as the fluid component of blood, already present in the cavity.

By "biocompatible fluid" what is meant is a liquid, solution, or suspension that may contain inorganic or organic material. For instance, the biocompatible fluid is preferably saline solution, but may be water or contain adjuvants such as medications to prevent infection, reduce pain, or the like. Alternatively or additionally, the fluid may be used to mark the sentinel lymph node, as will be described later. Obviously, the liquid is intended to be a type that does no harm to the body.

After placement of the cavity marking device into the cavity, the bioabsorbable body degrades at a predetermined rate. As the body of the cavity marking device is absorbed, tissue is substituted for the bioabsorbable material. Moreover, while the body degrades, the marker, which is usually suspended substantially in the volumetric center of the body of the device, is left in the center of the cavity. Thus, during a subsequent examination, a medical practitioner having knowledge of the dimensions of the body of the cavity marking device can determine the location as well as the periphery of the biopsy cavity. The orientation of the cavity is self-evident as the marker is left in substantially the center of the cavity. For the case where multiple markers are used, the markers are usually placed in a manner showing directionality.

The body, marker, or radiopaque or echogenic coatings can be made to degrade in situ and be absorbed into the patient's body over a predetermined period of time. It is generally preferred that if the marker's radiopacity or echogenicity is chosen to degrade over time, such degradation does not take place within at least one year after implantation of the inventive device. In this way, if a new lump or calcification (in the case of a breast biopsy) is discovered after the biopsy, such a marker will allow the physician to know the relation of such new growth in relation to the region of excised tissue. On the other hand, and as discussed below, a bioabsorption period of three months is preferred for any such coatings on the perimeter of the body itself.

Another variation of the invention is that the body of the marking device is formed from a bioabsorbable thread-like surgical material, for example a suture material. Preferably, the surgical material is resilient. In this variation the surgical material is looped through a marker. The marking device may have any number of loops or any number of opposing pairs of loops. Another variation of the marking device includes an opposing member on each loop. For example, a loop could be folded to form the opposing member.

This invention further includes the act of filling the biopsy cavity with a bioabsorbable liquid, aerosol or gelatinous material, preferably gelatinous collagen, allowing the material to partially solidify or gel and then placing a marker, which may have a configuration as described above, into the center of the bioabsorbable material. The gel may also be made radiopaque or echogenic by the addition of radiopaque or echogenic materials, such as powdered tantalum, tungsten, barium carbonate, bismuth oxide, barium sulfate or other barium- or bismuth-containing compounds.

This method may be combined with any aspect of the previously described devices as needed. For instance, one could insert a hemostatic or pain-killing substance as described above into the biopsy cavity along with the bioabsorbable material. Alternatively, a bioabsorbable marker could be inserted into a predetermined location, such as the center, of the body of bioabsorbable material.

It is within the scope of this invention that either or both of the marker or markers and the bioabsorbable body may be radioactive, especially if a regimen of treatment using radioactivity is contemplated.

This procedure may be used in any internal, preferably soft, tissue, but is most useful in breast tissue, lung tissue, prostate tissue, or lymph gland tissue. Obviously, though, treatment and diagnosis of breast tissue problems forms the central theme of the invention.

In contrast to the marker clips as described above, the cavity marking device has the obvious advantage of marking the geometric center of a biopsy cavity. Also, unlike the marking clip which has the potential of attaching to loose tissue and moving after initial placement, the marking device self-expands upon insertion into the cavity, thus providing resistance against the walls of the cavity thereby anchoring itself within the cavity. The marking device may be configured to be substantially smaller, larger, or equal to the size of the cavity; however, in some cases the marking device will be configured to be larger than the cavity. This aspect of the biopsy site-marking device provides a cosmetic benefit to the patient, especially when the biopsy is taken from the breast. For example, the resistance provided by the cavity marking device against the walls of the cavity may minimize any "dimpling" effect observed in the skin when large pieces of tissue are removed, as, for example, during excisional biopsies. The marking device may be configured to allow tissue ingrowth, being replaced by tissue as it is absorbed into the patient's body.

The invention further includes a delivery device and method for placement of a marking device. For example, the invention includes a sheath capable of being placed in contact with a cavity, a cartridge or applicator in which a marking device may be placed, and a disengaging arm onto which the cartridge is mounted. The marking device will preferably have a frictional fit with the cartridge. Preferably, the sheath is placed in contact with the cavity, for example, simultaneously with the biopsy device or soon after the biopsy device obtains a sample. The sheath may be placed at a point of entrance of the cavity or it may be partially inserted into the cavity. The delivery device cartridge and engaging arm are then inserted into the sheath and advanced into the cavity until a portion of the cartridge containing the marking device is positioned within the cavity but a portion of the cartridge is still within the sheath. Next, the delivery device cartridge is retracted while the disengaging arm prevents the marking device from being retracted from the cavity. Thus, the marking device remains in the cavity and radially expands to substantially fill the cavity. Hence, the marking device is delivered and expands in the cavity without a need for simultaneously pushing the marking device into the cavity. Another aspect of this invention is that the frictional fit between a marking device and a cartridge may be sufficiently increased to minimize premature placement of the marking device into the cavity.

Other delivery devices and methods for using them are disclosed, including a "sheath-over-probe" device and method and "through-cannula" devices and methods. These devices and methods are well suited to apply the marking device having a body comprising absorbable suture or collagen and described herein, but could be used with any of the marking devices in the present application.

The "sheath-over-probe" device includes a sheath that slides over a probe, such as a biopsy probe. It is well suited for use with the Mammotome® 11 GA Probe (now owned by Johnson & Johnson) but may be sized to fit other commercially available biopsy devices. The sheath is introduced into the body along with the probe. After obtaining a biopsy sample, the probe is removed, leaving the sheath in place. The marking device is then delivered through the sheath.

The "through-cannula" device is intended for insertion through the cannula portion of a biopsy device; it, too, is well suited for the Mammotome® 11 GA Probe but may be sized to fit other commercially available biopsy devices.

Although the subcutaneous cavity marking device and methods described above are suited for percutaneous placement of the marker within a biopsy cavity it is not intended that the invention is limited to such placement. The device and method are also appropriate for intraoperative or surgical placement of the marker within a biopsy cavity.

The present invention also provides an alternative method to remotely detect sentinel nodes (SN). This method includes the deposit, preferably by injection via a thin needle applicator or using a marker delivery device described herein, of a remotely detectable contrast agent that will migrate to the SN, allowing the exact location of the SN to be pinpointed and targeted for removal using minimally invasive techniques. This method eliminates the need for potentially toxic radioactive tracer material. In addition, the lack of toxicity of such agents obviates the need to remove the lesion and/or the SN on the same day.

These agents may be any biologically compatible agents capable of remote detection. Examples of such remote detection include, but are not limited to magnetism such as a magnetometer, Hall effect sensor, or magnetic resonance imaging (MRI); ultrasound; thermal means; high intensity ultraviolet techniques; fluorescent dye techniques; singly or in combination.

One example of such a contrast agent is an echogenic microsphere capable of reflecting ultrasonic energy. These microspheres, which average typically between 0.2 microns and 5 microns in diameter, may be mixed with a biologically compatible carrier-fluid and injected into the body in the vicinity of the lesion. Upon an exposure to ultrasonic energy, the spheres reflect the energy creating an ultrasonic reflection. The ultrasonic reflection resulting from a large number of the microspheres that have accumulated in the SN permits detection of the particular node by a conventional ultrasonic probe. Such microspheres are available at various pharmaceutical companies such as Acusphere, Sonus, and Alliance Pharmaceutical Corp.

Another example of a detectable agent is a biologically compatible magnetically detectable body such as a magnetic microsphere. Such a magnetically detectable body can be the echogenic microsphere described above that is either fabricated from or coated with a magnetic material. Alternatively, the magnetically detectable body may be a solid or other type of magnetic body capable of being incorporated into a carrier fluid and deposited around the lesion or its cavity as described above. These bodies are preferably capable of migration to and accumulation in the SN so that, in a similar fashion to the echogenic microspheres, the cumulative magnetic field produced by these magnetic bodies allows for location of the SN by remote and noninvasive means.

Yet another such contrast agent is a radiopaque fluid or suspension containing radiopaque particles, detectable using X ray, fluoroscopy, or computed tomography (CT). Again, this contrast agent is preferably capable of migration to and accumulation in the SN to enable one to noninvasively determine the location of the SN.

BRIEF DESCRIPTION OF THE DRAWINGS

FIG. 1A illustrates a tissue cavity marking device with a spherical body and a single centrally located marker.

FIG. 1B shows a tissue cavity marking device with a cylindrical body and two ring-shaped markers aligned near the cylinder's longitudinal axis.

FIG. 1C shows another tissue cavity marking device with a multifaced or irregular body and a single centrally located marker.

FIG. 1D illustrates a tissue cavity marking device with a body having pores.

FIG. 1E is a partial cross-sectional view of FIG. 1D.

FIG. 1F illustrates a tissue cavity marking device with a body having an outer shell of a bioabsorbable material.

FIGS. 1G-1J illustrate various configurations of the device having a body comprising suture-type material.

FIG. 1G illustrates a tissue cavity marking device with a number of loops.

FIG. 1H illustrates a tissue cavity marking device with a pair of opposing loops.

FIG. 1I illustrates a tissue cavity marking device with two pairs of opposing loops.

FIG. 1J illustrates a tissue cavity marking device having a pair of opposing loops where the loops are longitudinally folded forming opposing members.

FIG. 1K illustrates a tissue cavity marking device with two pairs of opposing loops where each loop is longitudinally folded forming opposing members.

FIGS. 1L and 1M illustrate tissue cavity marking devices having an elongated body having circular or rectangular cross section and a metallic marker band oriented with its axis perpendicular to the long axis of the body.

FIGS. 4D-4F illustrate a method of marking a biopsy tissue cavity with the device of the present invention wherein a biocompatible fluid is delivered to the cavity marking device after placement.

FIGS. 4J-4L illustrate a method of marking a biopsy tissue cavity with the device of the present invention wherein the body material of the marking device is deposited into the biopsy cavity prior to the placement of the marker within the biopsy device.

FIGS. 8A-8I illustrate a variation of a delivery device and a method for using it to deliver a marking device to a tissue cavity made by the probe of a medical instrument.

FIGS. 9A-9F illustrate a variation of a delivery device and a method for using it to deliver a marking device to a tissue cavity through the cannula of a medical instrument.

FIGS. 10A-10H illustrate another variation of a delivery device and method for using it to deliver a marking device to a tissue cavity through the cannula of a medical instrument.

FIGS. 11A-11E illustrate another variation of a delivery device and method for using it to deliver a marking device to a tissue cavity through the cannula of a medical instrument.

DETAILED DESCRIPTION OF THE INVENTION

Figure 1A:
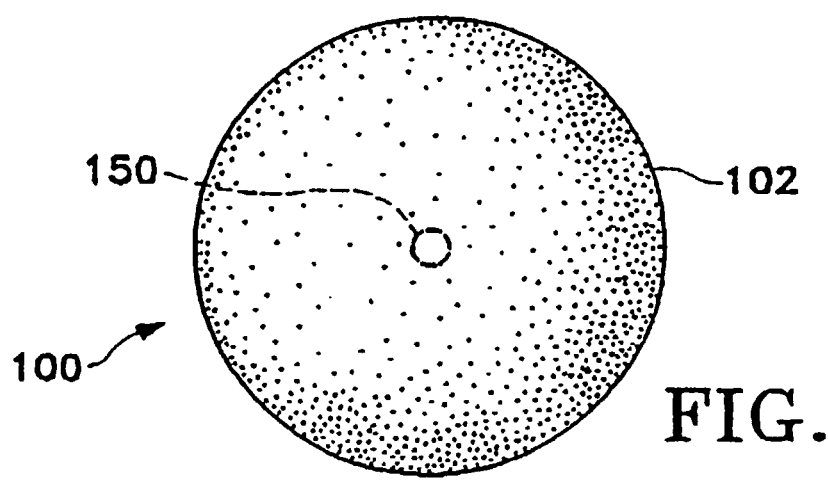
FIGS. 1A-1M illustrate various configurations of the device.

The following illustrations are examples of the invention described herein. It is contemplated that combinations of aspects of specific embodiments or combinations of the specific embodiments themselves are within the scope of this disclosure.

FIGS. 1A-1M show various configurations of a preferred subcutaneous cavity marking device of the present invention. Here the marking device 100 is displayed as having either a generally spherical body 102 (FIG. 1A), a generally cylindrical body 104 (FIG. 1B), or a multi-faced or irregular body 106 (FIG. 1C). In general, it is within the scope of this invention for the body to assume a variety of shapes. For example, the body may be constructed to have substantially curved surfaces, such as the preferred spherical 102 and cylindrical 104 bodies of FIGS. 1A and 1B, respectively. The body may have conical or ellipsoidal, etc. shapes as well. It is further within the scope of this invention for the body to have substantially planar surfaces, such as polyhedric (i.e. cubic, tetrahedral, etc.) or prismatic, etc. forms. Finally, the body may also have an irregular or random shape, in the case of a gel, combining features of various curved and planar surfaces. Body 106 of FIG. 1C is an example of such an irregular body shape. The particular body shape will be chosen to best match to the biopsy cavity in which the device is placed. However, it is also contemplated that the body shape can be chosen to be considerably larger than the cavity. Therefore, expansion of the device will provide a significant resistance against the walls of the cavity. Moreover, the aspect ratio of the device is not limited to what is displayed in the figures. For example, the cylindrical body 104 may have a shorter or longer length as required.

Figure 1B:
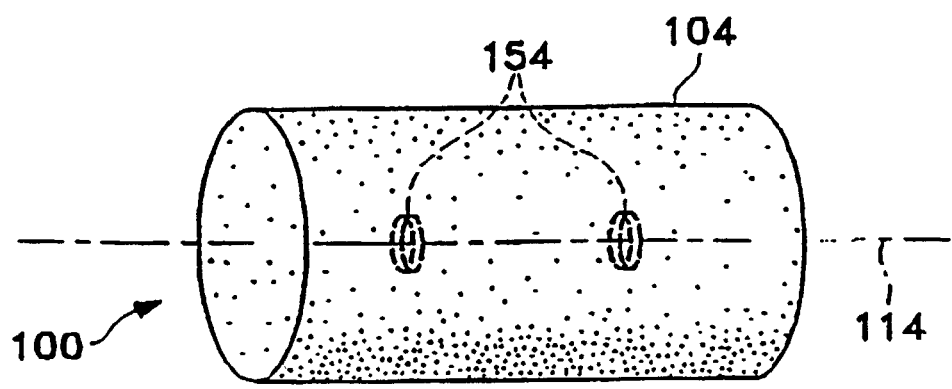
Figure 1C:
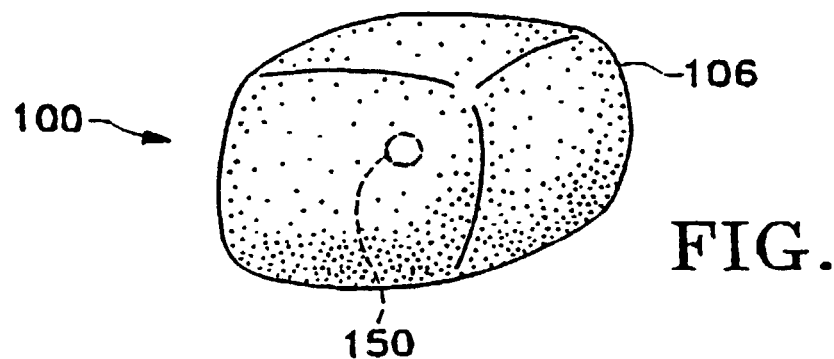

In the bodies of FIGS. 1A and 1C, the generally spherical marker 150 is located at or near the geometric center of the body. Such a configuration will aid the physician in determining the exact location of the biopsy cavity, even after the body degrades and is absorbed into the human or mammalian body.

The ring-shaped markers 154 of FIG. 1B are generally aligned along the longitudinal axis 114 of body 104. Note that although the ring-shaped markers 154 are spatially oriented so that their longitudinal axes lie along the longitudinal axis 114 of the body 104, each marker may assume a wide variety of random or predetermined spatial orientations other than the aligned orientation seen in FIG. 1C. It can be appreciated that a nonspherical marker such as marker 154 is useful in aiding a physician in determining the spatial orientation of the deployed inventive device.

Obviously, markers 150 and 154 may reside in locations other than those demonstrated in FIGS. 1A-1C. It is, however, preferred that markers 150 and 154 dwell in a predetermined, preferably central, location and orientation in the device body so to aid the physician in determining the location and orientation of the biopsy cavity. The markers herein described may be affixed to the interior or on the surface of the body by any number of suitable methods. For instance, the marker may be merely suspended in the interior of the body (especially in the case where the body is a gel), it may be woven into the body (especially in the case where the marker is a wire or suture), it may be press fit onto the body (especially in the case where the marker is a ring or band), or it may affixed to the body by a biocompatible adhesive. Any suitable means to affix or suspend the marker into the body in the preferred location is within the scope of the present invention.

Figure 1D:
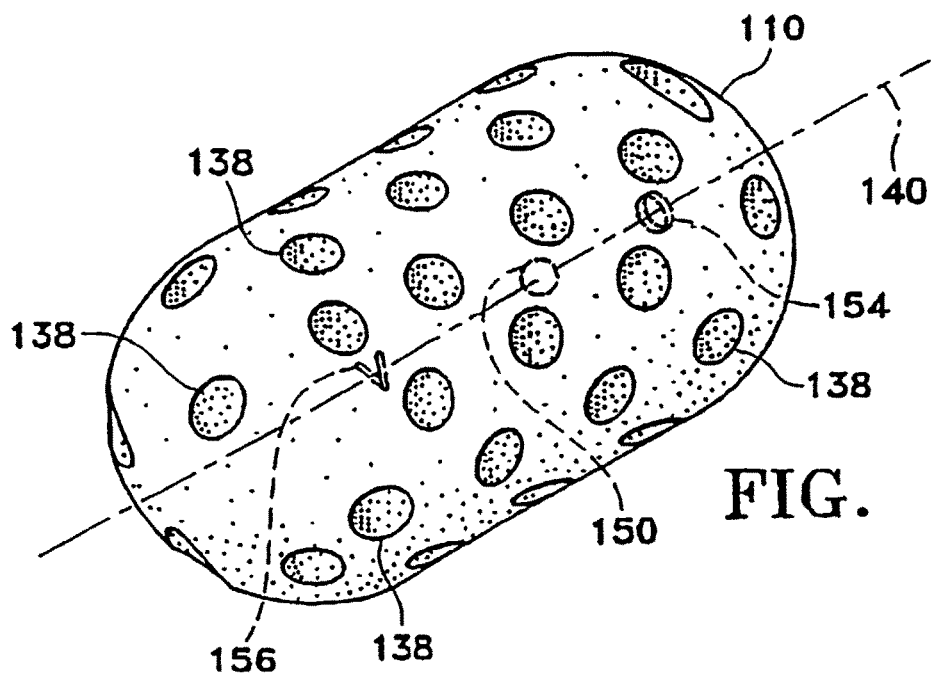
Figure 1E:
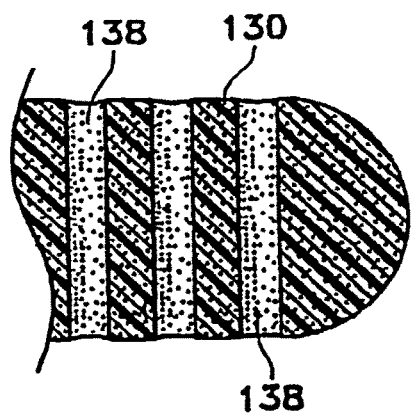

Tissue regrowth in a particular orientation can also be promoted by a body design shown in FIG. 1D. Here, body 110 contains a number of pores 138 through which tissue may grow. The pores may also be aligned in a substantially parallel fashion, traversing the thickness of the body so that tissue may regrow from one side of the body through to the other side. This is demonstrated in inset FIG. 1E, which shows a portion 130 of FIG. 1D in partial longitudinal cross section, complete with pores 138 traversing through the thickness of portion 130. Such pores 138 can be parallel to each other as shown in FIG. 1E, or they may be perpendicularly, radially, or even randomly oriented in the device body.

A trio of markers is also shown in FIG. 1D evenly aligned along the body longitudinal axis 140. Barb marker 156, spherical marker 150, and ring-shaped marker 154 demonstrate the use of different multiple markers in a single body 110. As previously described, such a design helps a physician to determine the spatial orientation of the inventive device when it is deployed in a biopsy cavity. Although the barb marker 156 is illustrated in a 'V' configuration, it is an important aspect of the barb marker 156 to have a shape that is clearly not spherical. This allows the barb marker 156 to be easily distinguished from calcifications that may be observed during any noninvasive imaging techniques.

Figure 1F:
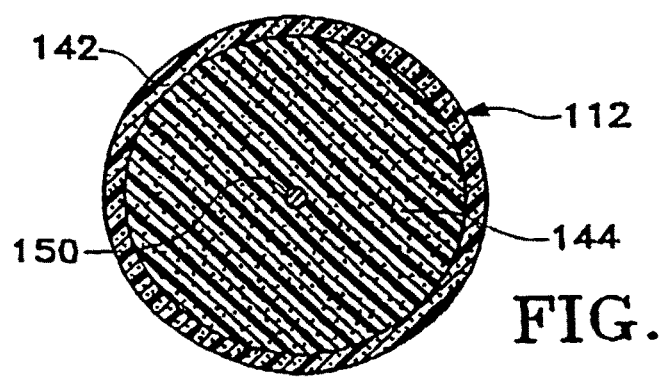

FIG. 1F depicts a further embodiment of the present invention in which body 112 is enveloped in an outer shell 142 consisting of a layer of bioabsorbable material such those mentioned above. This configuration allows the perimeter of the biopsy cavity to be marked to avoid exposing the cavity, in the case of a "dirty" margin where re-excision may be necessary, to remaining cancerous cells as the tissue begins to re-grow into the cavity. Such a shell 142 can be radiopaque and/or echogenic in situ, or it may be augmented with an additional coating of an echogenic and/or radiopaque material. The shell 142 can also be made to be palpable so that the physician or patient can be further aided in determining the location and integrity of the implanted inventive device.

Shell 142 may be designed to have a varying bioabsorption rate depending upon the thickness and type of material making up the shell 142. In general, the shell can be designed to degrade over a period ranging from as long as a year or more to as little as several months, weeks, or even days. It is preferred that such a bioabsorbable shell be designed to degrade between two and six months; especially preferred is three months. In the design of FIG. 1F, interior 144 of body 112 may be a cross-linked, collagenous material that is readily absorbed by the human or mammalian body once the shell 142 degrades. Interior 144 may be filled with a solid or gelatinous material that can be optionally made radiopaque by any number of techniques herein described.

As will be described in additional detail with respect to FIGS. 2A-2F, marker 150 in the device shown in FIG. 1F may be permanently radiopaque or echogenic, or it may be bioabsorbable and optionally coated with a radiopaque and/or echogenic coating that degrades over a predetermined period of time. It is clinically important that the marker remain detectable for at least about one to five years so that the physician may follow the patient to ensure the health of the tissue in the vicinity of the biopsy cavity. Especially preferable is a marker whose radiopacity or echogenicity lasts between about one and three years.

Each of the bodies depicted in FIGS. 1A-1F may be made from a wide variety of solid, liquid, aerosol-spray, powder, spongy, or expanding gelatinous bioabsorbable materials such as collagen, cross-linked collagen, regenerated cellulose, synthetic polymers, synthetic proteins, and combinations thereof. Also contemplated is a body made from a fibrin-collagen matrix, which further prevents unnecessary bleeding, and minimizes the possibility of hematoma formation.

Examples of synthetic bioabsorbable polymers that may be used for the body of the device are polyglycolide, or polyglycolic acid (PGA), polylactide, or polylactic acid (PLA), poly ϵ-caprolactone, polydioxanone, polylactide-co-glycolide, block or random copolymers of PGA and PLA, and other commercial bioabsorbable medical polymers. Preferred is spongy collagen or cellulose. As mentioned above, materials such as hemostatic and pain-killing substances may be incorporated into the body and marker of the cavity marking device. The use of hemostasis-promoting agents provides an obvious benefit, as the device not only marks the site of the biopsy cavity but aids in healing the cavity as well. Furthermore, such agents help to avoid hematomas. These hemostatic agents may include AVITENE Microfibrillar Collagen Hemostat; ACTIFOAM collagen sponge, sold by C. R. Bard Inc.; GELFOAM Sterile Powder or Sponge, manufactured by The Upjohn Company (Michigan); SURGICEL Fibrillar from Ethicon Endosurgery, Inc.; TISSEEL VH, a surgical fibrin sealant sold by Baxter Healthcare Corp.; Helistat collagen sponge from Integra Lifesciences; Helitene absorbable collagen hemostatic agent in Fibrillar form; and polyethylene glycol (PEG) or collagen/PEG compositions from Cohesion. Such agents also have the useful property of expanding between 3 and 30 times their compressed volume upon release into a cavity and/or upon hydration. The device may also be made to emit therapeutic radiation to preferentially treat any suspect tissue remaining in or around the margin of the biopsy cavity. It is envisioned that the marker would be the best vehicle for dispensing such local radiation treatment or similar therapy. Also, the body itself may be adapted to have radiopaque, echogenic, or other characteristics that allow the body to be located by noninvasive technique without the use of a marker. Such characteristics permit the possibility of locating and substantially identifying the cavity periphery after deployment but prior to absorption of the device. Such an embodiment may allow delivery in liquid or gel form through a much smaller lumen than those marking devices having one of the markers previously described. Furthermore, an echogenic coating may be placed over the radiopaque marker to increase the accuracy of locating the marker during ultrasound imaging.

Figure 1G:
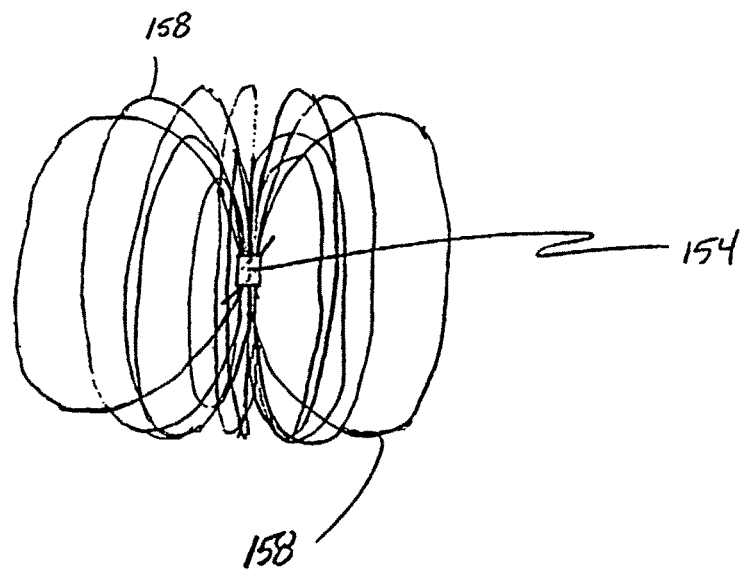
Figure 1H:
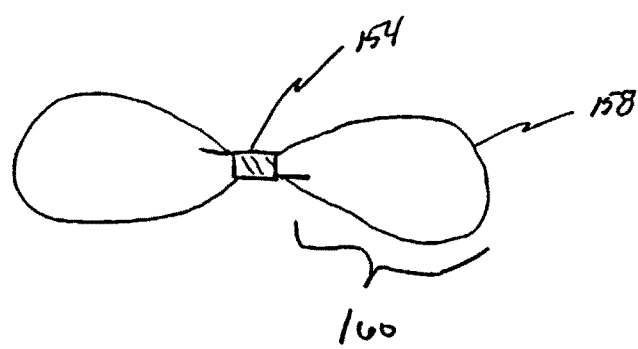
Figure 1I:
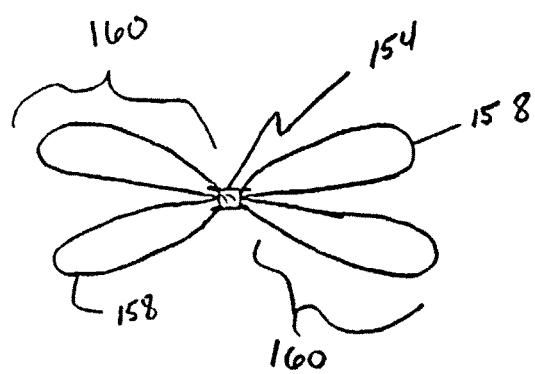
Figure 1J:
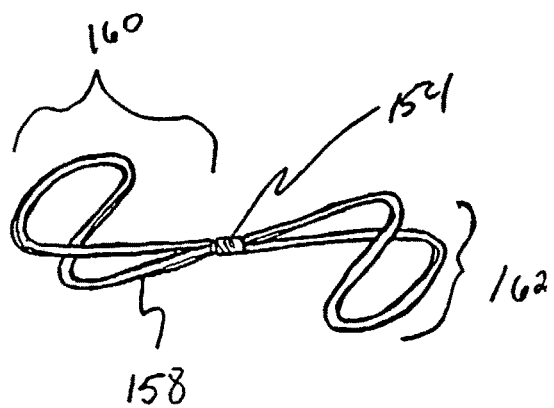
Figure 1K:
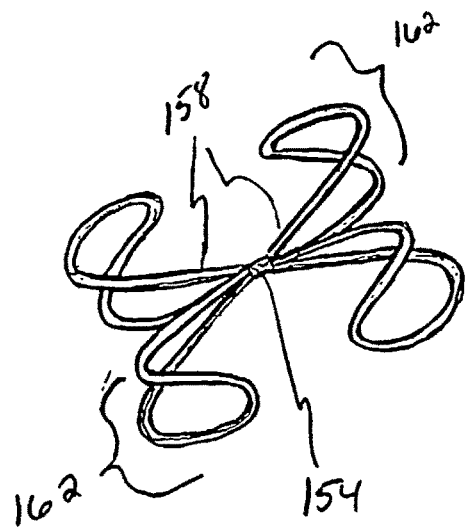

Further, as illustrated in FIGS. 1G-1K, the device can be deployed as a loosely wound ball or looped arrangement of bioabsorbable surgical material with a marker placed at the geometric center of the device. The material may be, for example, resilient suture material, that upon deployment into a tissue cavity provides resistance against the cavity wall and allows the marker to be located at substantially the center of the cavity. In this variation, suture material may be looped through the band/ring 154; in such a configuration, the suture material acts as the body of the inventive device. As described elsewhere, the suture may comprise a bioabsorbable material. The suture material may also have radiopaque, echogenic. or other characteristics described herein that aid in the noninvasive location of the device. Desirably, the suture material 158 is flexible to facilitate the expansion of the filler body to fill the cavity. The device may be in the form of multiple passes of suture material 158 looped through a marker 154 (FIG. 1G). The suture material may also be configured in the form a pair of opposing loops 160 with a marker 154 between the loops 160 (FIG. 1H), or two pairs of opposing loops 160 with the marker 154 in the center of the device (FIG. 1I). The opposing loops 160 may be bent longitudinally to form opposing members 162 (FIGS. 1J, 1K). The longitudinally bent opposing member 162 may be, but is not necessarily, formed by applying heat to the suture to set the "bend". An aspect of this variation is that the opposing members 162 provide resistance against the walls of a delivery device, thereby, minimizing the possibility of the marking device being prematurely released from the delivery device. Upon the desired deployment, the resiliency of the suture will expand the device and provide significant resistance against the walls of the cavity with the opposing members 162 providing additional resistance. It is within the scope of this invention to optionally deliver a biocompatible liquid, gel, powder, or the like before, during, or after deployment of a self-centering suture-containing device such as those illustrated in FIGS. 1G-1K.

Figure 1L:
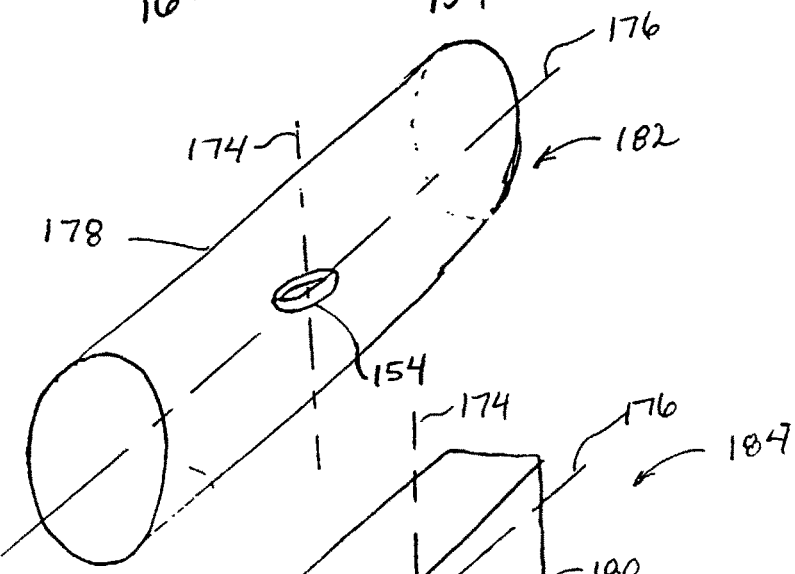
Figure 1M:
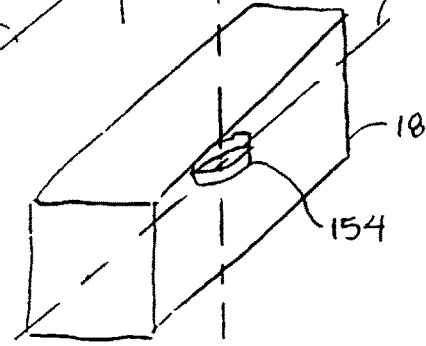

FIGS. 1L and 1M illustrate preferred embodiments of the inventive tissue cavity marking device 182 and 184 each having an elongated body 178 or 180 with a circular or rectangular cross section and a metallic marker band 154. The metallic marker band 154 preferably is oriented with its axis 174 perpendicular to the long axis 176 of the body 178 or 180 to allow maximum compression of the elongated body in the radial direction. The elongated bodies 178 and 180 preferably comprise collagen-containing material with hemostasis-promoting properties.

One method of making the marking device 182 or 184, a marker 154 (or any other marker) may be placed on the edge of a sheet of filler body material such as gelatin or collagen. The sheet may then be rolled or folded to form a device having an elongated body 178 or 180 having a circular or rectangular cross section. Alternatively, a block of collagen or other filler body material may be cut into a rectangular or cylindrical shape. A needle may be used to create a hole through one end lengthwise, preferably only halfway through. A tube containing a marker such as marker 154 may be placed into the hole created by the needle, and a plunger used to push the marker out of the tube and into the filler body, where it may be held in place by friction. Multiple markers may be used to help provide orientation when visualized in the patient on X ray, ultrasound, etc.

One advantage of the collagen material and some of the other materials disclosed herein for the body of the marking device is that it can be easily cut with scissors, a knife, or a scalpel. Therefore, a physician can trim the body of the marking device to fit the cavity during the procedure. This is especially useful when creating the cavity and placing the marking device surgically. Furthermore, if re-excision in the same region is required, the surgeon will have no trouble cutting through the body of the marking device.

Figure 2A:
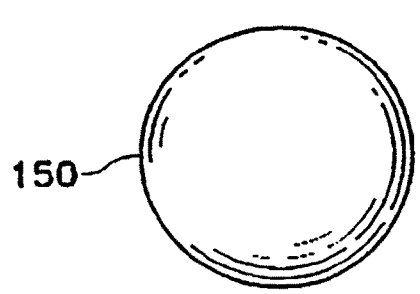
FIGS. 2A-2G illustrate various configurations of the marker.
Figure 2B:
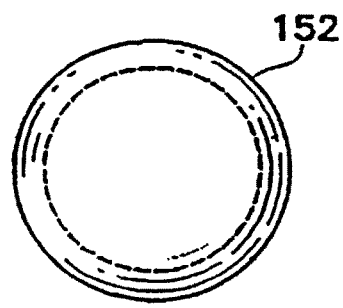
Figure 2C:
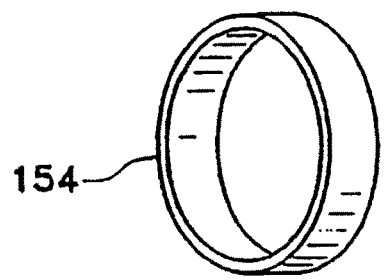
Figure 2D:
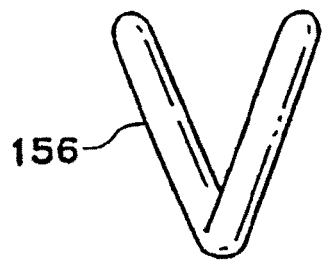
Figure 2E:
Figure 2F:
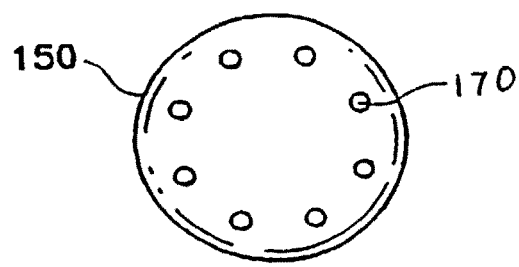
Figure 2G:
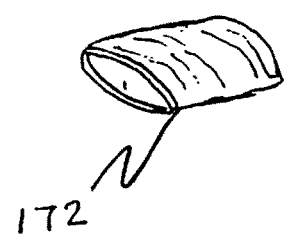

FIGS. 2A-2G illustrate various forms of the marker 110. The marker 110 may be a sphere 150 (FIG. 2A), a hollow sphere 152 (FIG. 2B), a ring or band 154 (FIG. 2C), a barb 156 (FIG. 2D), a flexible suture or flexible wire 158 (FIG. 2E), or a crimped tube or a folded strip of material 172 (FIG. 2G). Also, the marker may have a distinguishing mark 170 (FIG. 2F). As mentioned above, the barb 156 is illustrated in FIG. 2D as having a "V" shape. The barb 156 is intended to distinguish the marker from calcifications when viewed under noninvasive imaging techniques. As such, the barb 156 is not limited to the "V" shape; rather, it has a shape that is easily distinguishable from a spherical or oval calcification.

The marker itself may aid in deploying the body. The marker may be made of a spring material such as superelastic nickel titanium alloy or stainless spring steel for delivery in compression to expand the body to substantially fill the cavity. The barb 156 of FIG. 2D and the flexible wire 158 of FIG. 2E are particularly suited to mechanically aid deployment of the body (not shown).

The hollow sphere 152 of FIG. 2B is more susceptible to detection by ultrasound than the solid sphere 150 of FIG. 2A. For instance, such spherical markers such as markers 150 and 152 can be beads of silicon or silicon-containing compounds, such as silicone or $SiO_2$. In the case of a ring or band marker 154 seen in FIG. 2C, the body of the cavity marking device may be woven or placed through the band or ring 154. The marker may also be a wire or suture 158 as shown in FIG. 2E and as discussed in greater detail below. In such a case, the marker 158 may be affixed to the exterior perimeter of the body by an adhesive or woven through the body. Another improvement may arise from the marker wire or suture 158 being configured in a particular pattern within the body of the device, e.g., wrapping around the body in a helical manner. As described elsewhere, the wire or suture 158 may also be configured to comprise the body of the marking device. In the case of the marker 150 shown in FIG. 2F, distinguishing or identifying mark 170 can be in the form of simple marks as shown, or it may be one or more numbers, letters, symbols, or combinations thereof. These marks 170 are preferably located in more than one location on the marker 150 so that the marker may be readily and simply identified from multiple orientations under a variety of viewing conditions. Such a mark 170 can be used to identify the patient and her condition, provide information about the marker and body of the tissue cavity marking device, provide information about the circumstances and date of the implantation, who performed the procedure, where the procedure was performed, etc. In the case of multiple biopsy sites, this distinguishing mark 170 permits one to differentiate and identify each different site. The mark 170 may be applied via any number of techniques such as physical inscription, physical or plasma deposition, casting, adhesives, etc. The mark 170 may also be an electronic chip providing any necessary information in electronic form that can be remotely detected by appropriate means. The marking device may use the device or technology of a Trovan Transponder (Electronic Identification Systems—Santa Barbara, Calif.). Medical information may itself be directly encoded into the device, or a code on the device may be keyed to a corresponding record in a computerized database containing the medical information. The medical information may include such data as a pathology report of a biopsy sample taken from the site being marked, and this information may be entered into the computer record before or after implantation of the marking device. Furthermore, this information may be updated as needed. Alternatively or additionally, the mark 170 may itself be remotely programmable to add patient or procedure information, pathology information, or the like after implantation in the body, although adding such capability to the marking device may increase its size.

An important aspect of the invention is that the marker may be radiopaque, echogenic, mammographic, etc. so that it can be located by noninvasive techniques. Such a feature can be an inherent property of the material used for the marker. Alternatively, a coating or the like can be added to the marker to render the marker detectable or to enhance its detectability. For radiopacity, the marker may be made of a nonbioabsorbable radiopaque material such as platinum, platinum-iridium, platinum-nickel, platinum-tungsten, gold, silver, rhodium, tungsten, tantalum, titanium, nickel, nickel-titanium, their alloys, and stainless steel or any combination of these metals. By mammographic we mean that the component described is visible under radiography or any other traditional or advanced mammography technique in which breast tissue is imaged.

As previously discussed, the marker can alternatively be made of or coated with a bioabsorbable material. In this case, the marker can, for instance, be made from an additive-loaded polymer. The additive is a radiopaque, echogenic, or other type of substance that allows for the noninvasive detection of the marker. In the case of radiopaque additives, elements such as barium- and bismuth-containing compounds, as well as particulate radiopaque fillers, e.g., powdered tantalum or tungsten, barium carbonate, bismuth oxide, barium sulfate, etc. are preferred. To aid in detection by ultrasound or similar imaging techniques, any component of the device may contain air bubbles or may be combined with an echogenic coating. One such coating is ECHO-COAT from STS Biopolymers. Such coatings contain echogenic features, which provide the coated item with an acoustically reflective interface and a large acoustical impedance differential. As stated above, an echogenic coating may be placed over a radiopaque marker to increase the accuracy of locating the marker during ultrasound imaging.

Note that the radiopacity and echogenicity described herein for the marker and the body are not mutually exclusive. It is within the scope of the present invention for the marker or the body to be radiopaque but not necessarily echogenic, and for the marker or the body to be echogenic but not necessarily radiopaque. It is also within the scope of the invention that the marker and the body are both capable of being simultaneously radiopaque and echogenic. For example, if a platinum ring marker were coated with an echogenic coating, such a marker would be readily visible under x-ray and ultrasonic energy. A similar configuration can be envisioned for the body or for a body coating.

The marker is preferably large enough to be readily visible to the physician under x-ray or ultrasonic viewing, for example, yet be small enough to be able to be percutaneously deployed into the biopsy cavity and to not cause any difficulties with the patient. More specifically, the marker will not be large enough to be palpable or felt by the patient.

Figure 3A:
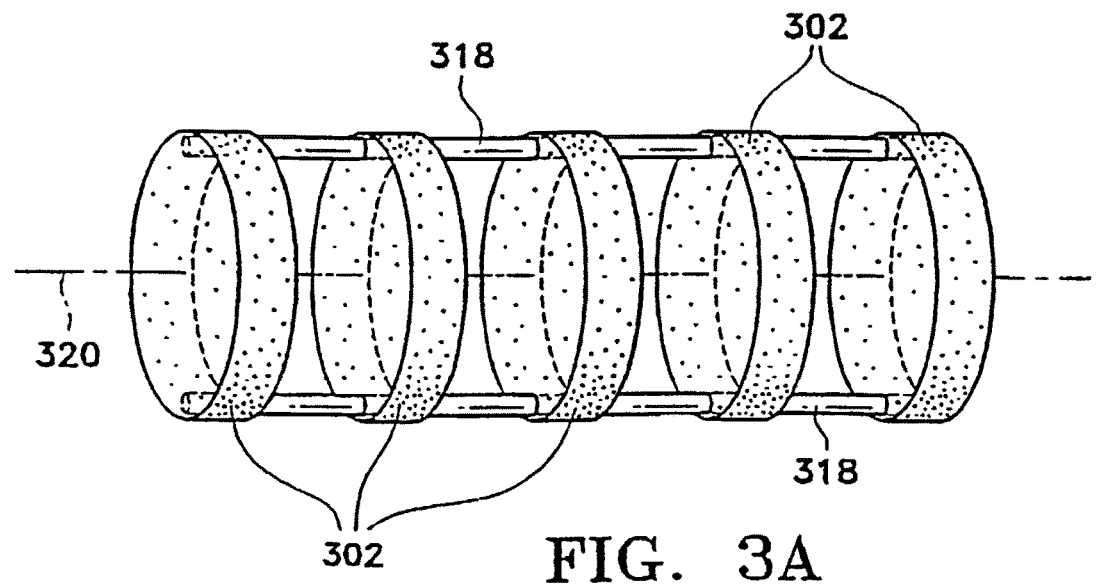
FIG. 3A illustrates a cavity marking device having multiple body components traversed by a single wire or suture marker, or multiple wires or suture markers.

Another useful version of the invention is shown in FIG. 3A. In this device, there are several cylindrical body members 302; however, there is no limit to the number of body members that can make up the device. The body members 302 can individually or together take on a variety of sizes and shapes as discussed above depending on the characteristics of the biopsy cavity to be filled. The body members 302 may uniformly or in combination be made of one or more materials suitable for use in a biopsy cavity as previously described.

Here one or more markers may traverse two or more body member segments through the interior of the body members 302 as shown in FIG. 3A. Here, markers 318 are located substantially parallel to the longitudinal axis 320 of each right cylindrical body member 302 in their interior, connecting each body member 302 while marking their geometric center as between the markers. Such a marker 318 may be used in conjunction with the other markers as described above and may also be accompanied by one or more additional markers arranged randomly or in a predetermined pattern to variously mark particular sections of the device. Alternately, such a marker may, singly or in combination with other markers, be affixed on or near the surface of the sponge so as to mark the perimeter of the body member 302.

Of course, when used in conjunction with other connecting markers, marker 318 need not necessarily connect each body member; it may be used solely to indicate the orientation or location of each individual sponge or the entire device, depending on the material, geometry, size, orientation, etc. of marker 318. When not used in this connecting function, therefore, marker 318 need not traverse two body members 302 as shown in FIG. 3A.

Figure 3B:
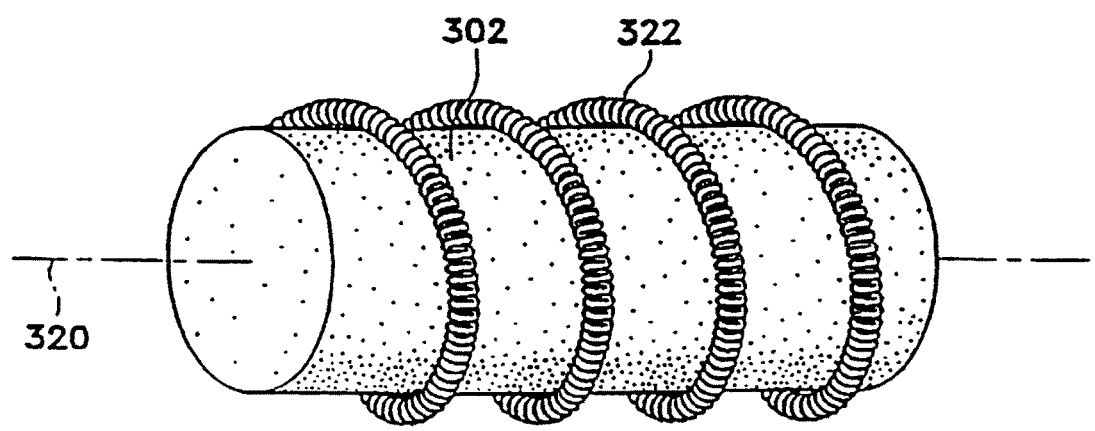
FIG. 3B illustrates a cavity marking device having a helically wound wire or suture marker.
Figure 3C:
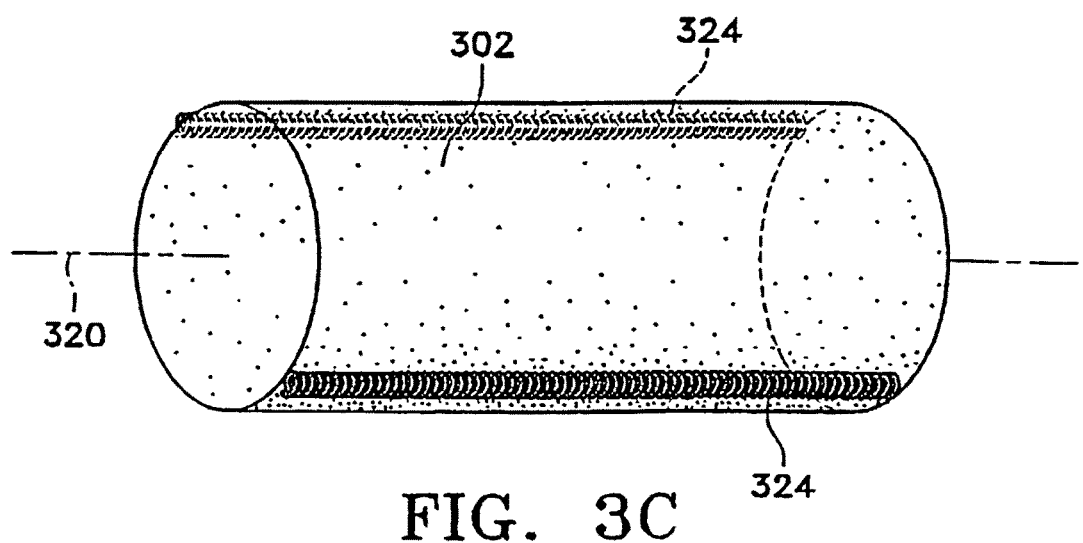
FIG. 3C illustrates a cavity marking device having wire or suture markers on the perimeter of the body.
Figure 3D:
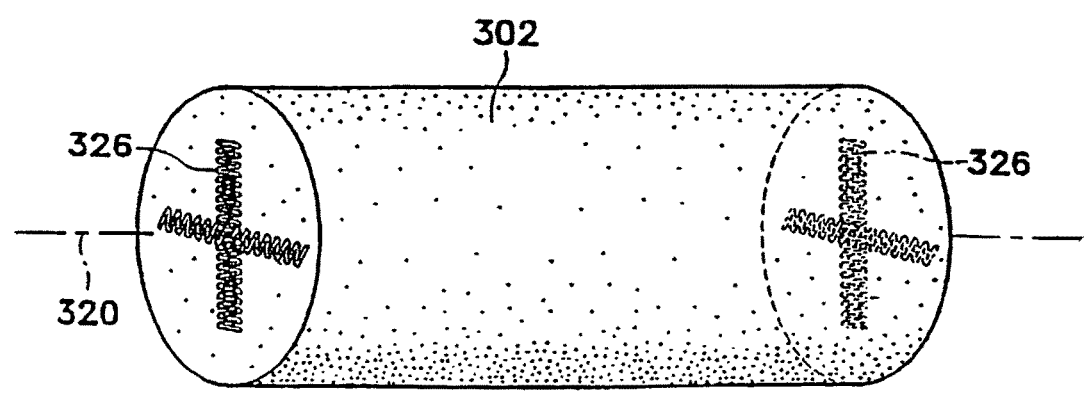
FIG. 3D illustrates a cavity marking device having wire or markers on the ends of the body.

A variety of patterns can be envisioned in which all or part of the perimeter of the sponge body is marked. For example, a marker 322 can wrap around the body 302 in a helical pattern (FIG. 3B), or it can be used in conjunction with other markers 324 in a pattern parallel to the longitudinal axis 320 of the body 302 (FIG. 3C). Another useful perimeter marking pattern is shown in FIG. 3D, where marker segments 326 are affixed at or near the surface of the circular bases of the cylindrical body 302 in a cross pattern, indicating the ends of the sponge and their center. As seen from the figures, the marker(s) may, but do not necessarily, have some texture. Any marker pattern, internal or external to the body, is within the scope of the present invention. For the applications depicted in FIGS. 3A-3D, it is preferred that the marker be a radiopaque or echogenic wire or suture.

Another possible configuration is obtained by combining the suture or wire markers 158 in a body with any other type marker 150, 152, 154, or 156 or vice versa. For example, in FIG. 3B, a spherical marker 150 may be placed in the center of the cylindrical body 302. Therefore, the cylindrical body 302 would contain the suture or wire marker 322 wrapped helically adjacent to the outer perimeter, and a marker 150 would be placed in the center of the cylindrical body 302. Such a combination may be obtained with any of the body and marker configurations as defined above.

Also, turning back to the marking device 100 in FIG. 1A or the marking device 100 of FIG. 1B, the markers 150 or 154 may be substituted with one or more suture or wire markers 158, preferably extending through the center and pointing radially away from the center. This configuration allows marking of the cavity perimeter and establishing of the directionality of the cavity itself.

Any of the previously-described additional features of the inventive device, such as presence of pain-killing or hemostatic drugs, the capacity for the marker to emit therapeutic radiation for the treatment of various cancers, the various materials that may make up the marker and body, and their size, shape, orientation, and geometry, may be incorporated into the device described above in conjunction with FIGS. 3A-3D.

Figure 4A:
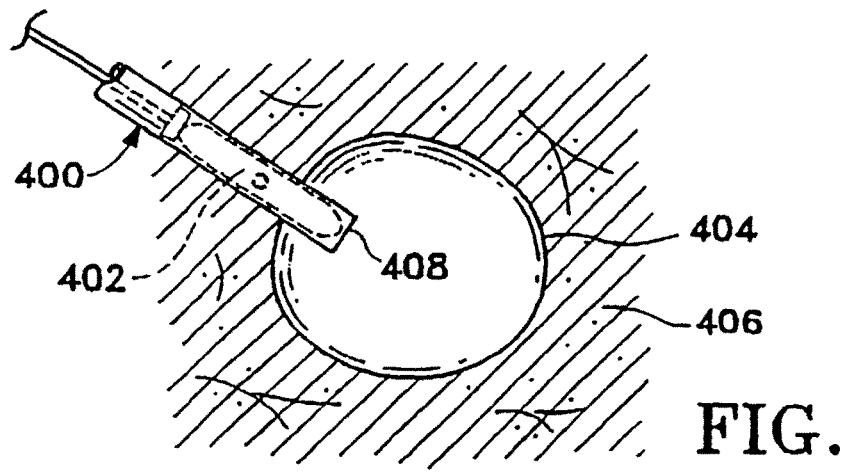
FIGS. 4A-4C illustrate a method of marking a biopsy tissue cavity with the device of the present invention.
Figure 4B:
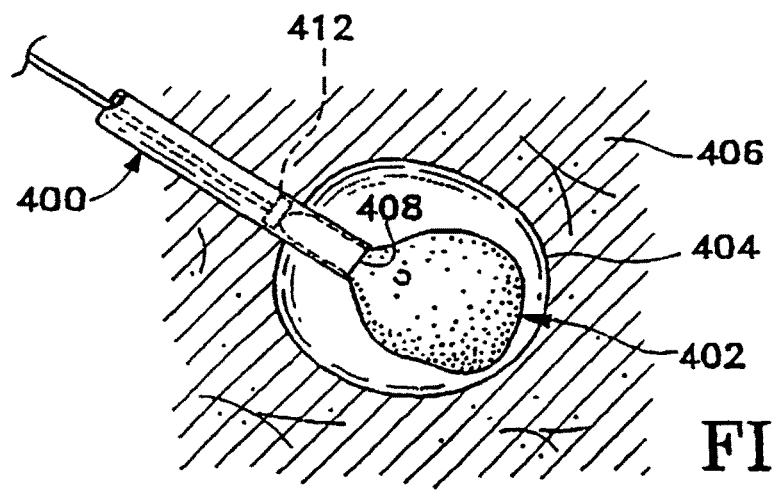
Figure 4C:
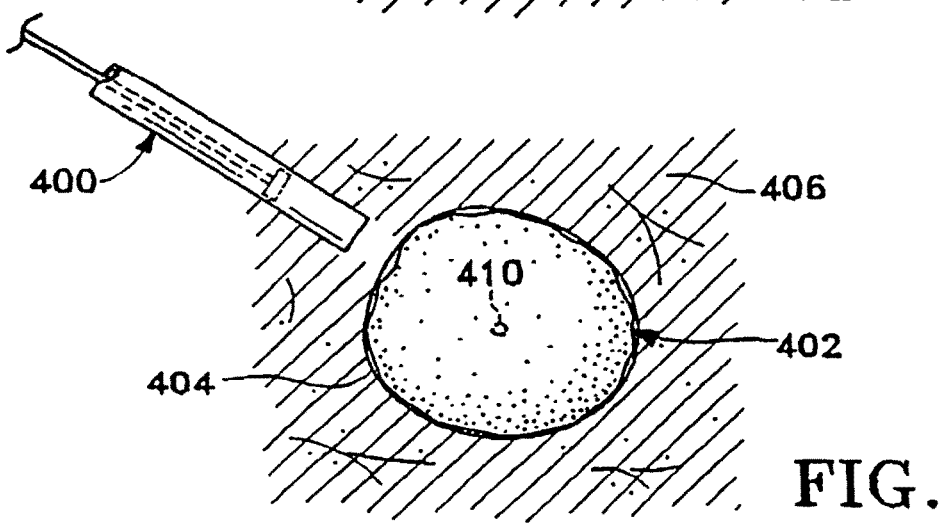

Turning now to FIGS. 4A-4C, a method of delivering the inventive device of FIG. 1A is shown. FIG. 4A details the marking device 402 just prior to delivery into a tissue cavity 404 of human or other mammalian tissue, preferably breast tissue 406. As can be seen, the step illustrated in FIG. 4A shows a suitable tubular percutaneous access device 400, such as a catheter or delivery tube, with a distal end 408 disposed in the interior of cavity 404. As previously described, the marking device 402 may be delivered percutaneously through the same access device 400 used to perform the biopsy in which tissue was removed from cavity 404. Although this is not necessary, it is less traumatic to the patient and allows more precise placement of the marking device 402 before fluid begins to fill the cavity 400.

FIG. 4B shows marking device 402 being pushed out of the distal end 408 of access device 400 by a pusher 412 and resiliently expanding to substantially fill the tissue cavity 404.

Finally, in FIG. 4C, access device 400 is withdrawn from the breast tissue, leaving marking device 402 deployed to substantially fill the entire cavity 404 with radiopaque or echogenic marker 410 suspended in the geometric center of the marking device 402 and the cavity 404. As mentioned above, the marking device 402 may be sized to be larger than the cavity 404 thus providing a significant resistance against the walls of the cavity 404.

FIGS. 4D-4F show a method of delivering the marking device 402 into a tissue cavity 404 by a plunger 414 that is capable of both advancing the marking device 402 and delivering a biocompatible fluid 416. The "biocompatible fluid" is a liquid, solution, or suspension that may contain inorganic or organic material. The fluid 416 is preferably a saline solution, but may be water or contain adjuvants such as medications to prevent infection, reduce pain, or the like. Alternatively or additionally, the fluid may be used to mark the sentinel lymph node. Obviously, the fluid 416 is intended to be a type that does no harm to the body.

FIG. 4D details the marking device 402 prior to delivery into the tissue cavity 404. In FIG. 4E, a plunger 414 pushes the marking device 402 out of the access device 400. Upon exiting the access device 400 the marking device 402 begins resiliently expanding to substantially fill the cavity 404.

FIG. 4F shows the plunger 414 delivering the biocompatible fluid 416 into the cavity 404. The plunger 414 may be equipped with a Luer or other type fitting to attach a fluid reservoir or syringe (not shown). The fluid 416 aids the marking device 402 in expanding to substantially fill the cavity 404. In this example, the biocompatible fluid 416 is delivered subsequent to the placement of the marking device 402 in the cavity 404. The marking device 402 may also be soaked with fluid 416 prior to placement in the cavity 404. Furthermore, the fluid 416 may be delivered prior to delivery of the marking device 402.

Figure 4G:
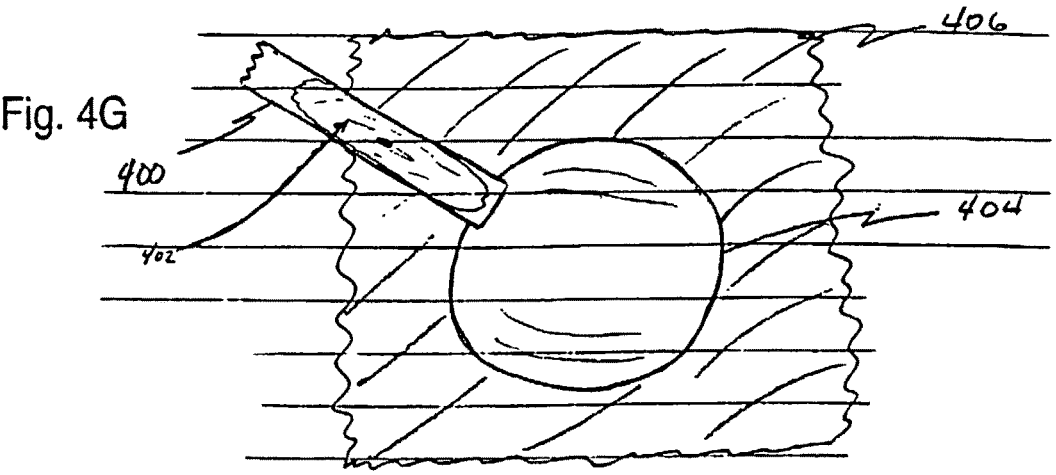
FIGS. 4G-4I illustrate a method of marking a biopsy tissue cavity with the device of the present invention wherein a biocompatible fluid is used to push the cavity marking device out of the access device and into the biopsy tissue cavity.
Figure 4H:
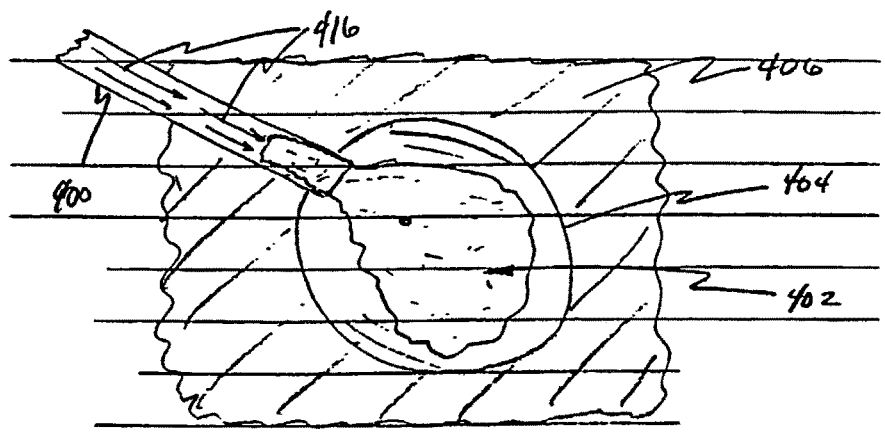
Figure 4I:
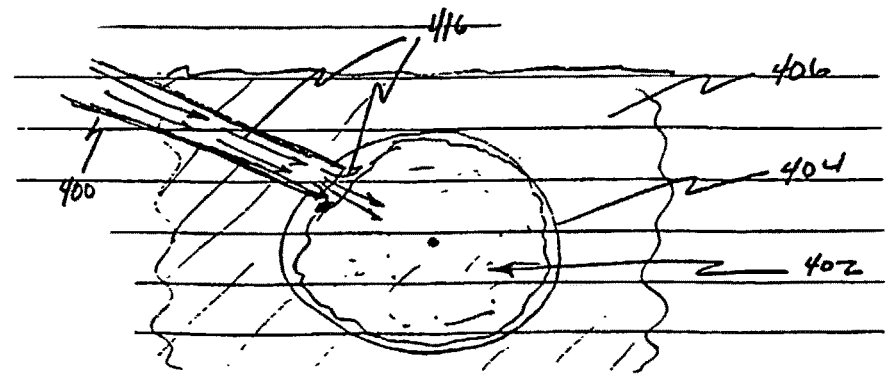

FIGS. 4G-4I show another method of delivering the marking device 402 into the tissue cavity 404 by using the biocompatible fluid 416 as the force to deliver the marking device 402 into the tissue cavity 404.

FIG. 4G details the marking device 402 prior to delivery into the tissue cavity 404. FIG. 4H illustrates flow of the biocompatible fluid 416 in the access device 400, the fluid 416 flow then pushes the marking device 402 out of the access device 400.

FIG. 4I shows the delivery device 400 continuing to deliver the biocompatible fluid 416 into the cavity 404. The fluid 416 aids the marking device 402 in expanding to substantially fill the cavity 404. In this example, the biocompatible fluid 416 is delivered after the placement of the marking device 402 in the cavity 404 although the invention is not limited to the continued delivery of the fluid 416.

FIGS. 4J-4L show the method of delivering the body 418 of the cavity marking device directly into the cavity 404 prior to the placement of the marker 410 in the device 402.

FIG. 4J shows the deposit of the body material 418 into the cavity 404. In this case the body material 418 may be a gel type material as described above. FIG. 4K details the filling of the cavity 404 with the body material 418. At this point, the delivery device (not shown in FIG. 4K) may be withdrawn. FIG. 4L details the placement of the marker 410 into the body material 418.

FIGS. 5A-5E show yet another version of the invention in which a marker, preferably consisting of a radiopaque or echogenic wire, is deployed alone into a tissue cavity without the use of any body. In this device, the marker can be made of a shape memory material, such as a nickel-titanium alloy, which, when deployed into the biopsy cavity, assumes a predetermined configuration to substantially fill the cavity, mark the cavity location and margin, and indicate the orientation of the marker inside the cavity. The open design of these deployable markers allows tissue in-growth, that further stabilizes the markers. Furthermore, the periphery of the cavity is marked with a relatively small amount of implanted material.

Figure 5A:
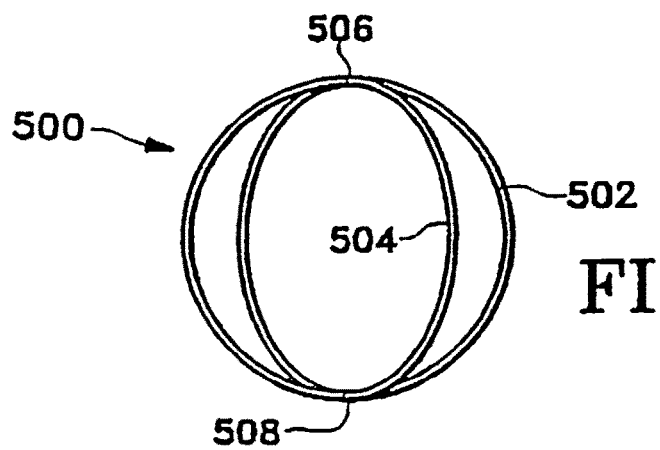
FIGS. 5A-5B illustrate a spherical wire marking device for deployment without a filler body into a tissue cavity.
Figure 5B:
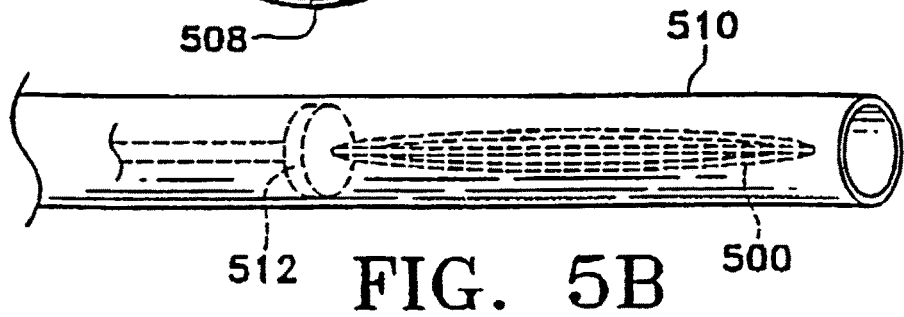

In FIG. 5A, marker 500 is a three-dimensional sphere consisting of two rings 502 and 504 pivotally connected at ends 506 and 508 so to assume a spherical shape. Such a marker can be made of a shape memory metal so that when it is placed in a deployment tube 510 shown in FIG. 5B, marker 500 assumes a collapsed profile suitable for deployment through tube 510 by pusher 512. Upon exiting into the tissue cavity (not shown), marker 500 assumes the spherical shape of FIG. 5A to fill the cavity. The marker 500 may also be shaped into any similar shape such as an ellipsoidal shape.

Figure 5C:
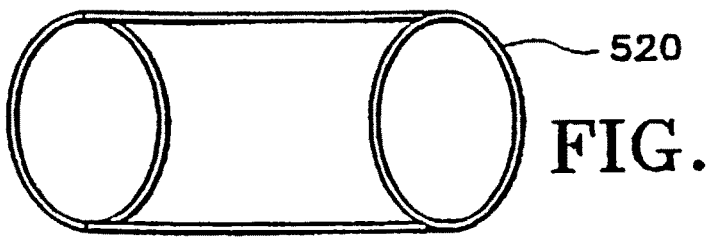
FIG. 5C illustrates a cylindrical wire marking device for deployment without a filler body into a tissue cavity.

Turning now to FIG. 5C, a marker 520 in the form of a wire cylinder is shown. Again, this device is structurally configured to assume the depicted cylindrical configuration when deployed in the tissue cavity, but may be (as described above) "collapsed" into a deployment tube for percutaneous delivery. This device is especially suitable for marking the distal and proximal ends of the tissue cavity due to its asymmetrical shape.

Figure 5D:
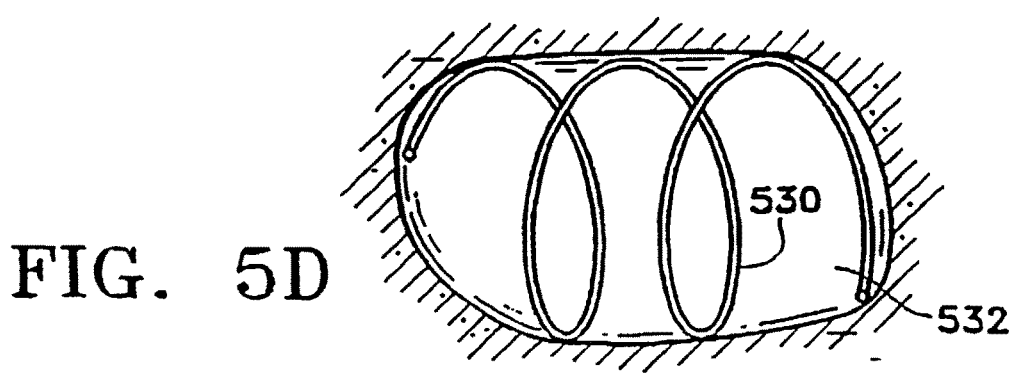
FIGS. 5D-5E illustrate a helical coil wire marking device for deployment without a filler body into a tissue cavity.
Figure 5E:
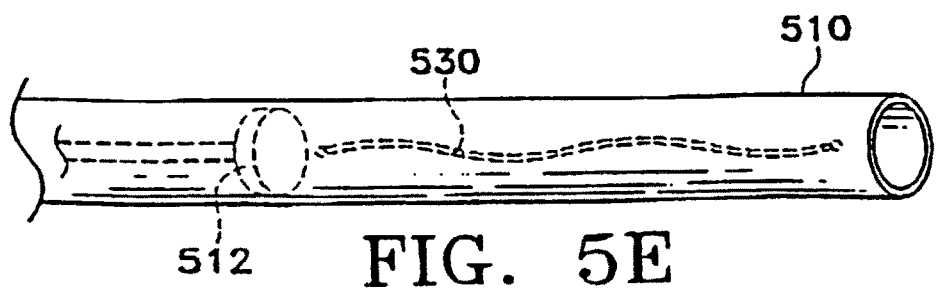

FIG. 5D shows a shape memory marker 530 in the form of a helical coil deployed into tissue cavity 532. Again, as seen in FIG. 5E, such a marker 530 may be deployed through delivery tube 510 by pusher 512 in a substantially elongated, straightened form, only to substantially assume the shape of the cavity 532 as shown in FIG. 5D. Any suitable delivery device or pusher 512 capable of deploying marker 530 into cavity 532 is within the scope of this invention.

Each of the markers shown in FIGS. 5A-5E is preferably a shape memory material coated or supplemented with a radiopacity-enhancing material, such as gold, platinum, or any other radiopaque material herein discussed. The markers may singly, or in combination with being radiopaque, be echogenic or be made echogenic by any of the materials or methods herein described.

Each of the markers shown in FIGS. 5A-5E is preferably self-centering. It is within the scope of the invention to add one or more materials such as a biocompatible liquid, gel, powder, or the like into the cavity before, during, or after delivery of those markers; the material may provide treatments such as hemostasis, antibiotic properties, or pain relief. In addition, a marker of any of the type shown in FIGS. 2A-2G may be inserted into the optional material to mark the center or provide patient information as described with respect to FIG. 2F.

FIGS. 6A-6D show a method of delivering the marking device 602 into a tissue cavity 604 that allows the marking device 602 to radially expand to substantially fill the cavity 604 without the need for simultaneous pushing of the marking device 602 into the cavity 604. While the marking device 602 depicted in FIGS. 6A-6D is depicted as a bioabsorbable surgical material with a marker placed at the geometric center of the device, the method is not limited to such devices. Any of the marker devices described herein may be used with this method.

Figure 6A:
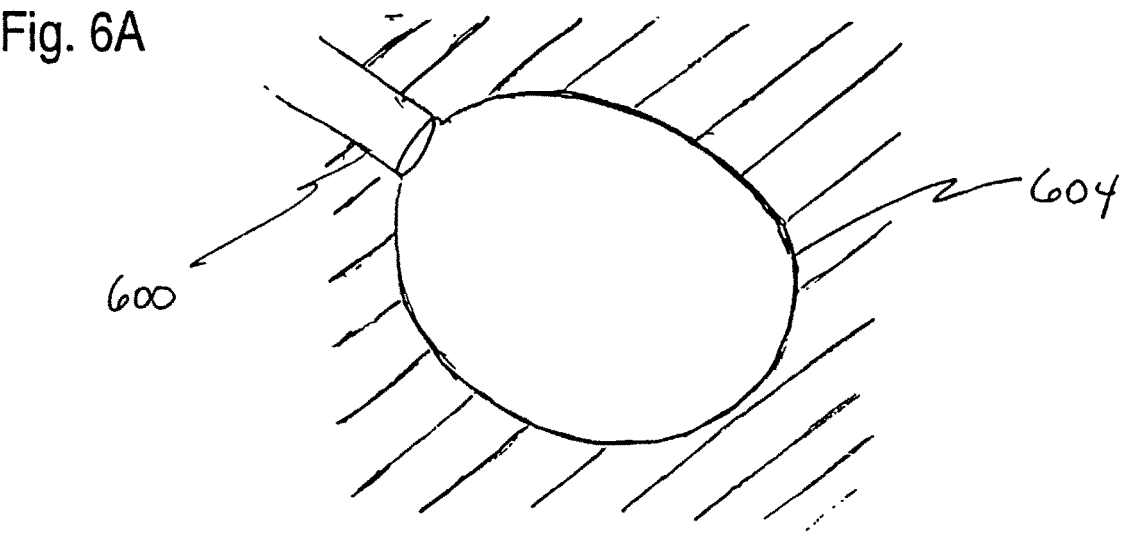
FIGS. 6A-6D illustrate a method for marking a biopsy tissue cavity with the marking device of the present invention wherein the marking device expands into the cavity without the need for simultaneous pushing of the marking device into the cavity.

FIG. 6A details insertion of a sheath 600 into communication with tissue cavity 604. Preferably, the sheath 600 is placed through the same access pathway (not shown) used by the biopsy device (not shown). The sheath 600 is placed soon after the cavity 604 is formed.

Figure 6B:
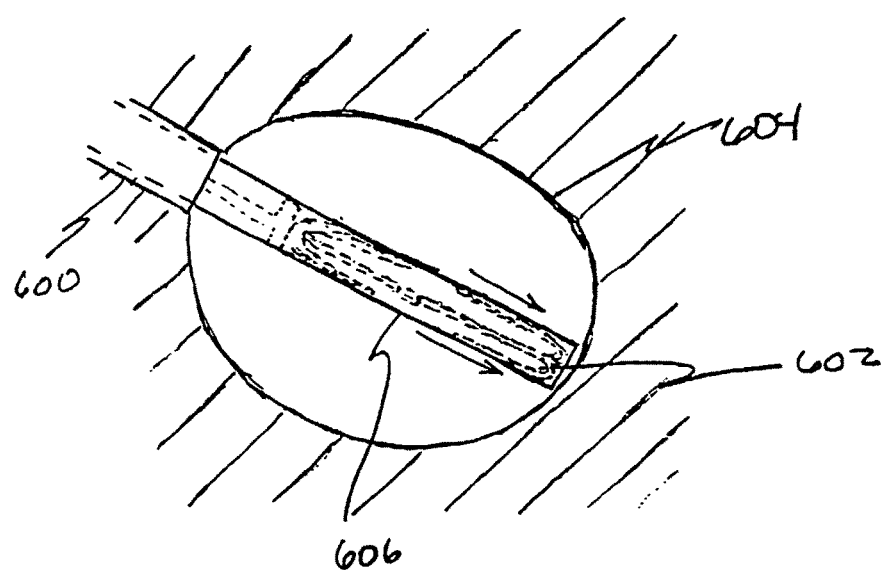

FIG. 6B illustrates insertion of a cartridge or applicator 606 through the sheath 600 and into the cavity 604. The cartridge 606 may contain a marking device 602 and a disengaging arm (not shown.) Preferably, the cartridge 606 is advanced into the cavity 604 until the marking device 602 is located within the cavity 604.

Figure 6C:
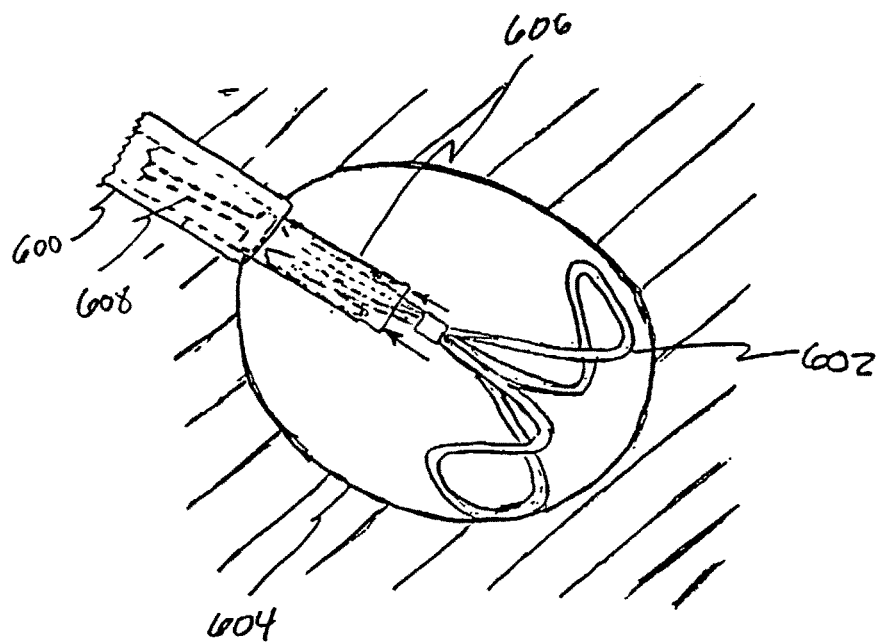

FIG. 6C illustrates the withdrawal of the cartridge 606 from the cavity 604 and the partial expansion of the cavity marking device 602. As shown in the figure, the disengaging arm 608 within the cartridge 606 permits withdrawal of the cartridge 606 independently of the marking device 602. Thus, the marking device 602 remains within the cavity 604. The use of the disengaging arm 608 permits the placement of the marking device 602 while allowing for a significant frictional fit between the marking device 602 and the cartridge 606. This frictional fit minimizes the possibility of accidental deployment of the marking device 602.

Figure 6D:
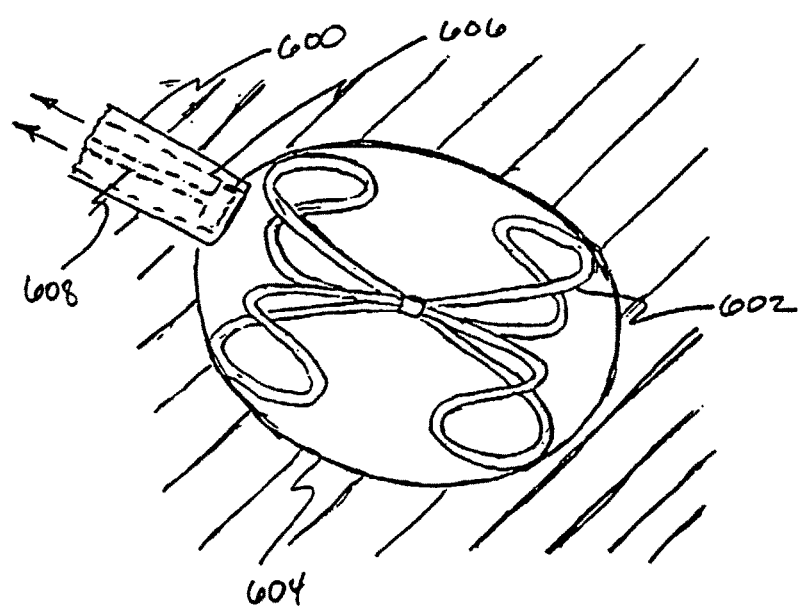

FIG. 6D illustrates the withdrawal of the cartridge 606 and the disengaging arm 608 from the cavity 604 leaving the marking device 602 to radially expand into the cavity 604. Although it is not shown, after the marking device 602 is placed within the cavity 604, fluid (not shown) may be delivered to the cavity 604 to assist the expansion of the marking device 602. Ultimately, the sheath 600 and cartridge 606 are withdrawn from the cavity 604 and further withdrawn from the body.

FIGS. 7A-7K show devices for delivering a marking device into a tissue cavity which allow the marking device to radially expand to substantially fill the cavity without the need for simultaneous pushing of the marking device into the cavity.

Figure 7A:
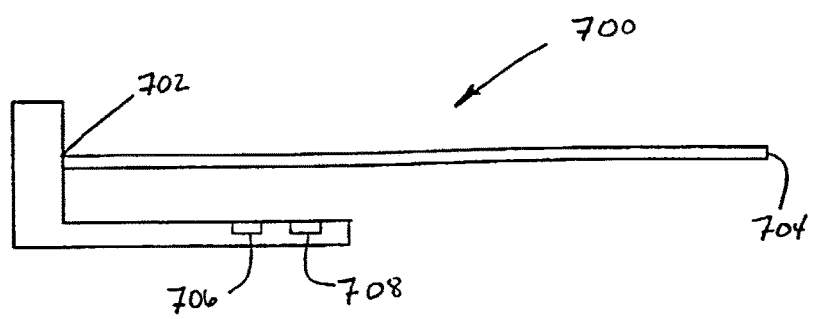
FIGS. 7A-7K illustrate devices for marking a biopsy tissue cavity with the marking device of the present invention.
Figure 7C:

FIG. 7A illustrates a variation of a disengagement arm 700 having distal 704 and proximal 702 ends. The disengagement arm 700 of this figure has first and second slots 706 and 708 that allow for a cartridge 710 and sheath 716 to have fixable positions along the disengagement arm 700. Although it is not shown, the disengagement arm 700 may be configured to have a lumen (not shown) to provide delivery of fluid to the cavity to assist with the expansion of the marking device (not shown).

Figure 7B:
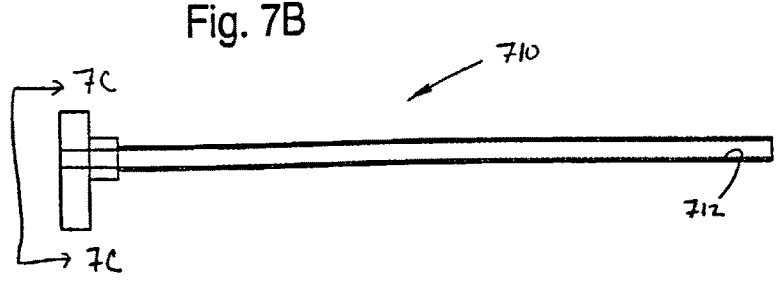
Figure 7E:
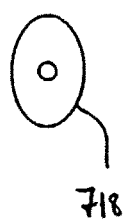
Figure 7D:
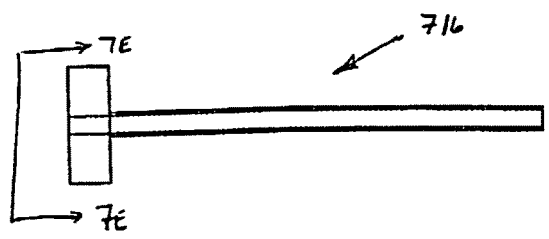

FIG. 7B illustrates a variation of a cartridge 710 having a lumen 712 for placement of a marking device (not shown). The cartridge 710 has an offset member 714 visible in FIG. 7C. In this embodiment, the offset member 714 engages with the first slot 706 of the disengagement arm 700 to define a fixable position of the cartridge 710 along the disengagement arm 700. FIG. 7D illustrates a sheath 716 having an offset member 718, as shown in FIG. 7E, which engages with the second slot 708 of the disengagement arm 700 to define a fixable position of the sheath 716 along the disengagement arm 700. The cartridge 710 may be rotated about the disengagement arm 700 so that the offset member 714 is removed from the slot 706 allowing the cartridge 710 to be moved to the proximal end of the disengagement arm 700.

Figure 7F:
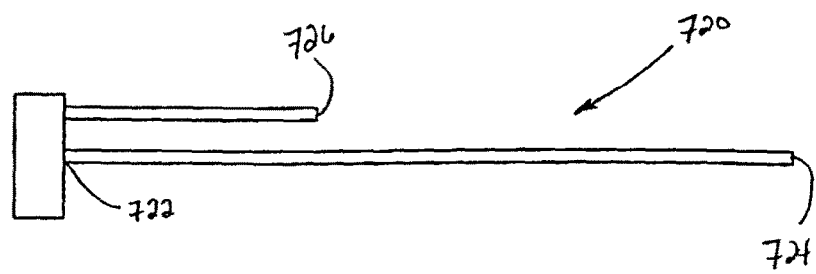
Figure 7H:
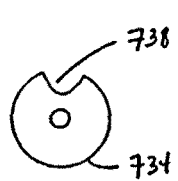
Figure 7G:
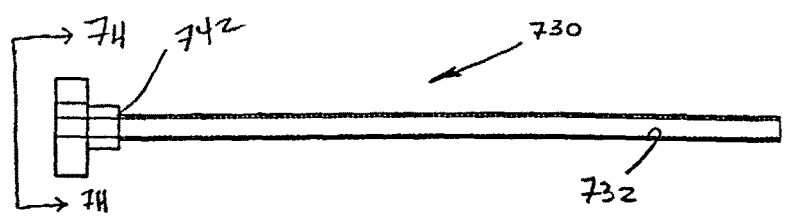
Figure 7I:
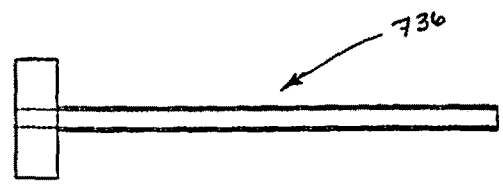

FIG. 7F shows another variation of a disengagement arm 720 having distal 724 and proximal 722 ends. The disengagement arm 720 of this variation has a stop 726 that allow for a cartridge 730 and sheath 736 to have fixable positions along the disengagement arm 720. FIG. 7G shows a variation of a cartridge 730 having a lumen 732 for placement of a marking device (not shown). The cartridge 730 has a flange 734, as shown in FIG. 7H, which rests against the stop 726 of the disengagement arm 720 to provide the cartridge 730 with a fixable position along the disengagement arm 720. The cartridge 730 may be rotated about the disengagement arm 720 so that an opening 738 in the flange 734 allows the cartridge 730 to be moved to the proximal end of the disengagement arm 722. On the cartridge 730 of FIG. 7G, a sheath may have a fixable position along the cartridge 730 as the sheath is placed against a proximal end 742 of the cartridge 730. FIG. 7I shows a variation of the sheath 736 for use with the disengagement arm 720 and cartridge 730 of FIGS. 7F and 7G. Although it is not shown, the disengagement arm 720 may be configured to have a lumen (not shown) to provide delivery of fluid to the cavity to assist with the expansion of the marking device (not shown).

Figure 7J:
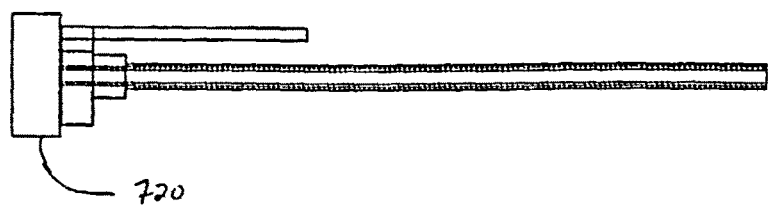
Figure 7J:
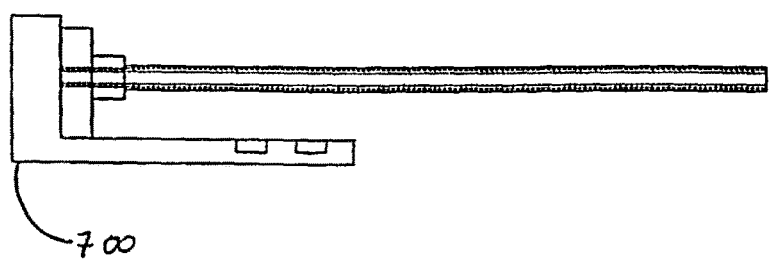
Figure 7K:
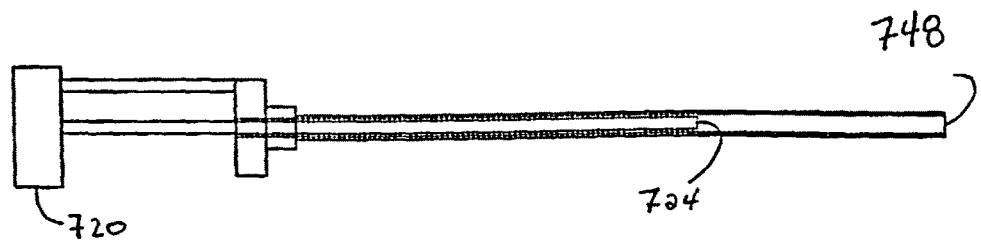
Figure 7K:
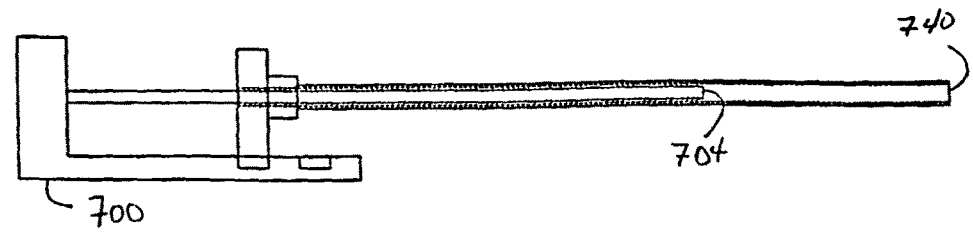

FIG. 7J illustrates the variations of the cartridge devices against a proximal end of the disengagement arms 720 and 700. FIG. 7K illustrates the variations of the cartridge devices in a fixable position along the disengagement arms 720 and 700. In these positions, the end portions 748 and 740 of the cartridges 720 and 700 extend beyond the distal ends 724 and 704 of the disengagement arms.

FIGS. 8A-8I illustrate a delivery device 800 and a method for using it to deliver a marking device 860 to a tissue cavity 874 accessed and/or made by the probe 882 of a medical instrument 880. The probe 882 is preferably between 1 and 25 mm in its largest cross sectional dimension (diameter, if circular), and most preferably between 2 and 5 mm. Although the marking device 860 is shown as the type shown in FIG. 1K, it is not limited to such, and may be of any type disclosed in this application or any other type.

Figure 8A:
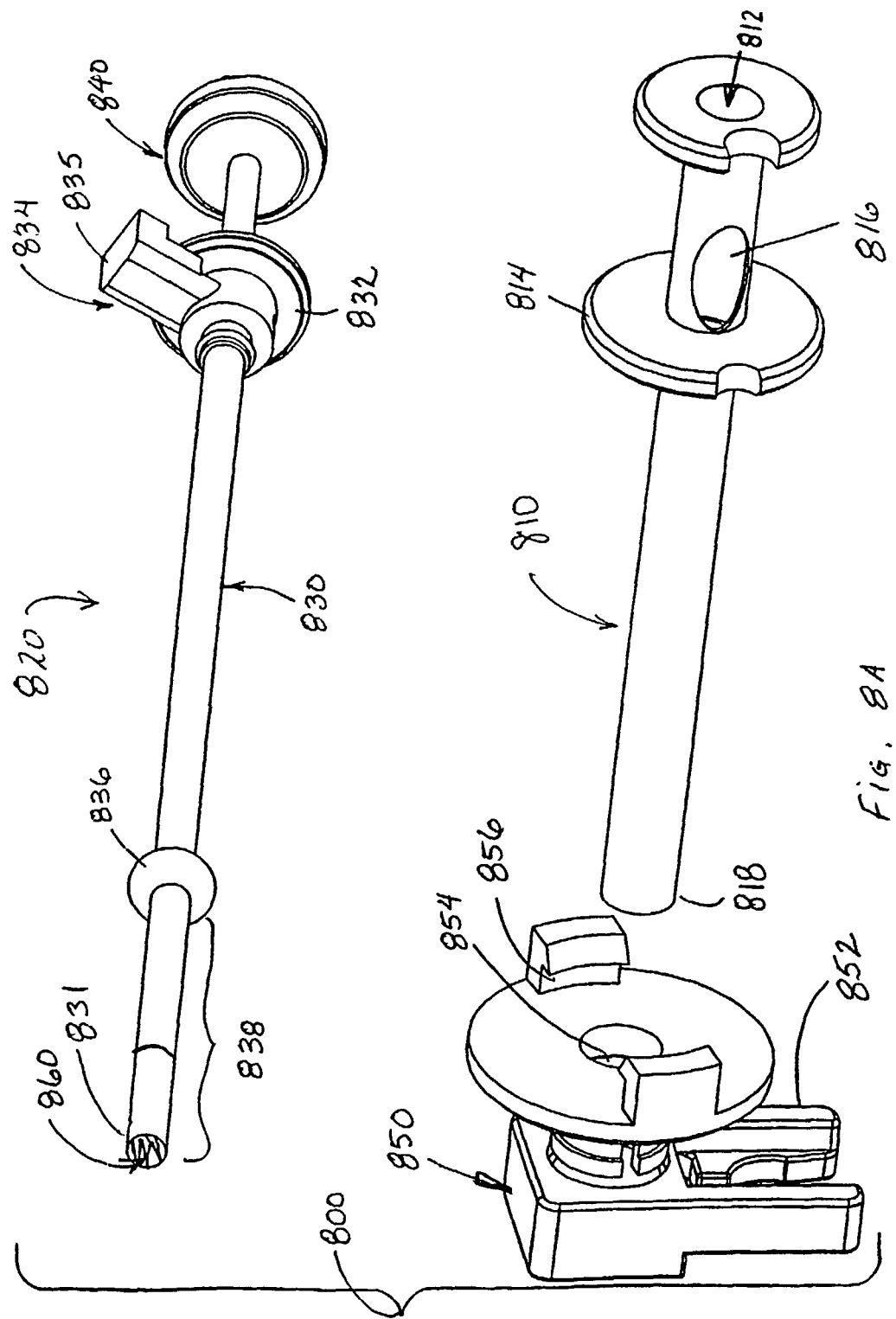
Figure 8B:
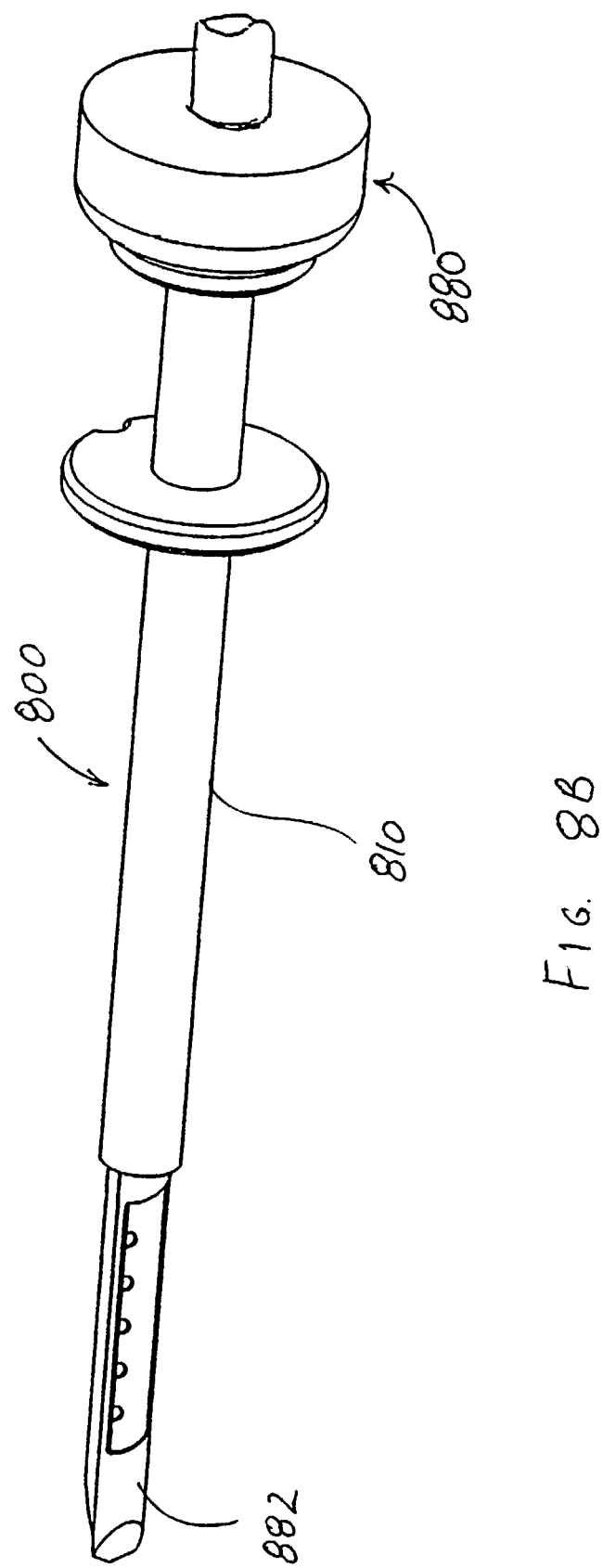

As seen in FIG. 8A, the delivery device 800 includes an outer sheath 810 having a proximal entryway 812 for the probe 882 (shown in FIG. 8B). The outer sheath 810 further includes an outer sheath hub 814 and an optional side port 816. The outer sheath 810 may be circular or noncircular in cross section regardless of whether the probe 882 has a circular or noncircular cross section. For example, if the outer sheath 810 is flexible and circular in cross section, but the probe 882 is shaped like a "FIG. 8", the outer sheath 810 may conform to follow the contours of the probe when the outer sheath is placed over the probe. For example, for a probe having such a FIG. 8 configuration with its largest cross sectional dimension about 4.6 mm and its smallest about 3 mm; the outer sheath may have a circular cross section with an inner diameter of about 4 mm. The delivery device 800 further includes an applicator 820, which is made up of an inner sheath 830 and a plunger 840. The inner sheath 830 may further comprise an inner sheath hub 832, a safety lock 834 with a safety tab 835, a stop 836, and a distal portion 838 that is distal of the stop 836. A marking device 860 may be preloaded within the distal portion 838 of the inner sheath 830. For the example above of a 4-mm inner diameter outer sheath, the inner sheath will easily accommodate a marking device having a compressed diameter up to about 3.3 mm. The inner sheath hub 832 is preferably immovable on the inner sheath 830, providing both a grip for pushing the plunger 840 and a support for the safety lock 834. Furthermore, the inner sheath hub 832 may also function as a stop, thereby eliminating the need for separate stop 836. The distal portion 838 of the inner sheath 830 is sized to fit through either the entryway 812 or the side port 816 of the outer sheath 810 up to the inner sheath stop 836. The delivery device 800 preferably includes a guide 850 having a clamp 852 for attachment to a first point that is fixed with respect to a desired marking site within the patient. This first fixed point could be, for example, on the patient herself, on a stereotactic table, or on an attachment on a stereotactic table, such as a rail, a fixed portion of a driver attached to the stereotactic table, or the like. The guide 850 has a channel 854 through which the outer sheath 810 may slide. The guide 850 also has a locking mechanism 856 that can engage the outer sheath hub 814. The inner and outer sheaths are preferably made of Pebax, a fluoropolymer such as Teflon®, or polyethylene, and may be radiopaque or echogenic. The hubs 814 and 832 and guide 850 are preferably made of polycarbonate or polypropylene.

As shown in FIG. 8B, to use the delivery device 800, the outer sheath 810 is placed over a probe 882 of a medical instrument 880, such as a biopsy probe.

Figure 8C:
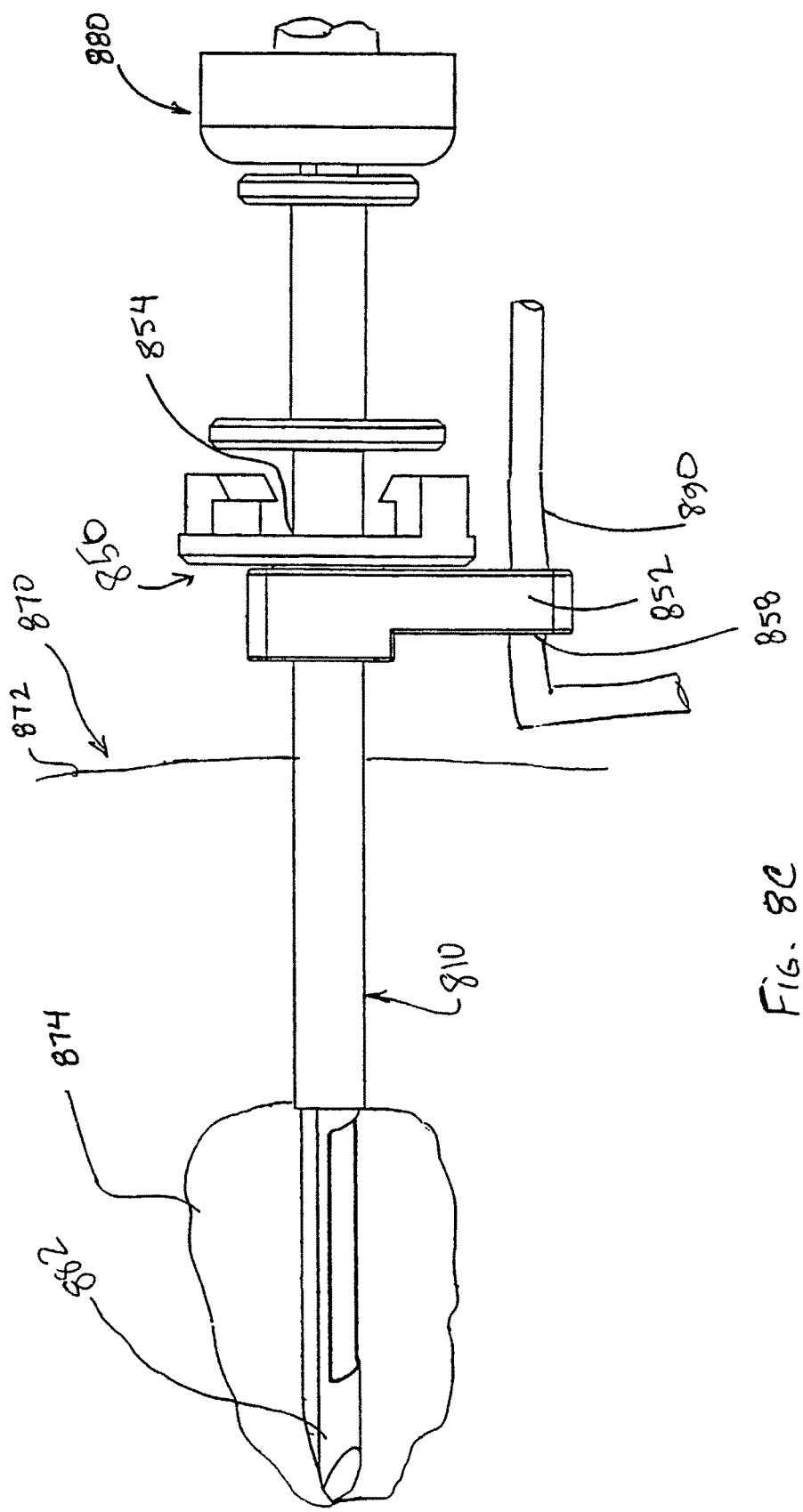

As shown in FIG. 8C, a guide 850 preferably is attached, using a clamp 852, to a first point 858 that is fixed with respect to the patient 870, such as a fixed point on the medical instrument 880, a rail of a stereotactic table 890 (as shown), or the patient herself. The probe 882 with the outer sheath 810 is introduced through the channel 854 of the guide 850, through the skin 872 of the patient 870, and into the site where the marker is to be deployed; this step may comprise taking a tissue sample, thus creating a cavity 874 in the tissue.

Figure 8D:
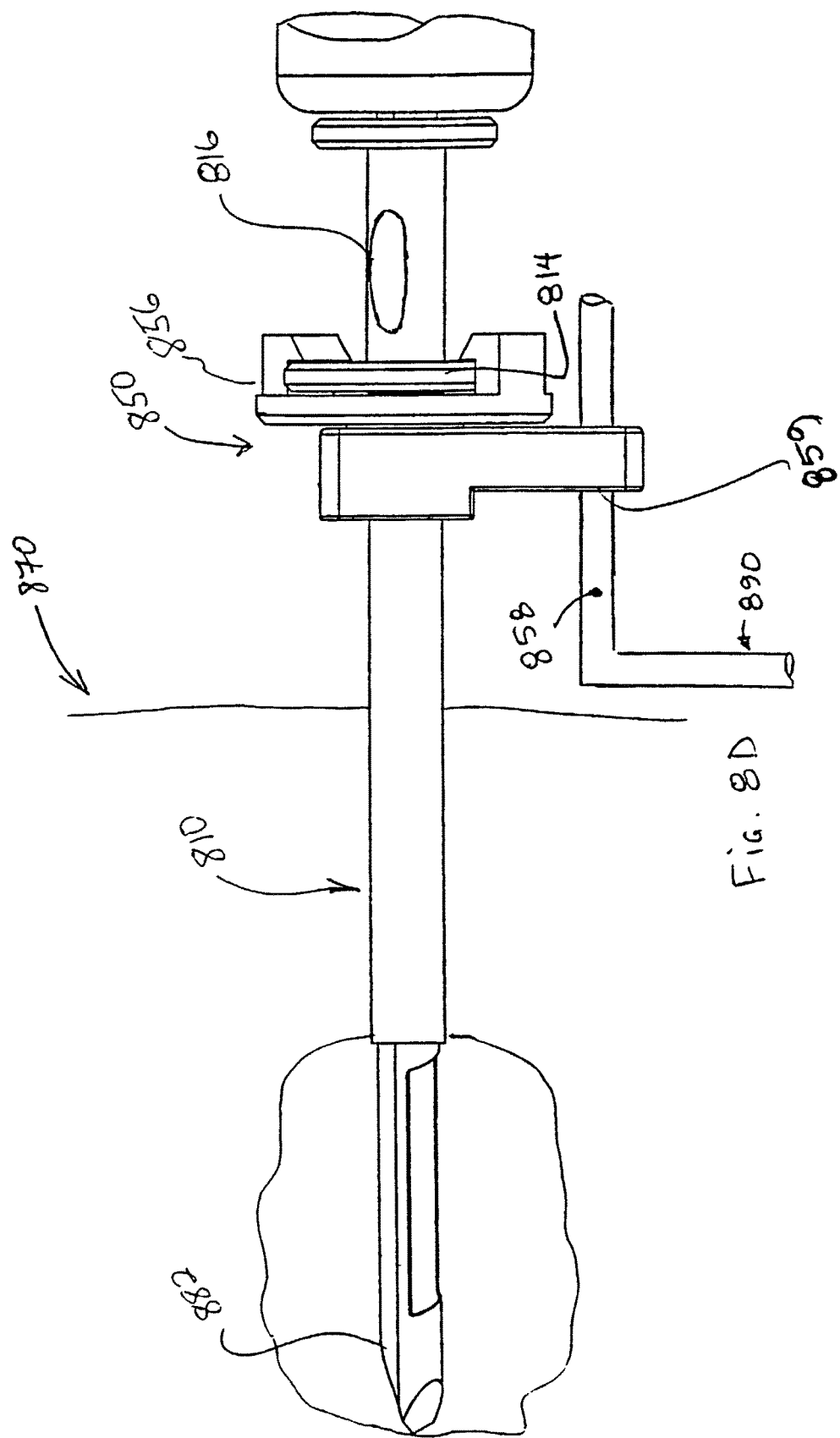

As shown in FIG. 8D, while the probe 882 and outer sheath 810 are held stationary with respect to the patient 870, the guide 850 is moved from the first fixed point 858, then slid along the outer sheath 810 toward the outer sheath hub 814 to a second fixed point 859 along the rail of the stereotactic table 890. (Alternatively, the second fixed point 859 may be a point on the medical instrument 880 or the patient 870 or other convenient place to keep the outer sheath 810 stationary with respect to the patient 870 during delivery of the marking device.) The guide 850 is connected to the outer sheath hub 814, such as with a friction or snap fit of the locking mechanism 856.

Figure 8E:
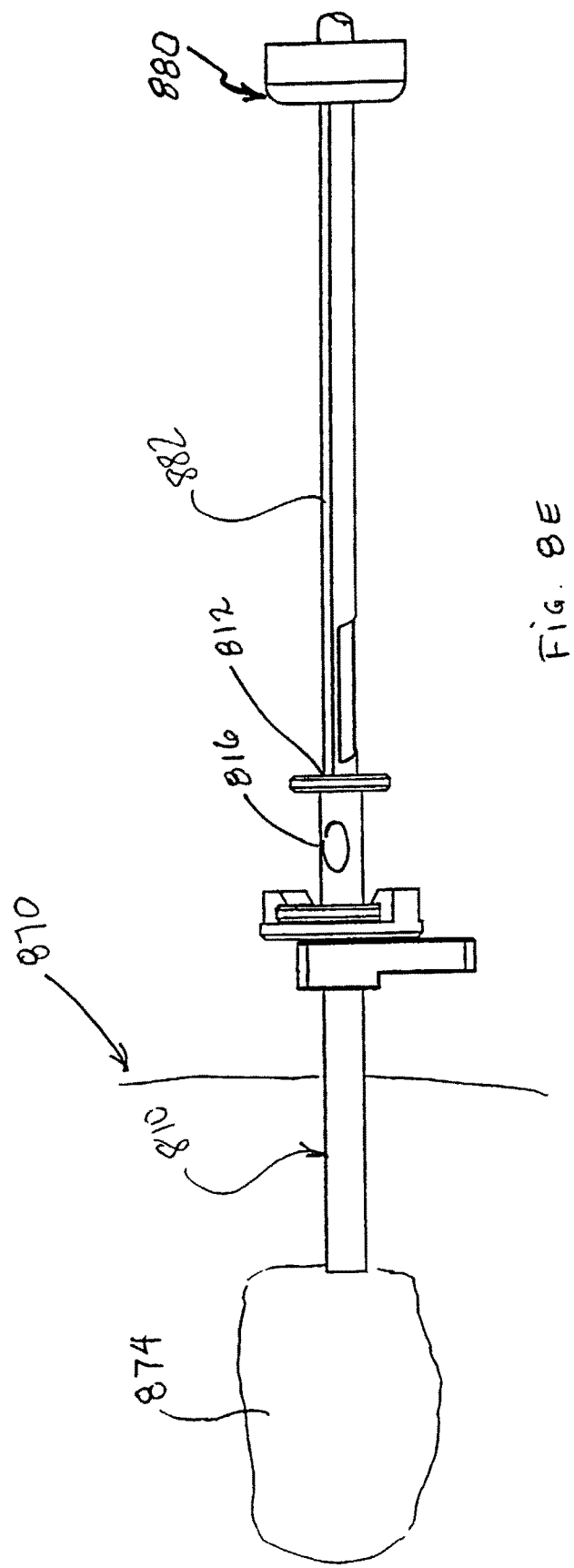

As shown in FIG. 8E, the medical instrument 880 is then at least partly retracted from both the patient 870 and the stationary outer sheath 810, leaving the outer sheath 810 in communication with the biopsy cavity 874. If a side port 816 is used, as shown, the probe 882 may be retracted just far enough to allow access to the cavity through the side port 816; the distal end of the probe 882, which is typically sharp, may remain protected by the proximal end of the outer sheath 810, and is not required to be retracted past the outer sheath entryway 812. However, if a side port 816 is not provided on the outer sheath 810 or is otherwise not used, the probe 882 must be fully retracted to clear the entryway 812. Furthermore, for side port access, the outer sheath 810 may be rotated within the guide 850 to ensure that side port 816 is oriented to be accessible to the operator.

Figure 8F:
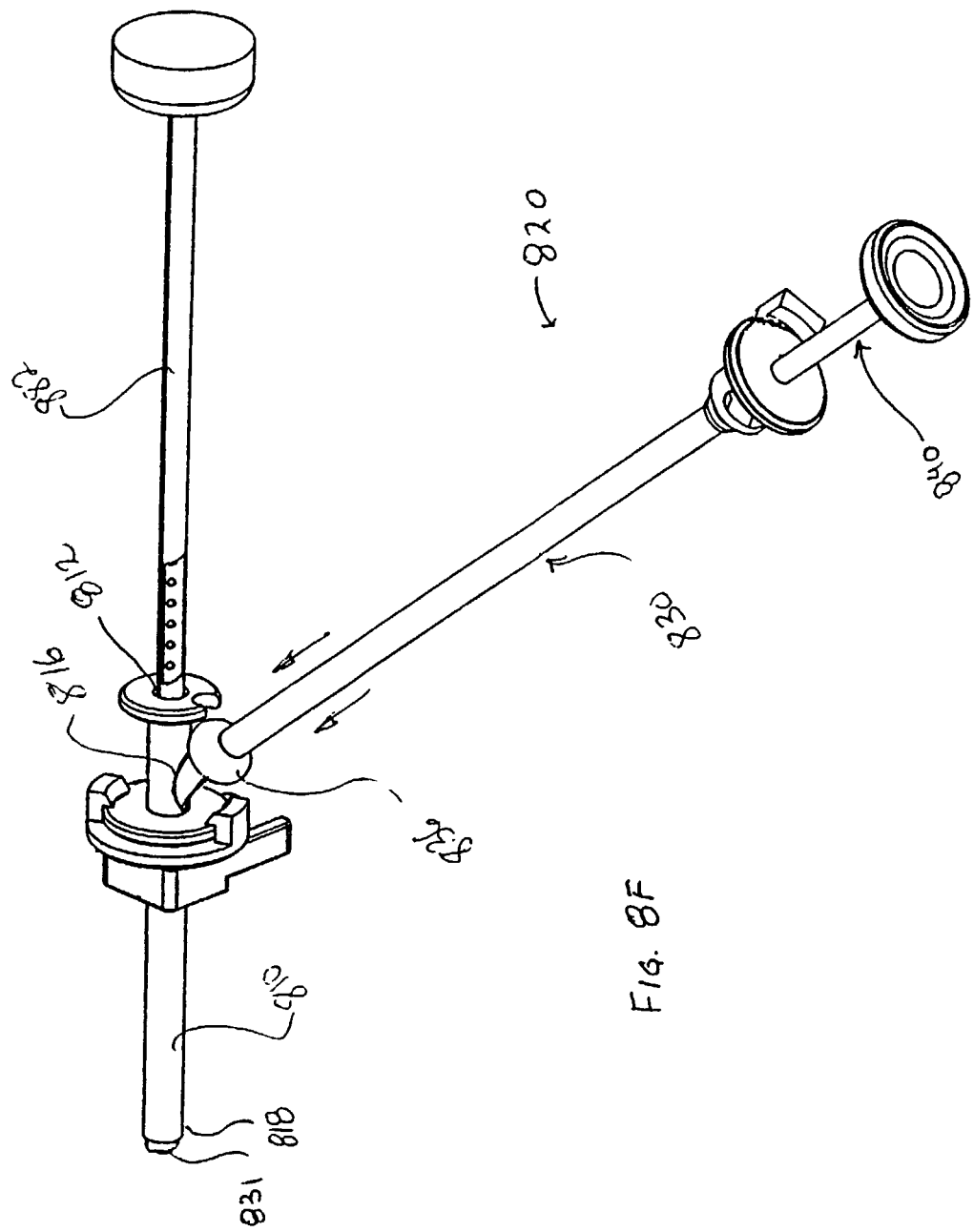

As shown in FIG. 8F, an applicator 820 comprising an inner sheath 830 and a plunger 840 preferably is inserted into a side port 816 of the outer sheath 810 until the stop 836 is reached and the distal end 831 of the inner sheath 830 protrudes through the distal end 818 of the outer sheath 810. The inner sheath 830 is preferably flexible to bend to access the side port 816. Alternatively, it may be preshaped in a bend or curve to access the side port 816. Furthermore, plunger 840 is flexible to access side port 816; it, too, may have a preshaped curve. Alternatively, the probe 882 may be retracted clear of the proximal entryway 812, and the applicator 820 may be inserted through the proximal entryway 812.

Figure 8I:
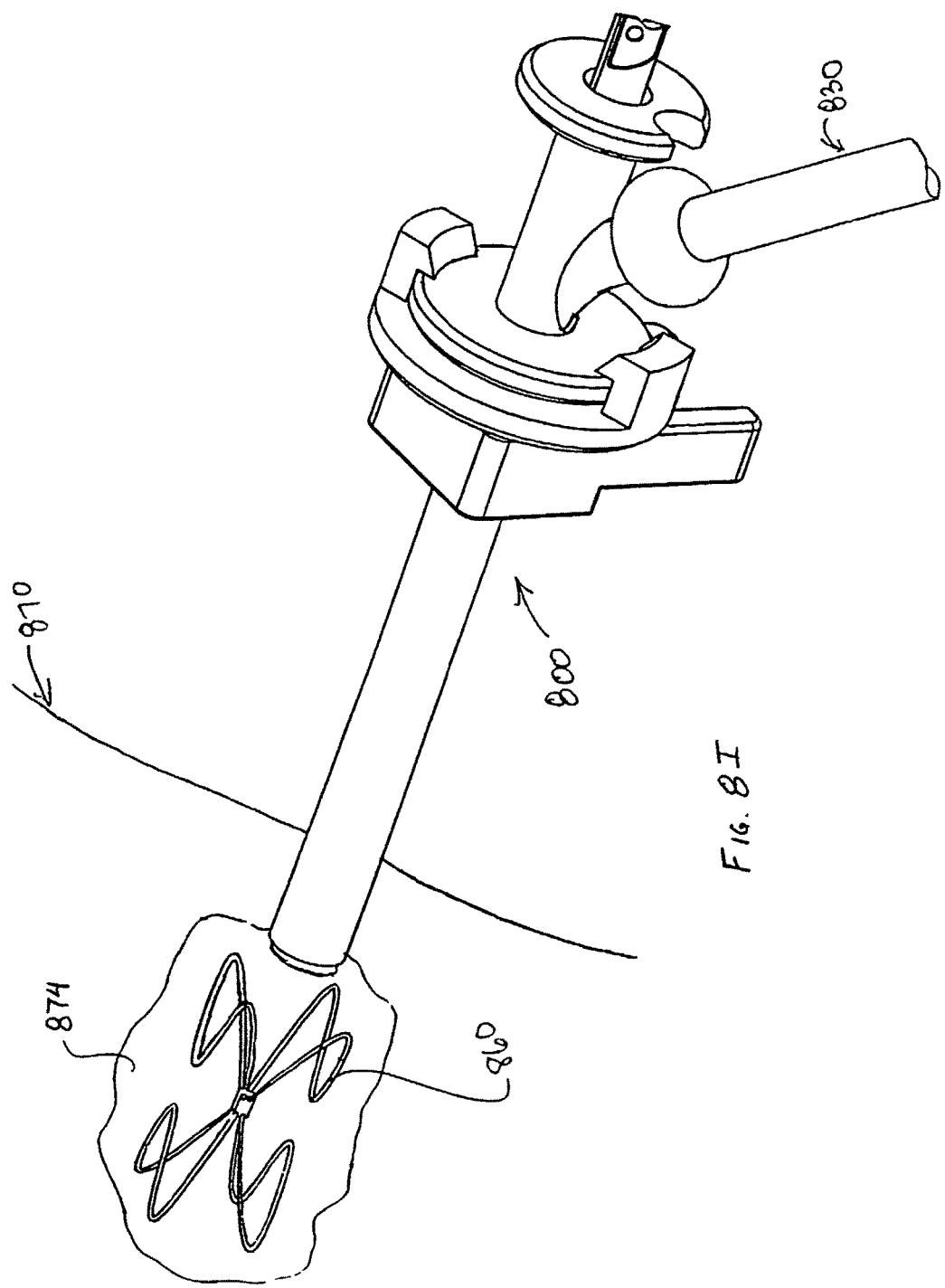

FIGS. 8G-8I illustrate deploying the marking device 860. As shown by the arrow in FIG. 8G, a safety lock 834 is unlocked by depressing a safety tab 835 on the applicator 820 to release the plunger 840. The plunger 840 is pushed into the inner sheath 830, as shown by the arrow in FIG. 8H, to deploy the preloaded marking device 860 into the tissue cavity 874, as shown in FIG. 8I. Although not shown, a Luer or other type fitting may be provided on the delivery device for fluid infusion. The delivery device 800 is removed from the patient 870.

The delivery device of FIGS. 8A-8I may be used to deliver a marking device to a surgically-created cavity by introducing the distal end of the outer sheath through the surgical incision and into the cavity.

FIGS. 9A-9F illustrate a delivery device 900 and a method for using it to deliver a marking device 960 to a tissue cavity 974 laterally through a side window 986 of a cannula 982 of a medical instrument 980. (See FIG. 9D.) Although the marking device 960 is shown as the type shown in FIG. 1K, it is not limited to such, and may be of any type disclosed in this application or any other type known in the art. It is preferably implantable without needing to be removed. The medical instrument 980 may be a biopsy device as described above, or may be any other medical instrument having a cannula 982 with an entryway 988 through which the delivery device 900 can enter, a stop 984 that can limit travel of the delivery device 900, and a side window 986 proximate the distal end 985 through which the marking device 960 can be deployed. The probe 982 is preferably between 1 and 25 mm in its largest cross sectional thickness (diameter, if circular), and most preferably has an inner diameter of 2.5 to 4 mm. The stop 984 may completely or only partially block the distal end 985 of the cannula 982 or may be located elsewhere to limit travel of the delivery device 900.

Figure 9A:
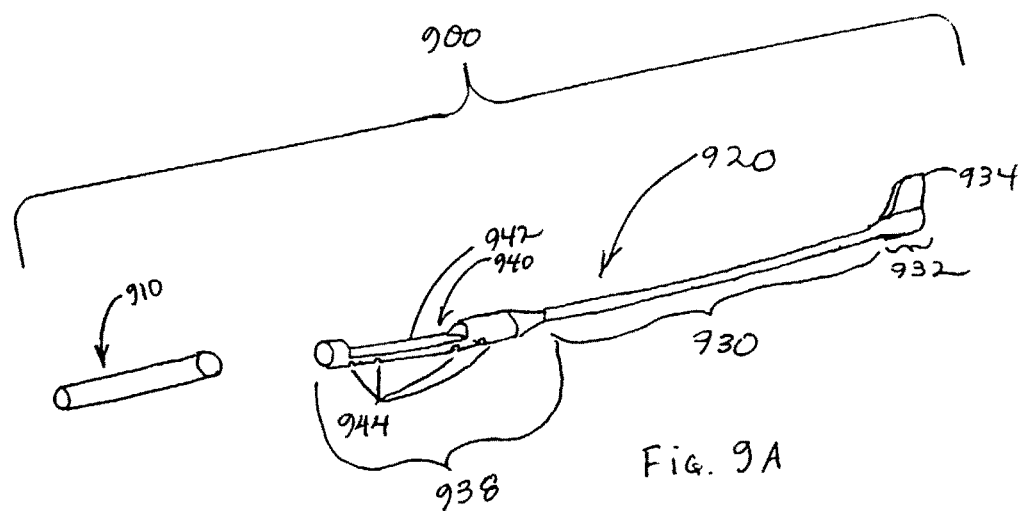
Figure 9B:
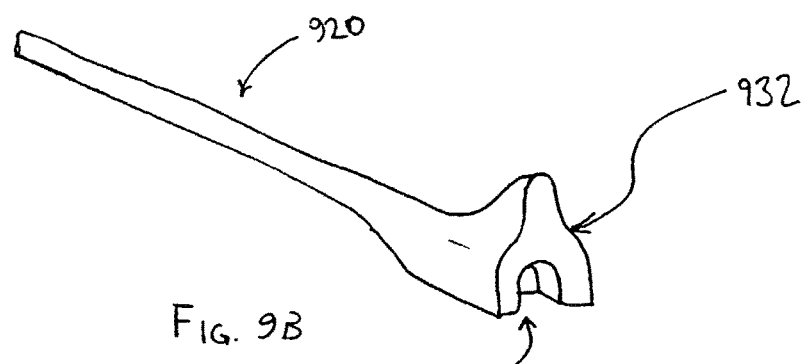
Figure 9C:
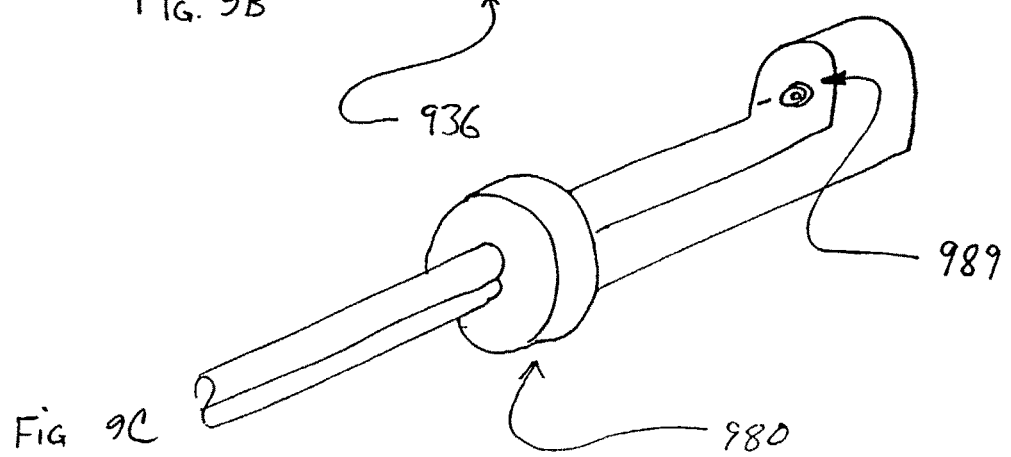

As shown in FIGS. 9A-9B and by way of example, the delivery device 900 preferably includes a shaft 920, which has a flexible shaft portion 930, a proximal handle portion 932, a rotational position indicator 934, and a cutout 936 in the proximal handle portion 932 for mating with a feature 989 of the medical instrument 980 (shown in FIG. 9C). This feature 989 may be the tip of a slidable rod that aids in ejecting a tissue sample from the medical instrument 980, which in this case is shown as a biopsy instrument. As shown in FIGS. 9D-9F, the flexible shaft portion 930 is flexible enough in bending to allow it to be introduced through the entryway 988 of the cannula 982 of the medical instrument 980, yet stiff enough in compression to allow it to be pushed through the cannula 982. Distal of the flexible shaft portion 930 is a distal shaft portion 938, comprising an ejector 940 having a seat 942 on which the preloaded marking device 960 (shown in FIG. 9D) rests prior to delivery and from which the marking device 960 is ejected laterally through the side window 986 of the cannula 982 (shown in FIG. 9F). The ejector 940 further comprises one or more living hinges 944. The entire shaft 920 except for the proximal handle portion 932 is sized to fit through the cannula 982 of the medical instrument 980 (shown in FIG. 9E), and is preferably molded or machined of only one material, such as polypropylene, nylon, or acetal (Delrin®). The flexible shaft portion 930 is more flexible than the proximal portion of the ejector 940. This flexibility may be brought about by varying thickness (using a flexible shaft portion 930 that is thinner, or smaller diameter, if the shaft is round, than the thickness or diameter of the proximal portion of the ejector 940). Alternatively, this greater flexibility may be obtained by varying the shape of the cross section. As another alternative, this greater flexibility may be obtained by using a more flexible material for the flexible shaft portion 930 than for the proximal portion of the ejector 940. As yet another alternative, the section desired to be less flexible may be laminated with a stiff tubing.

As shown in FIG. 9D, to use the delivery device 900, the cannula 982 of the medical instrument 980 is introduced through the skin 972 of the patient 970 and into the site where the marking device 960 is to be deployed. As described before, this step may comprise taking a tissue sample, thus creating a cavity 974 in the tissue. In that case, the side window 986 and lumen of the cannula 982 are then cleared of tissue debris, such as by applying a vacuum; additionally, the cannula may be flushed with saline, which is then aspirated. The shaft 920 is preloaded with a marking device 960, which sits in the seat 942. The marking device 960 is preferably held in place by a retainer 910, which may comprise a tube (as shown), a block, a clip, or the like. In the case where the retainer 910 is a tube, it is preferably made of polyethylene teraphthalate (PET). Furthermore, the seat 942 itself may be designed to provide substantial friction between it and the marking device 960 to help retain the marking device 960 within the seat 942. In fact, the retainer 910, while preferable, is not essential. The friction between the marking device 960 and seat 942 may be increased by adding texture to the surface of the seat 942 and/or by furnishing a seat of a size and shape to provide an interference fit between the marking device 960 and the seat 942.

As shown in FIG. 9E, the distal end of the shaft 920 is placed through the cannula entryway 988 and aligned so that the marking device 960 is in line with the side window 986. The rotational position indicator 934 in proximal handle portion 932 aids in determining the orientation of the marking device 960. In the case where the retainer 910 is a tube, block, clip, or the like, the retainer 910 may be transient as shown, sliding toward the proximal end of the shaft 920 as the delivery device 900 enters the cannula 982. The marking device 960 remains captured between the seat 942 and the cannula 982 as the shaft 920 with marking device 960 is slid through the cannula 982. This differs from some of the prior art clipping devices that are carried on a wire that must be cut when the clip reaches its intended location.

As shown in FIG. 9F, using the proximal handle portion 932, the shaft 920 is advanced so that the distal end of the shaft 920 contacts the cannula stop 984. Advancement of the shaft 920 continues until the ejector 940 ejects the marking device 960 from the seat 942, through the cannula side window 986, and into the tissue cavity 974. As shown here, the ejection step may occur by buckling the shaft 920 in the region of the ejector 940, pushing the seat 942 toward the cannula side window 986. This may be facilitated by using one or more living hinges 944. A cutout 936 in the proximal handle portion 932 may be mated with a mating feature 989 in the medical instrument 980 to indicate that the shaft 920 is in the correct position such that the ejector 940 has ejected the marking device 960. Preferably, the ejector 940 remains completely within the cannula 982 without any portion of it passing through the side window 986. This helps to ensure that the marking device 960 is delivered directly out of the side window 986 without pushing it to some unknown location further away. The retainer 910 may comprise a tube having a slit 912 or other means of expanding its proximal end to fit over the proximal handle portion 932. The retainer 910 preferably remains captured on the shaft 920 between the proximal handle portion 932 and the cannula entryway 988. Although not shown, after the marking device 960 has been ejected through the side window 986, the cannula 982 preferably is rotated about 180° so that the side window 986 is away from the deployed marking device 960. The medical instrument 980 and delivery device 900 are then retracted from the patient 980. Preferably, the ejector 940 is designed to substantially cover the window 986 of the medical instrument 980 to prevent drag on and/or injury to tissue or the marking device on the way out.

FIGS. 10A-10H illustrate an alternative delivery device 1000 and method for using it to deliver a marking device 1060 to a tissue cavity 1074 laterally through the side window 1086 of a cannula 1082 of a medical instrument 1080. The delivery device 1000 is similar to that of delivery device 900 in that its main features are (1) an ejector seat for holding and ejecting a marking device laterally through a side window while remaining within the cannula and (2) a flexible shaft for pushing the ejector seat and marking device through the cannula. The medical instrument 1080 may be a biopsy device as described above, or may be any device having a cannula 1082 with an entryway 1088 through which the delivery device 1000 can enter, and a side window 1086 proximate the distal end 1085 through which the marking device 1060 can be deployed. The cannula 1082, and therefore the portion of the delivery device sliding through cannula 1082, is preferably between 1 and 25 mm in its largest cross sectional thickness (diameter, if circular), and most preferably has an inner diameter of 1.5 to 4.5 mm. In a preferred embodiment, cannula 1082 has an inner diameter of about 2.7 mm, allowing delivery of a marking device 1060 having a compressed diameter of about 2.5 mm. Although the marking device 1060 is shown as the type shown in FIG. 1L, it is not limited to such, and may be of any type disclosed in this application or any other type known in the art. The marking device 1060 is preferably one that can be simply released into the marking site without requiring clipping or piercing tissue.

Figure 10C:
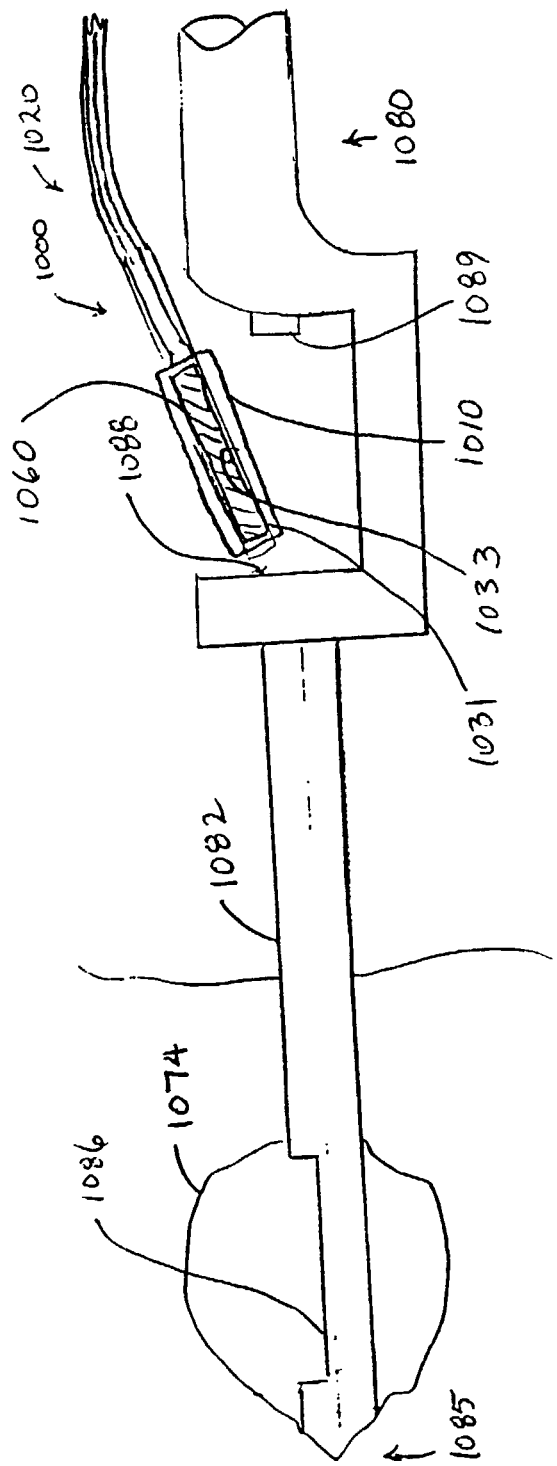

As shown in FIG. 10A, the delivery device 1000 includes an applicator 1020, which has a sheath 1030 and a plunger 1040. A portion of sheath 1030 and a portion of plunger 1040 together form a flexible shaft portion 1022, which can bend to fit through entryway 1088 and is rigid enough to push the ejector seat with its marking device through the cannula 1082. The sheath 1030 further comprises a proximal handle portion 1032 and a collapsible sleeve 1031 at or near its distal end. As shown in FIG. 10B, sleeve 1031 forms an ejector seat 1033, preferably U-shaped, in its collapsed condition on which the preloaded marking device 1060 rests prior to delivery and from which the marking device 1060 is ejected through the side window 1086 of the cannula 1082 (shown in FIG. 10C). The sleeve 1031 is preferably made of a high yield strength plastic such as PET, polyimide, polycarbonate, or acrylic, and is preferably of a size and shape that the material does not have to yield when expanding to eject the marking device 1060. The sleeve 1031 and distal portion of the sheath 1030 are sized to fit through the cannula 1082 of the medical instrument 1080 (shown in FIG. 10C). The sheath 1030 further comprises a clip 1035 that is preferably immovable on the sheath 1030, and includes one or more features 1036, such as a notch, indentation, recess or hole, to mate with a feature 1089 on the medical instrument 1080 (shown in FIG. 10C). The sheath 1030 is preferably made of Pebax, a fluoropolymer such as Teflon®, or polyethylene, and is preferably radiopaque and/or echogenic. The clip 1035 is preferably made of polycarbonate or polypropylene. The plunger 1040 further comprises a proximal handle portion 1042 and a piston 1045 and is capable of expanding the sleeve 1031 by filling it with an expander 1044, which may be a fluid, such as saline or air, or preferably a solid, such as the distal portion of the piston 1045 as shown. In the case where the expander 1044 is a fluid, the sleeve 1031 may be sealed to form a balloon that keeps the fluid within the delivery device. Alternatively, the sleeve 1031 may have one or more openings (not shown) to allow the fluid to not only expand the sleeve 1031 but to be delivered to the body; this is useful for delivering fluids having hemostatic, pain-reducing, antibiotic, sentinel node-detecting, and/or body-expanding properties; the body expanding properties may work by hydrating or by chemically reacting with the body material. To inject the fluid through the plunger 1040, whether the sleeve 1031 is open or closed, the plunger 1040 may further include a Luer or other type fitting for connection to a fluid reservoir or syringe (not shown). Additionally or alternatively, fluids may be infused through a vacuum system on the medical instrument. In the case where the expander 1044 is a solid, the sleeve 1031 may be open or closed.

As shown in FIG. 10C, to use the delivery device 1000, the cannula 1082 of the medical instrument 1080 is introduced into the site where the marking device 1060 is to be deployed; as described before, this step may comprise taking a tissue sample, thus creating a cavity 1074 in the tissue. The side window 1086 and lumen of the cannula 1082 are preferably cleared of tissue debris, such as by applying a vacuum; additionally, the cannula may be flushed with saline, which is then aspirated. The applicator 1020 is preloaded with a marking device 1060, which sits in the ejector seat 1033 formed in the collapsed sleeve 1031. It is held in place by a retainer 1010, which may be a tube (as shown), a block, a clip, or the like, of a size that will not pass through the cannula 1082.

Figure 10D:
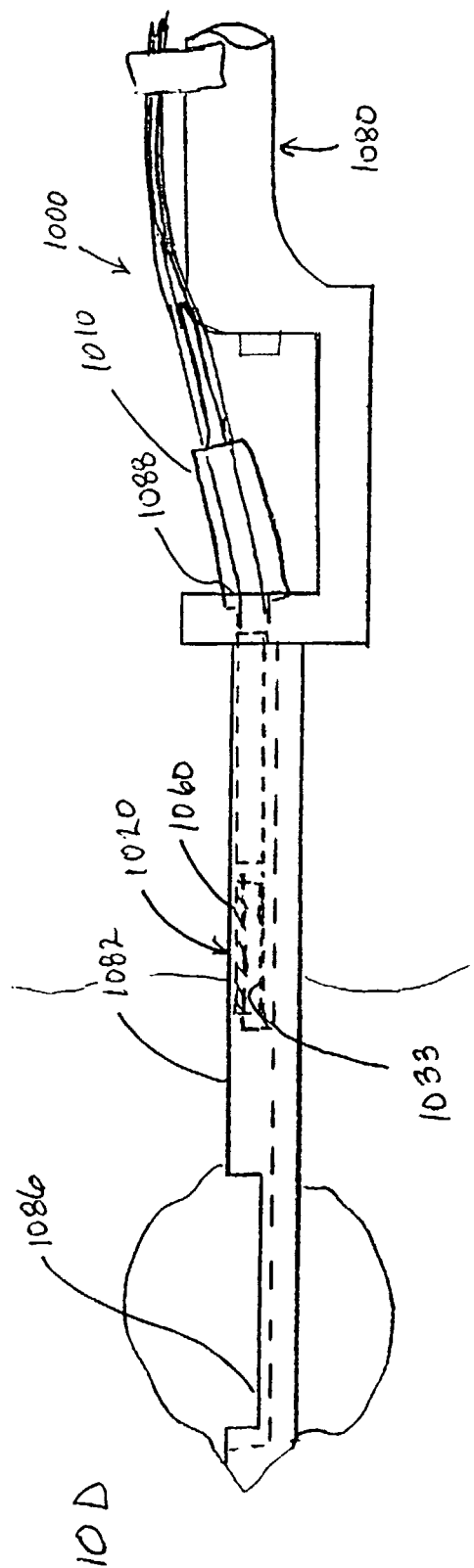

As shown in FIG. 10D, the distal end of the applicator 1020 is placed through the cannula entryway 1088 and aligned so that the marking device 1060 is in line with the side window 1086. This alignment can be achieved by ensuring that the side window 1086 is in its "12 o'clock" rotational position, as shown, and orienting the marking device 1060 so that it is facing the same direction as the side window 1086 and so that the clip 1035 with its mating feature(s) 1036 will match up with the feature 1089 on the medical instrument 1080. Because the retainer 1010 cannot pass through the cannula 1082, it is a transient retainer and does not remain in place to hold the marking device 1060 in seat 1033; as the delivery device 1000 enters the cannula 1082, the retainer 1010 is slid off the marking device 1060 and remains outside the cannula 1082. The marking device 1060 remains captured between the seat 1033 and the cannula 1082 as the applicator 1020 with its marking device 1060 is slid through the cannula 1082.

As shown in FIGS. 10E-10H, the applicator 1020 is advanced until the clip 1035 on the sheath 1030 abuts the proximal end of the retainer 1010, thus capturing the retainer 1010 between the clip 1035 and the cannula entryway 1088. The clip 1035 is then clipped onto the medical instrument 1080 by mating the clip and medical instrument features, 1036 and 1089. The plunger 1040 is then pushed until the expander 1044 expands the sleeve 1031, ejecting the marking device 1060 from the seat 1033, through the cannula side window 1086, and into the tissue cavity 1074. Preferably, all parts of the applicator 1020 that enter the cannula 1082 remain completely within the cannula 1082 without any portion passing through the side window 1086. This helps to ensure that the marking device 1060 is delivered directly out of the side window 1086 without pushing it to some unknown location further away. As shown in FIG. 10G-10H, after the marking device 1060 has been ejected through the side window 1086, the cannula 1082 is preferably rotated about 180° so that the side window 1086 is away from the deployed marking device 1060. This guarantees that only a smooth, non-cutting side of the cannula faces the marking device 1060 during withdrawal of the medical instrument 1080 to avoid dislodging the marking device 1060. Furthermore, an advantage of this system is that once the sleeve is expanded it substantially covers the side window thus protecting the tissue. In fact, prior art through-cannula clip delivery devices typically require extra steps of withdrawing the clip applier and reinserting an inner cannula to protect the tissue from the sharp window and to avoid dislodging the clip. The medical instrument 1080 and delivery device 1000 are then retracted from the patient 1070.

FIGS. 11A-11E illustrate an alternative delivery device 1100 and method for using it to deliver a marking device 1160 to a tissue cavity 1174 laterally through the side window 1186 of a cannula 1182 of a medical instrument 1180. The medical instrument 1180 is preferably a biopsy device as described above, or may be any device having a cannula 1182 with an entryway 1188 through which the delivery device 1100 can enter, and a side window 1186 proximate the distal end 1185 through which the marking device 1160 can be deployed. Although the marking device 1160 is preferably the type shown in FIG. 1L, it is not limited to such, and may be of any type disclosed in this application or any other known in the art. Marking device 1160 is preferably implantable and can be left in the body indefinitely.

As shown in FIG. 11A, the delivery device 1100 includes an applicator 1120, which has a sheath 1130 and a plunger 1140. A portion of the sheath 1130 and a portion of the plunger 1140 together form a form a flexible shaft portion 1122, which can bend to fit through entryway 1188 and is rigid enough to push the ejector seat with its marking device through the cannula 1182. The sheath 1130 further comprises a proximal handle portion 1132 and a collapsible sleeve 1131 that forms an ejector seat 1133 in its collapsed condition (similar to seat 1033 shown in FIG. 10B) on which the preloaded marking device 1160 (shown in FIG. 11C) rests prior to delivery and from which the marking device 1160 is ejected through the side window 1186 of the cannula 1182. The sleeve 1131 is preferably made of a high yield strength plastic such as PET, polyimide, polycarbonate, or acrylic, and is preferably of a size and shape that the material does not have to yield when expanding to eject the marking device 1160. The sheath 1130 further comprises a clip 1135 that is immovable thereon, having a clip feature 1136. The plunger 1140 further comprises a proximal handle portion 1142 and a piston 1145 and is capable of expanding the sleeve 1131 by filling it with an expander 1144, which may be a fluid, such as saline or air, or preferably a solid, such as the distal end of piston 1145 as shown. In the case where the expander 1144 is a fluid, the sleeve 1131 is sealed to form a balloon. Alternatively, the sleeve 1131 may have one or more openings (not shown) to allow the fluid to not only expand the sleeve 1131 but to be delivered to the body; this is useful for delivering fluids having hemostatic, pain-reducing, antibiotic, sentinel node-detecting, and/or body-expanding properties; the body expanding properties may work by hydrating or by chemically reacting with the body material. In the case where the expander 1144 is a solid, the sleeve 1131 may be open- or closed-ended. A separate fitting may be provided on the sheath 1130 for drug or saline infusion through the sheath 1130. The distal end of the applicator 1020 is sized to fit through the cannula 1182 of the medical instrument 1180 (shown in FIG. 11C). The delivery device 1100 further includes a retainer 1110 having a key on its distal end for locking into a keyway 1183 in the cannula 1182 (shown in FIG. 11B). The retainer 1110 further includes a hub 1114 at or near its proximal end with a feature 1115 for connecting to the clip feature 1136 on the sheath clip 1135.

As shown in FIG. 11C, to use the delivery device 1100, the cannula 1182 of the medical instrument 1180 is introduced into the site where the marking device 1160 is to be deployed; as described before, this step may comprise taking a tissue sample, thus creating a cavity 1174 in the tissue. The side window 1186 and lumen of the cannula 1182 are preferably cleared of tissue debris, such as by applying a vacuum; additionally, the cannula may be flushed with saline, which is then aspirated. The applicator 1120 is preloaded with a marking device 1160, which sits in the seat 1133 (see seat 1033 in FIG. 10B) formed in the collapsed sleeve 1131. It is held in place by the retainer 1110, which may be a tube (as shown), a block, a clip, or the like. As will be seen later, it is not necessary that the side window 1186 of the cannula 1182 be in its "12 o'clock" position to align the marking device 1160 with the side window 1186. The keyway 1183 rotates with the cannula 1182, and therefore is in line with the side window 1186.

As shown in FIG. 11D, the distal end of the applicator 1120 and retainer 1110 are placed through the cannula entryway 1188 and aligned so that the retainer key 1112 enters keyway 1183 of the cannula 1182. As the delivery device 1100 enters the cannula 1182, the retainer 1110 is slid off the marking device 1160. The applicator 1020 is pushed forward, aligning the feature 1136 in the sheath clip 1135 with the feature 1115 in the retainer hub 1114 and connecting them together, thus capturing the retainer 1110 between the cannula entryway 1188 and the sheath clip 1135. By locking the sheath clip 1135 to the retainer hub 1114, and because the retainer 1110 is locked into the keyway 1183 and is therefore rotationally fixed with respect to the cannula 1182, the marking device 1160 will always face the direction that the side window 1186 is facing. Therefore, the marking device 1160 may be delivered when the medical instrument 1180 has its cannula 1182 and side window 1186 in any clock position, and is not limited to delivering in only the 12 o'clock position. The marking device 1160 remains captured between the seat 1133 and the cannula 1182 as the applicator 1120 with its marking device 1160 is slid through the cannula 1182.

As shown in FIG. 11E, the safety lock 1134 on the proximal handle portion 1132 is then unlocked, and the plunger 1140 is pushed until the expander 1144 expands the sleeve 1131, ejecting the marking device 1160 from the seat 1133, through the cannula side window 1186, and into the tissue cavity 1174. Preferably, all parts of the applicator 1120 that enter the cannula 1182 remain completely within the cannula 1182 without any portion passing through the side window 1186. This helps to ensure that the marking device 1160 is delivered directly out of the side window 1186 without pushing it to some unknown location further away. After the marking device 1160 has been ejected through the side window 1186, the cannula 1182 is rotated about 180° so that the side window 1186 is away from the deployed marking device 1160. As with delivery device 1000, an advantage of delivery device 1100 is that once the sleeve is expanded it substantially covers the side window 1186 thus protecting the tissue. The medical instrument 1180 and delivery device 1100 are then retracted from the patient 1170.

As can be seen from the embodiments of FIGS. 9A-9F, 10A-10G, and 11A-11E, delivery of a marking device into a cavity through a window provides several advantages. As examples, the track created is only as large as the cannula used to create the cavity, the number of steps in the procedure is reduced because the site is positively located by the cannula itself and does not have to be relocated, and the marking device will be delivered to the correct location.

From the foregoing, it is understood that the invention provides an improved subcutaneous cavity marking device and method. While the above descriptions have described the invention for use in the marking of biopsy cavities, the invention is not limited to such. One such application is evident as the invention may further be used as a lumpectomy site marker. In this use, the cavity marking device yields an improved benefit by marking the perimeter of the lumpectomy cavity. Other such applications of the invention include delivering a marker to a naturally occurring body cavity and delivering a marker to an area of tissue that does not have a cavity. Furthermore, although some of the embodiments described herein were described with respect to a percutaneous procedure, they may be used in an open surgical procedure as well; in that case, the marking device may be delivered by hand without the use of a delivery system, and the marking device may not require compression for delivery through a small opening. Also, the marking system may be provided as a kit. wherein the marking device is preloaded in the delivery device; alternatively, the marking device may be provided separately for loading into the delivery device by the operator, with or without the aid of a loading tool, which also may be provided in the kit. The kit may be provided with variously sized and/or variously shaped marking devices, allowing the operator to choose the particular device most suited for the cavity to be marked. Having more than one marking device available in the kit also allows the operator to mark more than one location, if needed.

Furthermore, as will be described with respect to FIGS. 12A-12C and 13A-13B, the present invention provides an alternative composition and method to remotely detect sentinel lymph nodes to determine whether cancerous cells have spread thereto. This method includes the deposition, preferably by one of the delivery devices described herein or by injection via a thin needle applicator, of a remotely detectable contrast agent that migrates to the SN. Upon accumulating in the SN, the remotely detectable contrast agent allows a physician to pinpoint the location of the SN to target the SN for removal using minimally invasive techniques. The composition is preferably capable of migrating from breast tissue to a lymph node in a predetermined amount of time. Preferably, less than 3 hours, and more preferably within 5 to 20 minutes. To migrate within this timeframe, the contrast agent preferably comprises particles between 0.05 microns and 5 microns in diameter. The composition and method eliminates the need for potentially toxic radioactive tracer material. In addition, the lack of toxicity of such agents obviates the need to remove the lesion and/or the SN on the same day. The contrast agent is preferably either permanently implantable or short-lived, never requiring removal.

These agents may be any biologically compatible agents capable of remote detection. Examples of such remote detection include, but are not limited to, magnetism such as a magnetometer, Hall effect sensor, or magnetic resonance imaging (MRI); ultrasound; X ray, fluoroscopy, or CT; thermal means; high intensity ultraviolet techniques; fluorescent dye techniques; etc.; singly or in combination.

One example of such a contrast agent is an echogenic microsphere capable of reflecting ultrasonic energy. These microspheres, preferably averaging typically between 0.2 microns and 5 microns in diameter, and preferably less than 2 microns in diameter, may be mixed with a biologically compatible carrier fluid and injected into the body in the vicinity of the lesion, where they will accumulate in the SN. The echogenic microspheres may comprise hollow bubbles fill with air, $CO_2$, nitrogen, or fluorinated gas. For example, these microbubbles may comprise microencapsulated perfluorocarbon. The echogenic contrast agent may, but does not necessarily, contain microparticles of silicon or a silicon compound, such as silicone or $SiO_2$, preferably in a dilute suspension. Upon an exposure to ultrasonic energy, the spheres reflect the energy creating an ultrasonic reflection. The ultrasonic-reflection resulting from a large number of the microspheres that have accumulated in the SN permits detection of the particular node by a conventional ultrasonic probe. Another example of an agent is a biologically compatible magnetically detectable body such as a magnetic microsphere. Such a magnetically detectable body can be the echogenic microsphere described above that is either fabricated from or coated with a magnetic material; alternatively, it may be a solid or other type of magnetic body capable of being incorporated into a carrier fluid and deposited around the lesion or its cavity as described herein. These bodies should be capable of migration to and accumulation in the SN so that, in a similar fashion to the echogenic microspheres, the cumulative magnetic field presented by these magnetic bodies allows one to remotely and noninvasively determine the location of the SN.

As an alternative or addition to being echogenic, the contrast agent may have sufficient radiopacity to be detectable using fluoroscopy, mammography, or other X ray imaging.

Figure 12A:
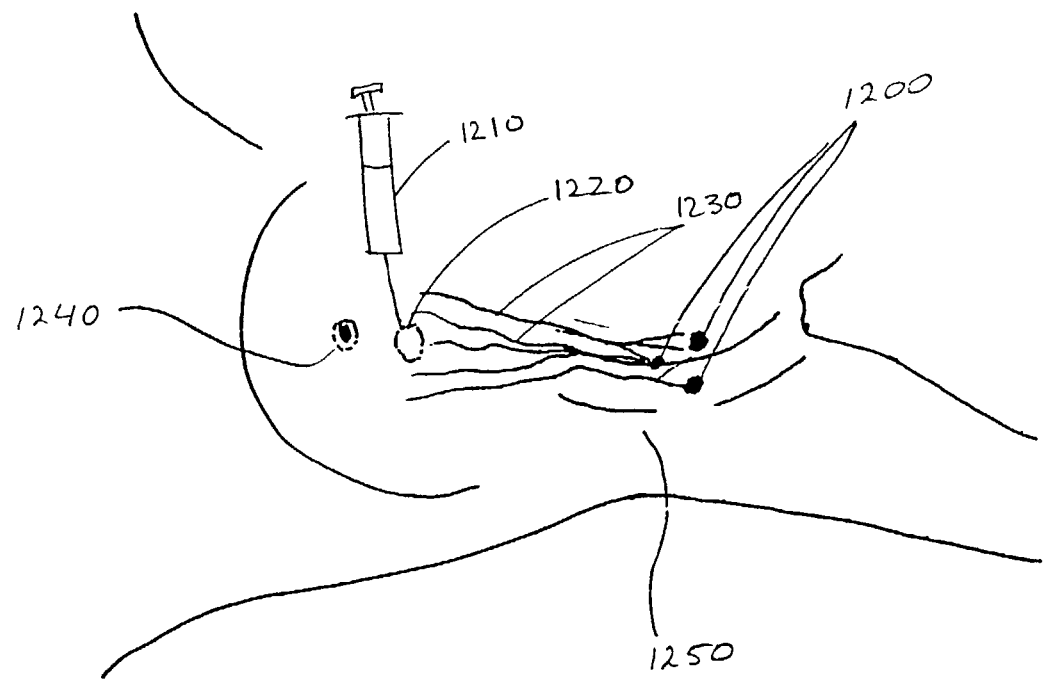
FIGS. 12A-12C illustrate a method for locating a sentinel node.
Figure 12B:
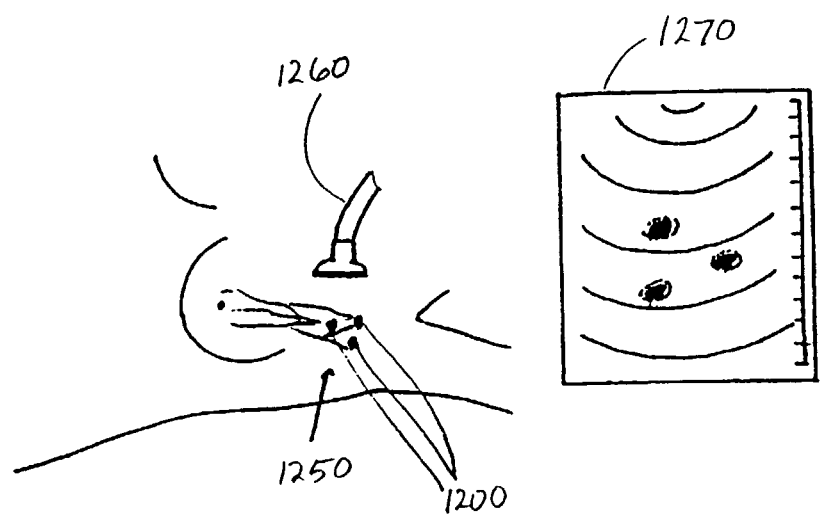
Figure 12C:
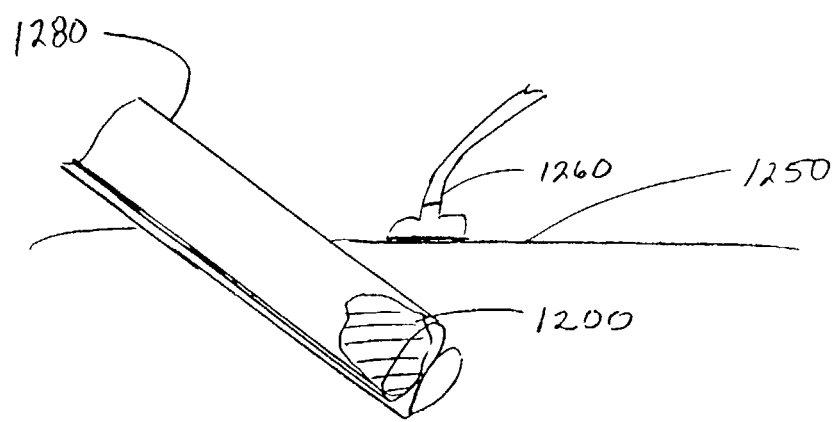

FIGS. 12A-12C show a method for locating the sentinel lymph node in a mammalian body to determine if cancerous cells have spread thereto. The method includes (1) depositing a remotely detectable fluid in or around a lesion for migration to and accumulation in the associated sentinel node and (2) remotely detecting the location of that node with a minimum of trauma and toxicity to the patient. The composition used for locating the sentinel node is preferably a fluid composition consisting of a carrier fluid and some type of non-radioactive contrast agent as described above. Alternatively, the contrast agent may also be a fluid and therefore not require a separate carrier fluid to migrate to the node. This composition is capable of (1) deposition in or around a lesion and migration to and accumulation in the associated sentinel node, and (2) remote detection a noninvasive technique. The composition may additionally be capable of being directly visualized such as by adding blue dye to the noninvasively-detectable contrast agent to confirm that the appropriate lymph node was removed. Carbon may be, but is not necessarily, added to the contrast agent for histological confirmation.

FIG. 12A depicts the first steps of a method for locating a sentinel node 1200 comprising injecting a noninvasively detectable, non-radioactive, migratory contrast agent 1210 into the region of a cavity or lesion 1220, then waiting sufficient time for the contrast agent to migrate through the lymph ducts 1230 to at least one lymph node 1200 in the axillary region 1250. In general, the smaller the particle size of the contrast agent, the faster it will migrate; also, generally less viscous compositions will migrate faster. Furthermore, the closer in the size the particles are to each other, the narrower the window of time will be for most of the particles to reach the sentinel node. The particles may be filtered or otherwise selected to be very close in size; alternatively, they may vary widely; as another alternative, they may have a bimodal size distribution with the smaller size for early sentinel node detection and the larger size for accumulation throughout the lymph nodes, as will be described below. The contrast agent may be injected directly into a biopsy or lumpectomy cavity; or it may be injected intradermally or periareolarly (around the area of the areola 1240), before, after, or without creation of a cavity. While waiting for the contrast agent to migrate, massage and/or compression may be administered to the patient to speed migration of the contrast. Also, a biopsy or lumpectomy may be performed during the waiting period, if not already done (not shown). This latter order of steps may be preferred by some who believe that creating the cavity may disturb the lymph ducts 1230, slowing down or preventing migration of the contrast agent to the sentinel node.

As shown in FIG. 12B, the contrast agent 1210 is noninvasively detected in at least one lymph node 1200. Examples of non-invasive detection methods include, but are not limited to using ultrasound, fluoroscopy, MRI, a Hall Effect sensor or magnetometer, or other imaging means. In the embodiment depicted in FIG. 12B, the contrast agent 1210 is echogenic, and an ultrasound probe 1260 is used to scan the axilla 1250 while watching the ultrasound monitor 1270. Preferably, only one lymph node is identified as containing contrast agent and, therefore, is the "sentinel node"; however, the contrast agent may accumulate in 2 or 3 lymph nodes almost simultaneously, with up to 3 being considered "sentinel nodes", as shown. Particularly for contrast agents having a low viscosity and a uniformly small size, such as an average of less than 0.05 microns and an upper limit of 0.1 microns. Given this configuration, lymphatic system will quickly take up the contrast agent. The contrast agent will then quickly migrate to the sentinel node, then to the next node and so on. In that case, the physician must be careful to not wait too long between injection and detection.

As shown in FIG. 12C, lymph tissue containing the contrast agent 1200 is then either sampled, using fine needle aspiration (FNA) or core biopsy, or completely removed, percutaneously, endoscopically, laparoscopically, or using conventional surgery. A percutaneous tissue removal device 1280 may be used, such as those described in U.S. Pat. Nos. 5,913,857 and 5,810,806 and U.S. application Ser. Nos. 09/184,766 and 09/145,487 to Vivant Medical, Inc. The tissue sampling or removal is preferably done using ultrasound, especially in the case where ultrasound is used to detect the contrast agent. The ultrasound probe 1260 held over the sentinel node 1200 that was detected in the axilla 1250 while the marked tissue is sampled. Alternatively or additionally, the tissue sampling or removal may be done using fluoroscopy, especially in the case where the contrast agent is radiographic. As another alternative, the tissue sampling or removal may be done using MRI. Many of the prior-art radioactive tracer methods required separate procedures for detecting the sentinel node under the skin, marking the location on the skin with a dot, alternating between a gamma probe and an ultrasound probe to mark the SN with a wire, then surgically removing the SN and wire. However, in the present invention, it is desirable to use the same imaging modality to detect the sentinel node and to sample or remove it. Following the sentinel lymph node sampling or removal, the patient may be noninvasively checked to see whether all the contrast was removed. However, it is preferable that the contrast be completely implantable, not requiring removal. Furthermore, many of the commercially-available echogenic contrast agents suitable for this method are short-lived, and therefore do not require removal.

The removed tissue is evaluated histologically for cancer. If cancer is found in the sentinel lymph node, the migrating and accumulating properties of the contrast agent can be used to determine where additional lymph nodes are that should be removed. That is, the contrast agent that was used to detect the SN can be one that accumulates quickly in the first node ("sentinel node") for identification within preferably 5 to 20 minutes. The agent will continue to migrate through the lymphatic system, but preferably more slowly, with a portion of the contrast agent accumulating in each lymph node for detecting during a window of approximately 1 day to 1 month following injection. This facilitates detection of additional lymph nodes that the physician may want to remove in the case where cancer is detected in the sentinel node. Removing such lymph nodes may be therapeutic by decreasing the tumor burden, thus increasing the efficacy of subsequent chemotherapy. The lymph nodes preferably are removed percutaneously using image guidance of the same modality used to detect them.

Figure 13A:
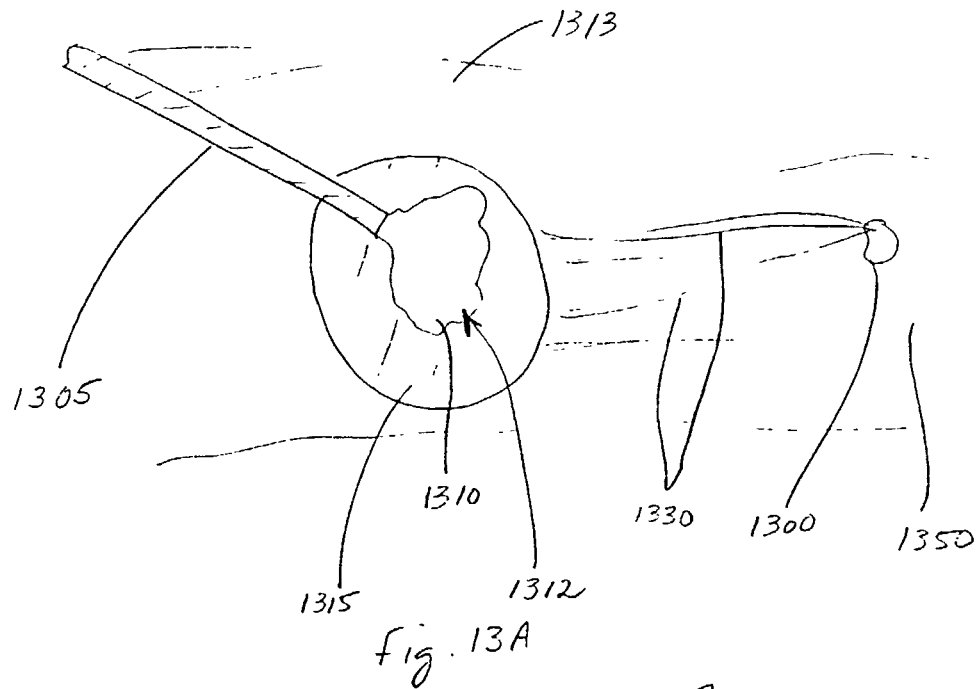
FIGS. 13A-13B illustrate a method for marking a biopsy or lumpectomy cavity and locating a sentinel node.
Figure 13B:
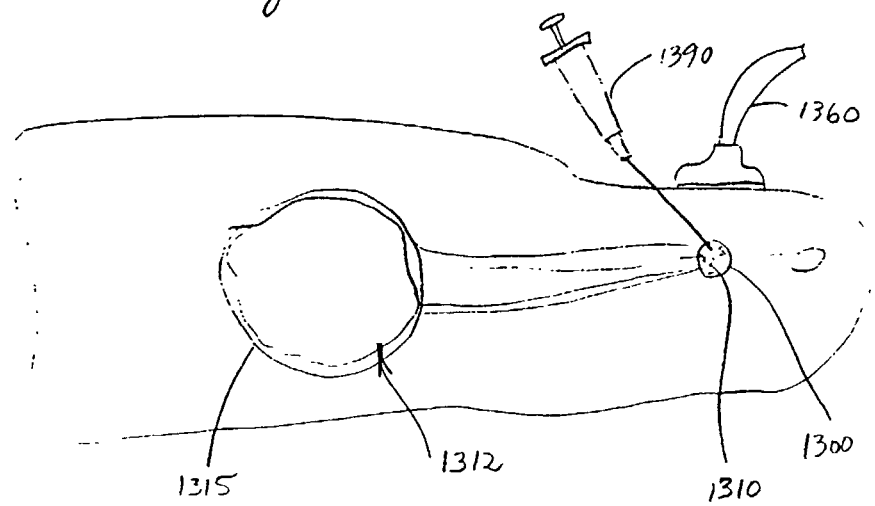

FIGS. 13A-13B show a method for marking a biopsy or lumpectomy cavity and locating the sentinel lymph node that had served the tissue removed from the cavity to determine if cancerous cells have spread thereto. The composition for locating the sentinel lymph node is preferably a fluid composition consisting of a carrier fluid and some type of contrast agent as described above; alternatively, the contrast agent may itself be a fluid and therefore not need a separate carrier fluid. This composition is capable of (1) deposition in or around a lesion and migration to and accumulation in the associated sentinel node, and (2) detection, preferably by noninvasive means, and/or by direct visualization. Also disclosed is a method for marking a cavity and detecting the location of a sentinel node by (1) depositing a marking device with a detectable composition in the cavity for migration to and accumulation in the associated sentinel node and (2) detecting the location of that node with a minimum of trauma and toxicity to the patient.

FIG. 13A depicts the first steps of a method for marking a biopsy or lumpectomy cavity 1315 in the breast 1313 and locating a sentinel node 1300 in the axilla 1350, comprising inserting a subcutaneous marking device 1312 according to the present invention and using a delivery device 1305 according to the present invention. A contrast agent 1310 is included in the marking device 1312, either as the body of the marking device (as shown), which may degrade, allowing detectable microparticles to migrate to the lymph nodes. Alternatively, the contrast agent 1310 as a separate composition that is added to the marking device, before, during, or after its insertion into the cavity (e.g., see FIGS. 4D-4I, 10A-10H, and 11A-11E). Following marking device/contrast agent insertion, while waiting for the contrast agent to migrate to a lymph node, massage and/or compression may be administered to the patient to speed migration of the contrast.

In a similar manner as depicted in FIG. 12B, the contrast agent is noninvasively detected in at least one lymph node. Examples of such non-invasive methods includes, but are not limited to, ultrasound, fluoroscopy, MRI, or a Hall Effect sensor or magnetometer, or other imaging. The imaging used to detect the contrast agent may be, but is not necessarily, the same as that used to detect the cavity marking device.

As shown in FIG. 13B, lymph tissue containing the contrast agent is then either sampled, using fine needle aspiration (FNA) (shown here) or core biopsy, or completely removed, endoscopically, laparoscopically, or using conventional surgery. As shown in this example, marking device 1312 has expanded to fill cavity 1315. Some of the contrast agent 1310 has migrated away from the marking device 1312 and has accumulated in the sentinel node 1300, where an ultrasound probe 1360 is used to guide a needle 1390 for fine needle aspiration. As described above, the tissue sampling or removal may be done using ultrasound, fluoroscopy, MRI, or any other suitable imaging technique. Alternatively, the contrast agent may be visible under direct visualization, and the tissue may be surgically removed without any image guidance. As another alternative, the contrast agent may be a radioactive tracer, and a gamma probe and/or lymphoscintigraphy may be used in combination with ultrasound, as described above, to detect and remove the sentinel node. A percutaneous tissue removal device may be used, such as those described in PCT publication WO 99/25248; U.S. Pat. Nos. 5,913,857 and 5,810,806; and U.S. application Ser. Nos. 09/184,766 and 09/145,487 to Vivant Medical, Inc.

Once removed, the tissue sample is evaluated for the presence of cancer. If cancer is found in the sentinel lymph node, the contrast agent can again be used to determine where additional lymph nodes are that should be removed. As described above, a contrast agent can be used that will accumulate quickly in the first node ("sentinel node") for identification within preferably 5 to 20 minutes. The agent will continue to migrate through the lymphatic system, but more slowly, with a portion of the contrast agent accumulating in each lymph node for detecting during a window of approximately 1 day to 1 month following injection. This provides an easy way to detect the additional lymph nodes that may need to be removed in the case where cancer is detected in the sentinel node. The lymph nodes preferably are removed using image guidance of the same modality used to detect them.

The invention herein has been described by examples and a particularly desired way of practicing the invention has been described. However, the invention as claimed herein is not limited to that specific description in any manner. Furthermore, the features described for one embodiment may be combined with other embodiments herein disclosed. Equivalence to the description as hereinafter claimed is considered to be within the scope of protection of this patent.

We claim as our invention:

1. A delivery device for delivering a marking device to a target site, said delivery device comprising:
    an elongate member having a distal portion and a proximal portion with a lumen extending between the distal and proximal portions, said distal portion of said elongate member configured to seat the marking device and advance the marking device within said distal portion to the target site;
    an ejector coupled to said elongate member, said ejector configured to disengage the marking device from said distal portion;
    a marking device preloaded in said elongate member distal portion, for delivery through the lumen;
    wherein said marking device comprises a first component and a second component, the first component is a wound arrangement of bioabsorbable suture material and the second component is a unitary piece of metal forming a marker, wherein the second component is carried and supported by the wound arrangement of the first component, and
    wherein the wound arrangement of the first component includes multiple passes of the suture material through the second component to form a plurality of loops, each loop having a first end that extends from a first side of the second component and a second end that extends from a second side of the second component opposite the first side,
    wherein the plurality of loops comprises at least 10 loops forming a loosely would ball shape and wherein the marker is positioned at a geometric center of the ball shape.

2. A marking device comprising:
    a first component being a wound arrangement of bioabsorbable suture material;
    a second component being a unitary piece of metal forming a marker; and
    wherein the first component includes multiple passes of the suture material forming a body defined by the wound arrangement of the suture material with the second component carried and supported by the body, and
    wherein the wound arrangement of the first component includes multiple passes of the suture material through the second component to form a plurality of loops, each loop having a first end that extends from a first side of the second component and a second end that extends from a second side of the second component opposite the first side,
    wherein the plurality of loops comprises at least 10 loops forming a loosely would ball shape and wherein the marker is positioned at a geometric center of the ball shape.

3. A marking device comprising:
    a delivery device having an elongate member with a lumen;
    a first component being a bioabsorbable suture material;
    a second component being a unitary piece of metal forming a marker; and
    wherein the first component includes multiple passes of the suture material forming a wound arrangement of the suture material with the second component carried and supported by the wound arrangement, and
    wherein the wound arrangement of the first component includes multiple passes of the suture material through the second component to form a plurality of loops, each loop having a first end that extends from a first side of the second component and a second end that extends from a second side of the second component opposite the first side,
    wherein the plurality of loops comprises at least 10 loops forming a loosely would ball shape and wherein the marker is positioned at a geometric center of the ball shape.

4. A biopsy marking apparatus for marking a target site within the breast, the apparatus comprising:
    a delivery device having an elongate member with a lumen;
    an echogenic body comprising a wound arrangement of bioabsorbable material; and
    a radiopaque marker carried and supported within the wound arrangement of the echogenic body, the marker having a recognizable shape distinguishable from calcifications, wherein the wound arrangement of the first component includes multiple passes of a suture material through the radiopaque marker to form a plurality of loops, each loop having a first end that extends from a first side of the radiopaque marker and a second end that extends from a second side of the radiopaque marker opposite the first side,
    wherein the plurality of loops comprises at least 10 loops forming a loosely would ball shape and wherein the marker is positioned at a geometric center of the ball shape,
    wherein the echogenic body is disposed within the lumen of the delivery device and deployable from the delivery device to the target site.

* * * * *